(12) United States Patent
Nantermet et al.

(10) Patent No.: US 7,354,942 B2
(45) Date of Patent: Apr. 8, 2008

(54) BENZYLETHER AND BENZYLAMINO BETA-SECRETASE INHIBITORS FOR THE TREATMENT OF ALZHEIMER'S DISEASE

(75) Inventors: Philippe G. Nantermet, Lansdale, PA (US); Hemaka A. Rajapakse, Wyncote, PA (US); Harold G. Selnick, Ambler, PA (US); Shaun R. Stauffer, Schwenksville, PA (US); Mary Beth Young, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/578,953

(22) PCT Filed: Nov. 19, 2004

(86) PCT No.: PCT/US2004/038927

§ 371 (c)(1),
(2), (4) Date: May 10, 2006

(87) PCT Pub. No.: WO2005/051914

PCT Pub. Date: Jun. 9, 2005

(65) Prior Publication Data

US 2007/0088165 A1  Apr. 19, 2007

Related U.S. Application Data

(60) Provisional application No. 60/602,434, filed on Aug. 18, 2004, provisional application No. 60/570,239, filed on May 12, 2004, provisional application No. 60/524,454, filed on Nov. 24, 2003.

(51) Int. Cl.
C07D 213/02 (2006.01)
A61K 31/44 (2006.01)

(52) U.S. Cl. ............ 514/357; 514/646; 514/408; 546/329; 546/339; 548/566; 564/305; 568/626

(58) Field of Classification Search ........ 546/329, 546/339; 548/566; 564/305; 568/626; 514/357, 514/408, 646

See application file for complete search history.

(56) References Cited

U.S. PATENT DOCUMENTS 6,812,346 B2  11/2004  Dube et al.

FOREIGN PATENT DOCUMENTS

| WO | WO 03/106405 | 12/2003 |
|----|---|---|
| WO | WO 2004/043916 | 5/2004 |
| WO | WO 2005/004802 | 1/2005 |
| WO | WO 2005/004803 | 1/2005 |
| WO | WO 2005/005374 | 1/2005 |
| WO | WO 2005/032471 | 4/2005 |

OTHER PUBLICATIONS

Coburn et al., "Identification of a Small Molecule Nonpeptide . . . ," J. Med. Chem., vol. 47, pp. 6117-6119 (2004).

*Primary Examiner*—Zinna N. Davis
(74) *Attorney, Agent, or Firm*—William Krovatin; John Todaro

(57) ABSTRACT

The present invention is directed to benzylether and benzylamino derivative compounds of formula (I)

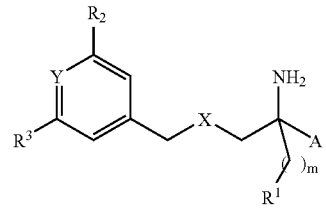

which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

18 Claims, No Drawings

BENZYLETHER AND BENZYLAMINO BETA-SECRETASE INHIBITORS FOR THE TREATMENT OF ALZHEIMER'S DISEASE

CROSS-REFERENCE TO RELATED APPLICATIONS

This application claims priority under 35 U.S.C. § 119(e) of U.S. Provisional applications Ser. No. 60/524,454, filed Nov. 24, 2003, 60/570,239, filed May 12, 2004, and 60/602,434, filed Aug. 18, 2004.

REFERENCE TO JOINT RESEARCH AGREEMENT

This invention was made as a result of activities undertaken within the scope of a Joint Research Agreement between Merck & Co., Inc. and Sunesis Pharmaceuticals, Inc.

FIELD OF THE INVENTION

The invention is directed to the field of compounds which are inhibitors of the activity of the β-secretase enzyme, and to the use of the compounds for the treatment of diseases in which the β-secretase enzyme is involved, such as Alzheimer's disease.

BACKGROUND OF THE INVENTION

Alzheimer's disease is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate soluble, COOH-truncated forms of APP ($APP_s$). Proteases that release APP and its fragments from the membrane are termed "secretases." Most $APP_s$ is released by a putative α-secretase which cleaves within the Aβ protein to release α-$APP_s$ and precludes the release of intact Aβ. A minor portion of $APP_s$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the abnormal cleavage of APP, production of Aβ, and accumulation of β amyloid plaques in the brain, which is characteristic of Alzheimer's disease (see R. N. Rosenberg, *Arch. Neurol.*, vol. 59, September 2002, pp. 1367-1368; H. Fukumoto et al, *Arch. Neurol.*, vol. 59, September 2002, pp. 1381-1389; J. T. Huse et al, *J. Biol. Chem.*, vol 277, No. 18, issue of May 3, 2002, pp. 16278-16284; K. C. Chen and W. J. Howe, *Biochem. Biophys. Res. Comm*, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to benzylether and benzylamino derivative compounds that are inhibitors of the β-secretase enzyme, and are useful in the treatment of diseases in which the β-secretase enzyme is involved, such as Alzheimer's disease. The invention is also directed to pharmaceutical compositions comprising these compounds, and the use of these compounds and compositions in the treatment of such diseases in which the β-secretase enzyme is involved.

DETAILED DESCRIPTION OF THE INVENTION

The present invention is directed to compounds of formula (I):

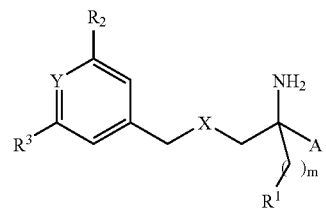

wherein:
X is O or NH;
Y is CH or N;
A is selected from the group consisting of
 (1) hydrogen,
 (2) —$C_{1-10}$ alkyl,
 (3) —$C_{2-10}$ alkenyl, and
 (4) —$C_{2-10}$ alkynyl
  wherein said alkyl, alkenyl or alkynyl is unsubstituted or substituted with one or more
   (a) halo,
   (b) —$C_{3-8}$ cycloalkyl,
   (c) —OH,
   (d) —CN,
   (e) —O—$C_{1-10}$ alkyl,
   (f) phenyl, or
   (g) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
  and said phenyl and heteroaryl is unsubstituted or substituted with one or more
   (i) halo,
   (ii) —OH,
   (iii) —CN,
   (iv) —O—$C_{1-10}$ alkyl,
   (v) —$C_{1-10}$ alkyl,
   (vi) —$C_{2-10}$ alkenyl, (vii) —C$_{2-10}$ alkynyl, or
(viii) —C$_{3-8}$ cycloalkyl;
R$^1$ is (1) aryl selected from the group consisting of phenyl and napthyl, or
(2) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said aryl or heteroaryl is unsubstituted or substituted with one or more
(a) halo,
(b) —C$_{1-10}$ alkyl,
(c) —C$_{2-10}$ alkenyl,
(d) —C$_{2-10}$ alkynyl,
(e) —OH,
(f) —CN,
(g) —O—C$_{1-10}$ alkyl, or
(h) —C$_{3-8}$ cycloalkyl;
R$^2$ is selected from the group consisting of:
(1) (R$^4$—SO$_2$)N(R$^7$)—, wherein R$^4$ is
(a) —C$_{1-10}$ alkyl,
(b) —C$_{2-10}$ alkenyl,
(c) —C$_{2-10}$ alkynyl, or
(d) —C$_{3-8}$ cycloalkyl,
wherein said alkyl, alkenyl, alkynyl and cycloalkyl is unsubstituted or substituted with one or more
(i) halo,
(ii) —OH,
(iii) —CN,
(iv) —O—C$_{1-10}$ alkyl,
(v) —C$_{1-10}$ alkyl,
(vi) —C$_{2-10}$ alkenyl,
(vii) —C$_{2-10}$ alkynyl,
(viii) —C$_{3-8}$ cycloalkyl,
(ix) aryl selected from the group consisting of phenyl and napthyl, or
(x) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
and said aryl and heteroaryl is unsubstituted or substituted with one or more
(i) halo,
(ii) —OH,
(iii) —CN,
(iv) —O—C$_{1-10}$ alkyl,
(v) —C$_{3-8}$ cycloalkyl,
(vi) —C$_{1-10}$ alkyl,
(vii) —C$_{2-10}$ alkenyl, or
(viii) —C$_{2-10}$ alkynyl;
R$^7$ is selected from the group consisting of
(a) hydrogen,
(b) —C$_{1-10}$ alkyl,
(c) —C$_{2-10}$ alkenyl, or
(d) —C$_{2-10}$ alkynyl
wherein said alkyl, alkenyl or alkynyl is unsubstituted or substituted with one or more
(i) halo,
(ii) —OH,
(iii) —CN,
(iv) —O—C$_{1-10}$ alkyl,
(v) —C$_{3-8}$ cycloalkyl,
(vi) aryl selected from the group consisting of phenyl and napthyl, or
(vii) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said cycloalkyl, aryl or heteroaryl is unsubstituted or substituted with one or more
(i) halo,
(ii) —OH,
(iii) —CN,
(iv) —O—C$_{1-10}$ alkyl,
(v) —C$_{3-8}$ cycloalkyl, or
(vi) aryl selected from the group consisting of phenyl and napthyl;

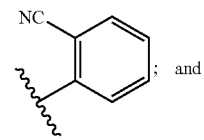; and

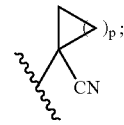;

R$^3$ is selected from the group consisting of

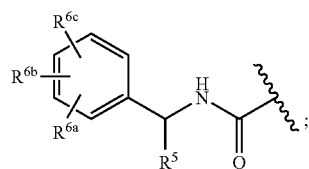

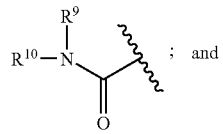; and

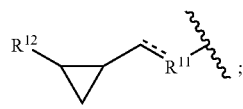;

wherein R$^5$ is selected from the group consisting of
(1) —C$_{1-10}$ alkyl,
(2) —C$_{2-10}$ alkenyl, or
(3) —C$_{2-10}$ alkynyl,
wherein said alkyl, alkenyl or alkynyl is unsubstituted or is substituted with one or more halo;
R$^{6a}$, R$^{6b}$, and R$^{6c}$ are independently selected from the group consisting of:
(1) hydrogen,
(2) halo,
(3) —C$_{1-10}$ alkyl,
(4) —C$_{2-10}$ alkenyl, (5) —$C_{2-10}$ alkynyl,
(6) —OH,
(7) —CN,
(8) —$C_{3-8}$ cycloalkyl, and
(9) —O—$C_{1-10}$ alkyl;

$R^9$ and $R^{10}$ are independently selected from the group consisting of
(1) hydrogen,
(2) —$C_{1-10}$ alkyl,
(3) —$C_{2-10}$ alkenyl,
(4) —$C_{2-10}$ alkynyl, or
(5) —$C_{3-8}$ cycloalkyl;
wherein said alkyl, alkenyl, alkynyl or cycloalkyl is unsubstituted or substituted with one or more
  (a) halo,
  (b) —OH,
  (c) —CN,
  (d) —$C_{3-8}$ cycloalkyl,
  (e) —O—$C_{1-10}$ alkyl
or $R^9$ and $R^{10}$ are joined together with the nitrogen atom to which they are attached to form a pyrrolidine ring, which is unsubstituted or substituted with one or more
  (a) $C_{1-10}$ alkyl,
  (b) —$C_{2-10}$ alkenyl,
  (c) —$C_{2-10}$ alkynyl,
  (d) —$C_{3-8}$ cycloalkyl,
  (e) —$(CH_2)_n$-phenyl,
  (f) —CN,
  wherein said alkyl, alkenyl or alkynyl is unsubstituted or substituted with one or more
    i) halo,
    ii) —OH,
    iii) —CN,
    iv) —O—$C_{1-10}$ alkyl, or
    v) —$C_{3-8}$ cycloalkyl,
  and said cycloalkyl and phenyl is unsubstituted or substituted with one or more
    i) halo,
    ii) —$C_{1-10}$ alkyl,
    iii) —$C_{2-10}$ alkenyl,
    iv) —$C_{2-10}$ alkynyl,
    v) —OH,
    vi) —CN,
    vii) —$C_{3-8}$ cycloalkyl, or
    viii) —O—$C_{1-10}$ alkyl;

$R^{11}$ is selected from the group consisting of
(1) —CH—,
(2) —O—, and
(3) —$NR^8$—,
provided that when $R^{11}$ is —CH— the dotted line forms a bond and when $R^{11}$ is —O— or —$NR^8$— the dotted line is absent;

$R^8$ is selected from the group consisting of
(1) hydrogen,
(2) $C_{1-10}$ alkyl,
(3) —$C_{2-10}$ alkenyl,
(4) —$C_{2-10}$ alkynyl, or
(5) —$CH_2$— phenyl,
wherein said alkyl, alkenyl, alkynyl or phenyl is unsubstituted or substituted with one or more
  (a) halo,
  (b) —OH,
  (c) —CN,
  (d) —$C_{3-8}$ cycloalkyl,
  (e) —O—$C_{1-10}$ alkyl;

$R^{12}$ is selected from the group consisting of
(1) hydrogen,
(2) —$C_{1-10}$ alkyl,
(3) —$C_{2-10}$ alkenyl,
(4) —$C_{2-10}$ alkynyl,
(5) halo,
(6) —$C_{3-8}$ cycloalkyl,
(7) aryl selected from the group consisting of phenyl and napthyl, and
(8) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said aryl and heteroaryl is unsubstituted or substituted with one or more
  (a) halo,
  (b) —OH,
  (c) —CN,
  (d) —O—$C_{1-10}$ alkyl,
  (e) —$C_{3-8}$ cycloalkyl,
  (f) —$C_{1-10}$ alkyl,
  (g) —$C_{2-10}$ alkenyl, or
  (h) —$C_{2-10}$ alkynyl m is 0, 1, 2 or 3;
n is 0, 1, 2, 3 or 4;
p is 1, 2, 3 or 4;

and pharmaceutically acceptable salts thereof.

In a preferred embodiment of the compounds of the invention, A is other than $CH_2OH$.

In another preferred embodiment of the compounds of the invention, X is O.

In another preferred embodiment of the compounds of the invention, A is selected from the group consisting of
(1) hydrogen,
(2) —$C_{1-10}$ alkyl, and
(3) —$C_{2-10}$ alkenyl,
wherein said alkyl is unsubstituted or substituted with one or more
  (a) halo,
  (b) —$C_{3-8}$ cycloalkyl,
  (c) —CN
  (d) —O—$C_{1-10}$ alkyl,
  (e) phenyl, or
  (f) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
and said alkenyl is unsubstituted or substituted with one or more
  (a) halo,
  (b) —$C_{3-8}$ cycloalkyl,
  (c) —OH,
  (d) —CN,
  (e) —O—$C_{1-10}$ alkyl,
  (f) phenyl, or
  (g) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
and said phenyl and heteroaryl is unsubstituted or substituted with one or more
(i) halo,
(ii) —OH,
(iii) —CN,
(iv) —O—$C_{1-10}$ alkyl,
(v) —$C_{1-10}$ alkyl, or
(vi) —$C_{3-8}$ cycloalkyl.

In a more preferred embodiment of the compounds of the invention, A is selected from the group consisting of
(1) —$C_{1-10}$ alkyl, and
(2) —$C_{2-10}$ alkenyl,
wherein said alkyl or alkenyl is unsubstituted or substituted with one or more
(a) halo,
(b) —$C_{3-8}$ cycloalkyl,
(c) —CN
(d) —O—$C_{1-10}$ alkyl,
(e) phenyl, or
(f) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl.

In a more preferred embodiment of the compounds of the invention, A is unsubstituted —$C_{1-10}$ alkyl or unsubstituted —$C_{2-10}$ alkenyl. In a still further preferred embodiment, A is unsubstituted —$C_{1-6}$ alkyl or unsubstituted —$C_{2-6}$ alkenyl. In an even more preferred embodiment, A is unsubstituted —$C_{1-4}$ alkyl or unsubstituted —$C_{2-4}$ alkenyl.

In a preferred embodiment of the compounds of the invention, $R^1$ is selected from the group consisting of
(1) aryl selected from the group consisting of phenyl and napthyl, or
(2) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said aryl or heteroaryl is unsubstituted or substituted with one or more
(a) halo,
(b) —$C_{1-6}$ alkyl,
(c) —OH,
(d) —CN, or
(e) —O—$C_{1-6}$ alkyl,
wherein m is 1 or 2.

In a more preferred embodiment, $R^1$ is phenyl, unsubstituted or substituted in one or two positions with halo, preferably with fluoro or chloro, and m is 1.

In a preferred embodiment of the compounds of the invention, $R^2$ is selected from the group consisting of
(1) ($R^4$—$SO_2$)N($R^7$)—, wherein $R^4$ is —$C_{1-6}$ alkyl, wherein said alkyl is unsubstituted or substituted with one or more
(i) halo,
(ii) —OH,
(iii) —CN,
(iv) —O—$C_{1-16}$ alkyl, or
(v) —$C_{1-6}$ alkyl, $R^7$ is selected from the group consisting of
(a) hydrogen,
(b) —$C_{1-6}$ alkyl,
wherein said alkyl is unsubstituted or substituted with one or more
(i) halo,
(ii) —OH,
(iii) —CN,
(iv) —O—$C_{1-6}$ alkyl,
(v) —$C_{1-6}$ alkyl,

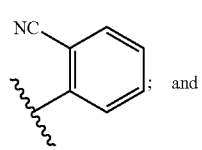

(2)

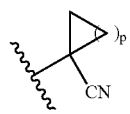

; and (3)

In a more preferred embodiment of the compounds of the invention, $R^2$ is ($R^4SO_2$)N($R^7$)—, wherein $R^4$ and $R^7$ are each $C_{1-6}$ alkyl, for example are each methyl.

In a preferred embodiment of the compounds of the invention, $R^3$ is selected from the group consisting of

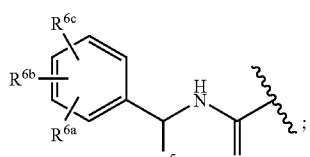

(a)

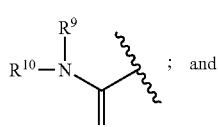

; and (b)

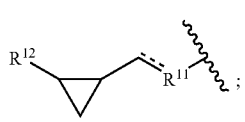

;

(c)

wherein $R^5$ is $C_{1-6}$ alkyl, optionally substituted with one or more halogen (preferably fluoro);

$R^{6a}$, $R^{6b}$, and $R^{6c}$ are independently selected from the group consisting of:
(1) hydrogen,
(2) halo,
(3) —$C_{1-6}$ alkyl,
(4) —OH,
(5) —CN, and
(6) —O—$C_{1-6}$ alkyl;

$R^9$ and $R^{10}$ are independently selected from the group consisting of
(1) hydrogen, and
(2) —$C_{1-6}$ alkyl, or $R^9$ and $R^{10}$ are joined together with the nitrogen atom to which they are attached to form a pyrrolidine ring, which is unsubstituted or substituted with one or more
(a) $C_{1-6}$ alkyl,
(b) —$(CH_2)_n$-phenyl;
wherein said alkyl and phenyl is unsubstituted or substituted with one or more
i) halo,
ii) —$C_{1-6}$alkyl,
iii) —OH,
iv) —CN, or
v) —O—$C_{1-6}$ alkyl; and $R^{11}$ is selected from the group consisting of
(1) —CH—,
(2) —O—, and
(3) —$NR^8$—, wherein $R^8$ is hydrogen provided that when $R^{11}$ is —CH— the dotted line forms a bond and when $R^{11}$ is —O— or —$NR^8$— the dotted line is absent; and $R^{12}$ is selected from the group consisting of
(1) hydrogen,
(2) —$C_{1-6}$ alkyl.

In a more preferred embodiment of the compounds of the invention, $R^3$ is

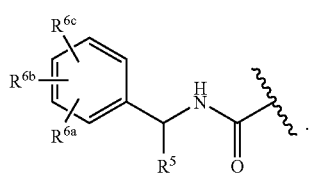

(a)

wherein $R^5$, $R^{6a}$, $R^{6b}$, $R^{6c}$ are as defined above. In preferred embodiments, $R^5$ is $C_{1-6}$ alkyl, optionally substituted with one or more halogen (preferably fluoro); and $R^{6a}$, $R^{6b}$, and $R^{6c}$ are independently selected from the group consisting of:
(1) hydrogen,
(2) halo,
(3) —$C_{1-6}$alkyl,
(4) —OH,
(5) —CN, and
(6) —O—$C_{1-6}$alkyl.

In a more preferred embodiment, $R^3$ is (a) as described above and $R^5$ is methyl. In another preferred embodiment, $R^3$ is (a) as described above and $R^{6a}$ and $R^{6b}$ are hydrogen and $R^{6c}$ is fluoro.

In another embodiment of the compounds of the invention, Y is CH.

In another embodiment of the compounds of the invention, Y is N.

Another embodiment of the present invention is directed to compounds of formula (II):

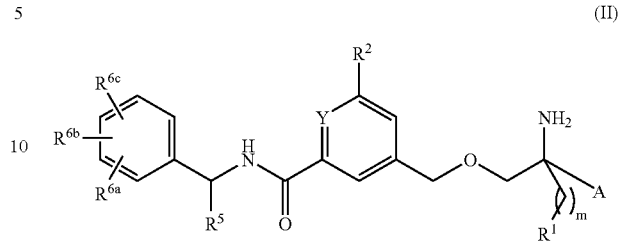

(II)

wherein A, Y, $R^1$, $R^2$, $R^5$, $R^{6a}$, $R^{6b}$, $R^{6c}$ and m are as defined above, and pharmaceutically acceptable salts thereof. In one embodiment of the compounds of formula (II), $R^5$ is methyl. In another embodiment of the compounds of formula (II), $R^{6a}$ and $R^{6b}$ are hydrogen and $R^{6c}$ is fluoro.

In a preferred embodiment of the compounds of formula (II), A is other than $CH_2OH$.

Another embodiment of the present invention is directed to compounds of the formula (III)

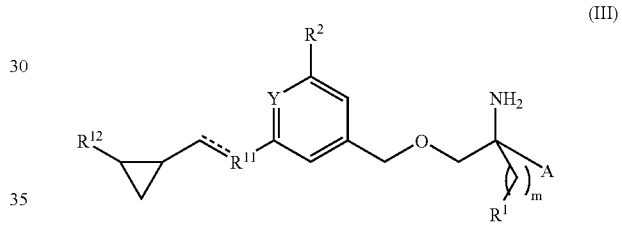

(III)

wherein A, Y, $R^1$, $R^2$, $R^{11}$, $R^{12}$ and m are as defined above, and pharmaceutically acceptable salts thereof. In preferred embodiments of the compounds of formula (III), Y is N and $R^{11}$ is $NR^8$.

In a preferred embodiment of the compounds of formula (III), A is other than $CH_2OH$.

Another embodiment of the present invention is directed to compounds of the formula (IV):

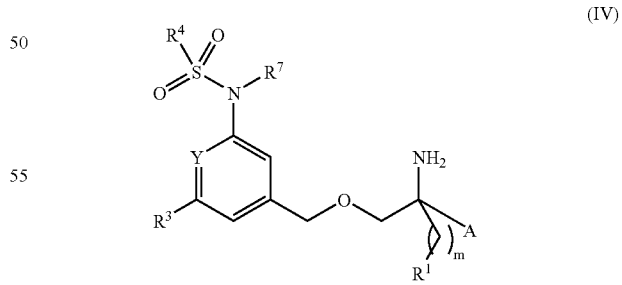

(IV)

wherein A, Y, $R^1$, $R^3$, $R^4$, $R^7$ and m are as defined above, and pharmaceutically acceptable salts thereof. In preferred embodiments, $R^4$ and $R^7$ are each $C_{1-6}$alkyl, for example are each methyl.

In a preferred embodiment of the compounds of formula (IV), A is other than $CH_2OH$.

Another embodiment of the invention is directed to compounds of the formula (V):

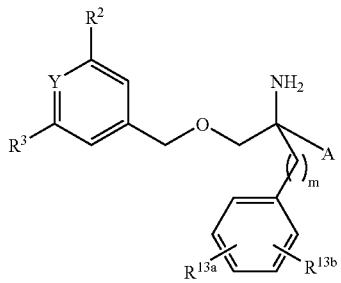

wherein $R^{13a}$ and $R^{13b}$ are independently selected from the group consisting of
(a) halo,
(b) —$C_{1-10}$ alkyl,
(c) —OH,
(d) —CN,
(e) —O—$C_{1-10}$ alkyl,
(f) hydrogen, and
(g) —$C_{3-8}$ cycloalkyl; and m is 1, and wherein A, Y, $R^2$ and $R^3$ are as defined above, and pharmaceutically acceptable salts thereof. In preferred embodiments, $R^{12}$ and $R^{13}$ are each halo, preferably either fluoro or chloro.

In a preferred embodiment of the compounds of formula (V), A is other than $CH_2OH$.

Another embodiment of the present invention is directed to compounds of formula (VI)

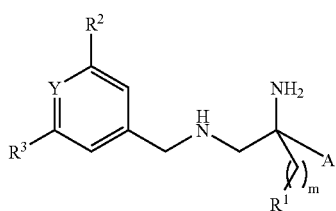

wherein A, Y, $R^1$, $R^2$, $R^3$ and m are as defined above, and pharmaceutically acceptable salts thereof.

In a preferred embodiment of the compounds of formula (VI), A is other than $CH_2OH$.

Another embodiment of the present invention includes a compound which is selected from the title compounds of the following Examples and pharmaceutically acceptable salts thereof.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

As used herein, the term "cycloalkyl," by itself or as part of another substituent, means a saturated cyclic hydrocarbon radical having the number of carbon atoms designated (e.g., $C_{3-8}$ cycloalkyl means a cycloalkyl group having from three to eight carbon atoms). Exemplary cycloalkyl groups include cyclopropyl, cyclobutyl, cyclopentyl, cyclohexyl and the like.

As used herein, the term "alkenyl," by itself of as part of another substituent, means a straight or branched chain hydrocarbon radical having a single carbon-carbon double bond and having the number of carbon atoms designated (e.g., $C_{2-10}$ alkenyl means an alkenyl group having from one to ten carbon atoms). Preferred alkenyl groups for use in the invention are $C_{2-6}$ alkenyl groups, having from two to six carbon atoms. Exemplary alkenyl groups include ethenyl, n-propenyl, isopropenyl, butenyl, and the like.

As used herein, the term "alkynyl", by itself or as part of another substituent, means a saturated straight or branched chain hydrocarbon radical having the number of carbon atoms designated (e.g., $C_{2-10}$ alkynyl means an alkynyl group having from two to ten carbon atoms). Preferred alkynyl groups for use in the invention are $C_{2-6}$ alkynyl groups, having from two to six carbon atoms. Exemplary alkynyl groups include ethynyl and propynyl.

The term "halo" or "halogen" includes fluoro, chloro, bromo and iodo.

The compounds of the instant invention have at least one asymmetric center. Additional asymmetric centers may be present depending upon the nature of the various substituents on the molecule. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of these compounds.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

The compounds of the present invention are prepared by the methods outlined in Schemes 1-10, below.

In Scheme 1, an amino acid derivative of type 1 is converted to the corresponding alcohol 2, which can be protected as its Boc derivative 2a. A two step alkylation of glycine Schiff base 3 gives protected quaternary amino acid derivatives such as 4. Schiff base deprotection, followed by ester reduction, provides an alternate route to compound 2. The alkylation of 3 for the synthesis of 4 may be performed in an enantioselective manner as described in the literature (see K. Maruoka et al, *J. Am. Chem. Soc.* 2000, 122, 5228-5229 and M. North et al, *Tetrahedron Lett.* 2003, 44, 2045-2048).

Scheme 1

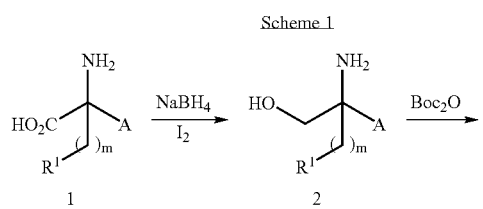

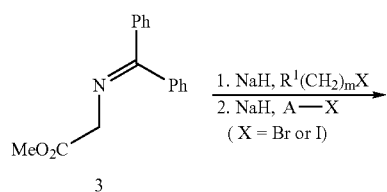

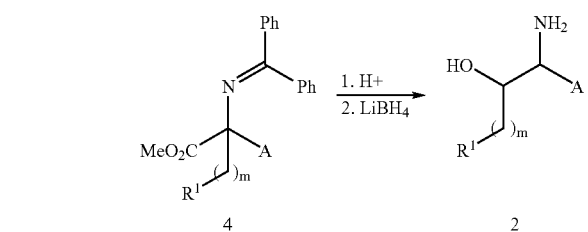

In Scheme 2, below, dimethyl 5-aminoisophthalate 5 is converted to bromide 6 via a 6-step sequence involving sulfonylation, alkylation, hydrolysis, amine coupling, reduction, and bromination. Deprotonation of alcohol 2 followed by alkylation with bromide 6 gives access to derivative 7.

Scheme 2

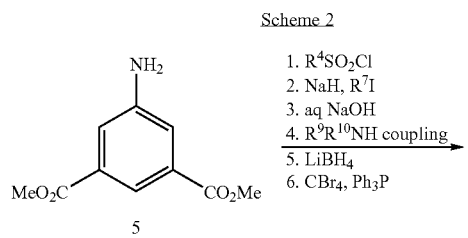

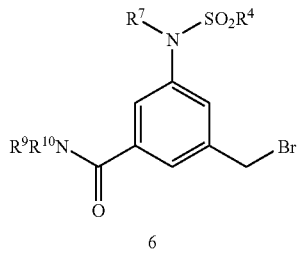

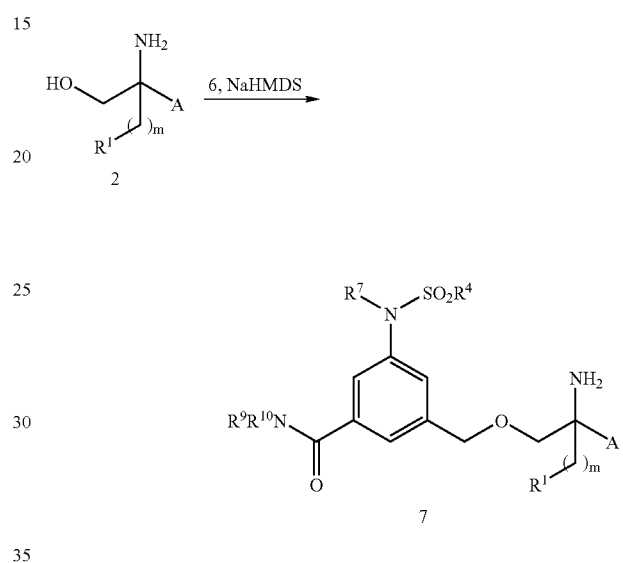

Scheme 3 illustrates the preparation of bromide of type 9 from dimethyl 5-iodoisophthalate 8 via Pd coupling, hydrolysis, amide coupling, reduction and bromination. Alkylation of alcohol 2 with bromide 9 gives access to ether 10.

Scheme 3

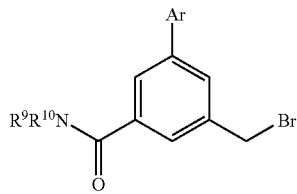

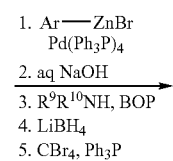

-continued

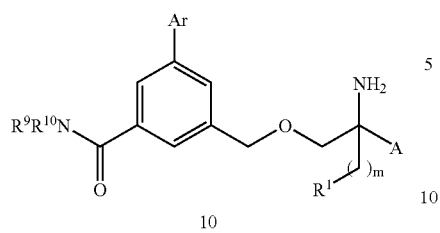
10

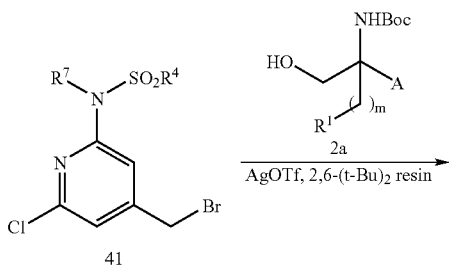
41

Scheme 4 illustrates the preparation of bromides of type 13 which are then coupled to diol 2 as described in scheme 2. Installation of both side chains using Pd⁰ coupling methodology followed by reduction of the ester moiety and subsequent bromination provides 13.

Scheme 4

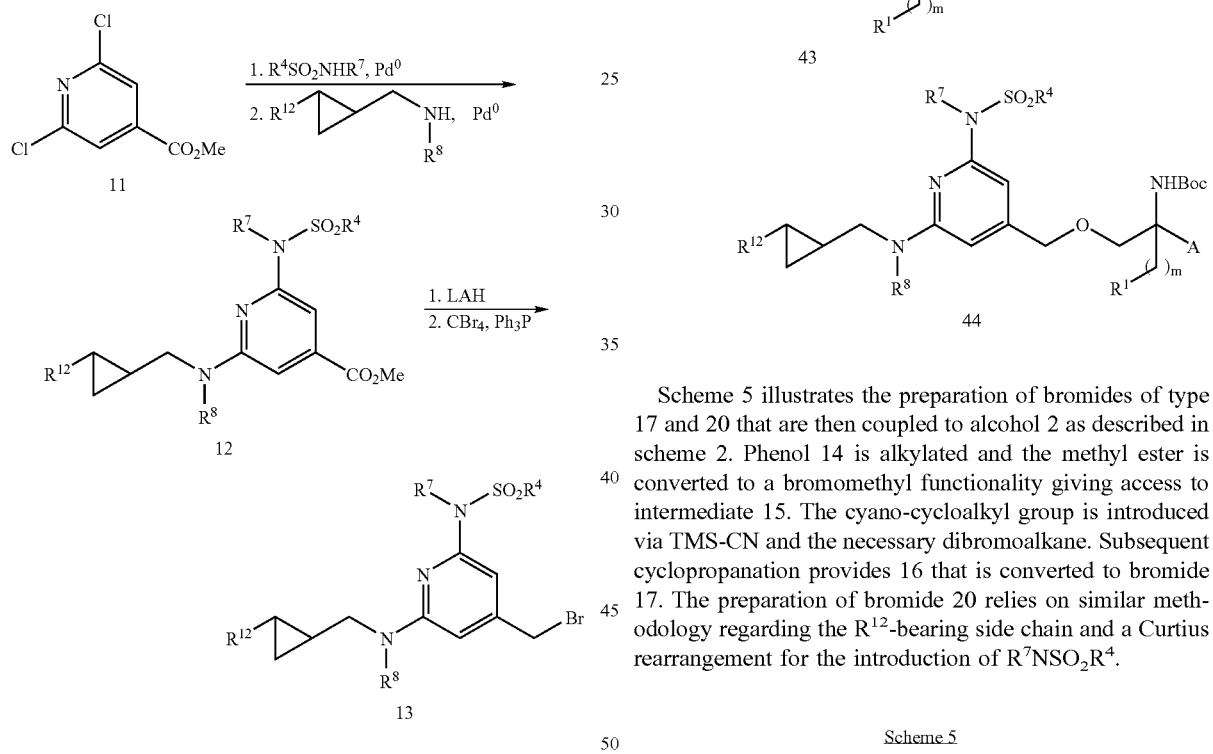

Scheme 4A, which is an alternative to Scheme 4, describes the installation of the ether linkage prior to the incorporation of the left hand amine, relying on similar methodology as described in schemes 2 and 4.

Scheme 4A

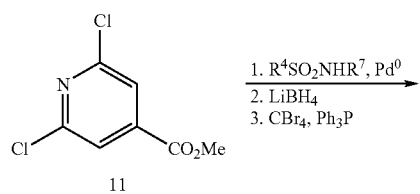

Scheme 5 illustrates the preparation of bromides of type 17 and 20 that are then coupled to alcohol 2 as described in scheme 2. Phenol 14 is alkylated and the methyl ester is converted to a bromomethyl functionality giving access to intermediate 15. The cyano-cycloalkyl group is introduced via TMS-CN and the necessary dibromoalkane. Subsequent cyclopropanation provides 16 that is converted to bromide 17. The preparation of bromide 20 relies on similar methodology regarding the R¹²-bearing side chain and a Curtius rearrangement for the introduction of R⁷NSO₂R⁴.

Scheme 5

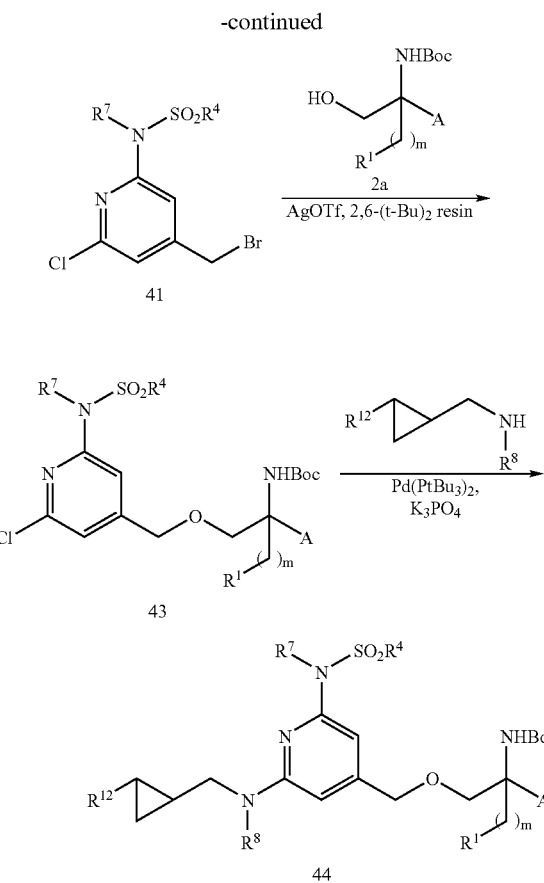

in scheme 2. The first preparation relies on conversion of the methyl ester to an aldehyde and a Wittig coupling to install the $R^{12}$-bearing alkene. The second preparation is based on an indenium/palladium coupling strategy.

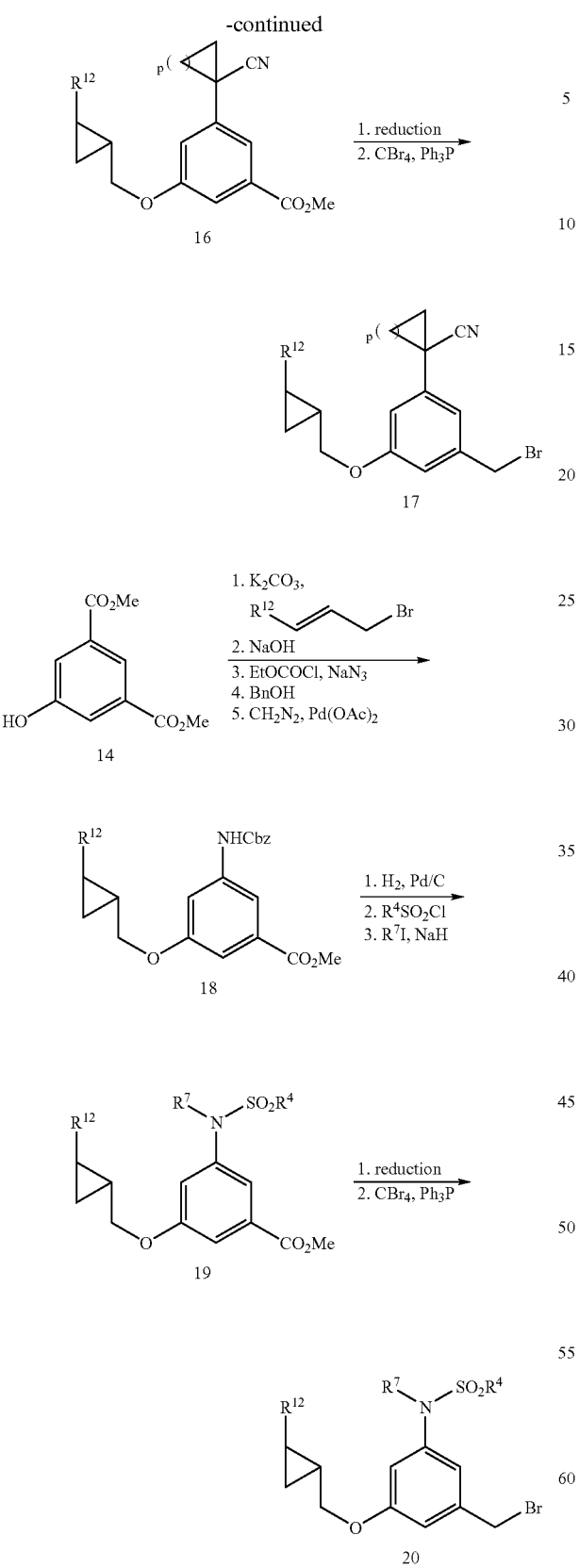

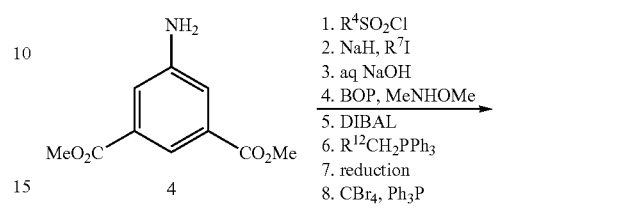

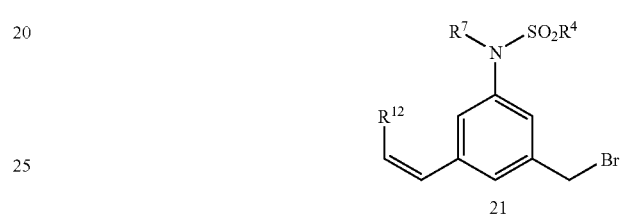

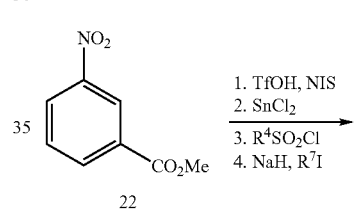

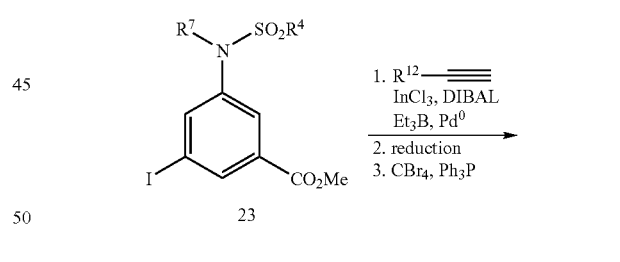

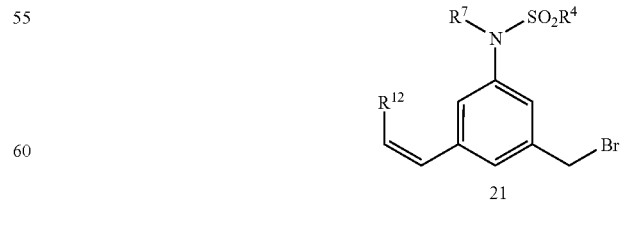

Scheme 6 illustrates two alternative preparations of bromide of type 21 that is then coupled to alcohol 2 as described In Scheme 7, chloroethers of type 24 can be converted to the corresponding acids of type 25, that can then be coupled to the left hand amines to afford pyridine amides of type 26.

Scheme 7
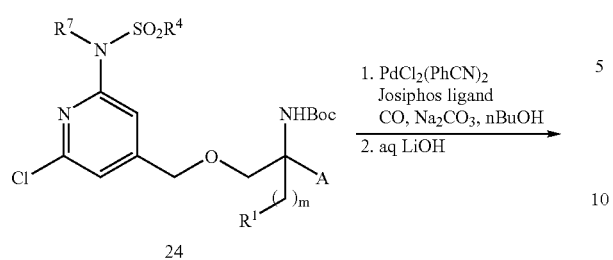
24
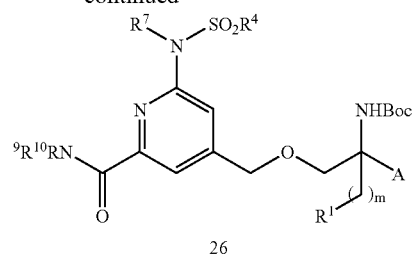
26
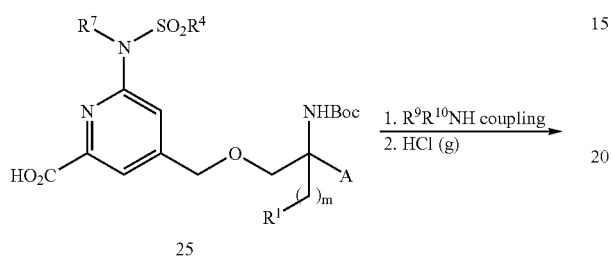
25
Scheme 8 describes the preparation of amides of type 30 and amines of type 31. Acid 27 is obtained from dimethyl 5-aminoisophtalate 5 using similar transformations as described before. Amides 30 are prepared using standard coupling reagents while amines 31 are derived from bromide 29 obtained from acid 28 by reduction and bromination.
Scheme 8
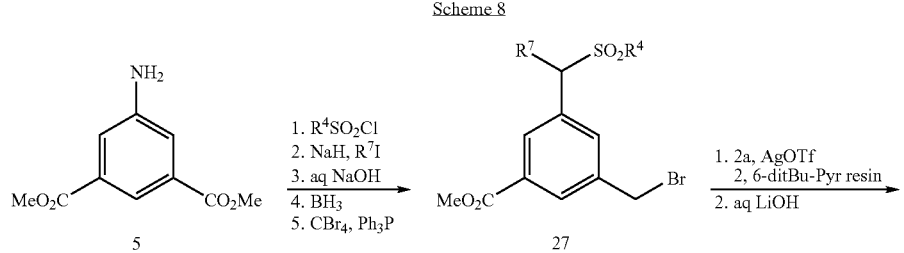
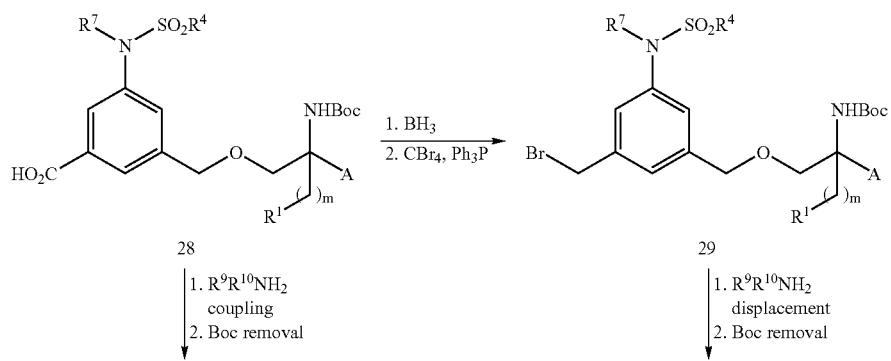
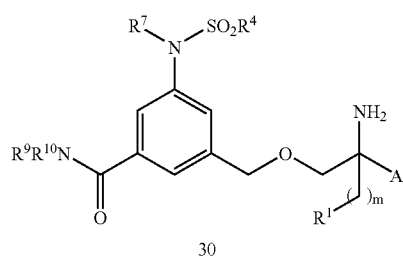
30
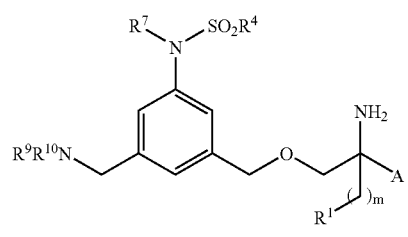
31

The general preparation of benzyl bromides of type 33 is shown as Scheme 9. Starting with 32, bromination of the benzyl alcohol, cyanide displacement of the resulting benzyl bromide and alkylation with the appropriate dibromoalkane provides the corresponding cyanocarbocycle. Ester monohydrolysis, acid reduction and bromination gives access to benzyl bromide 33. Etherification with amino alcohol 2a and ester hydrolysis yields acid 34, which can be coupled with the desired amine. Removal of the Boc protecting group gives the desired final product 35.

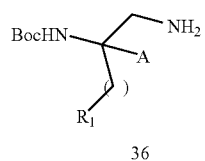

36

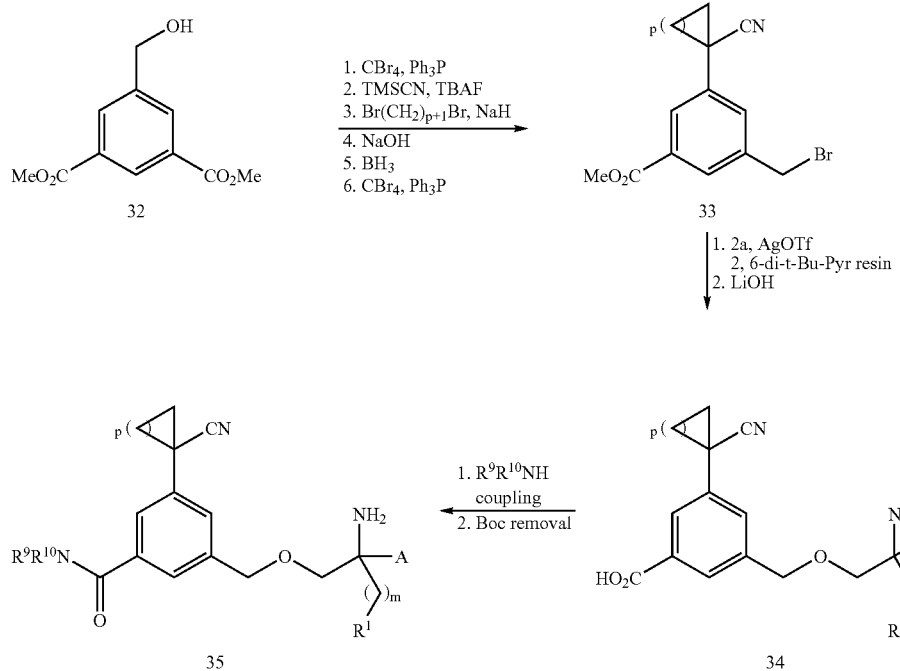

The general preparation of benzyl amino compounds of type 37 and 38 is shown as Scheme 10. Starting with amino acid 1, esterification and Boc protection, followed by reduction with DIBAL afforded the Boc protected aminoalcohol. The alcohol was oxidized to the aldehyde and reductively aminated with benzyl amine. The resulting benzyl group was removed using Pd(OH)$_2$ and a H$_2$ atmosphere to afford the desired amine precursor 36. Displacement of benzyl bromide 6 with 36 and deprotection gives access to final compounds of type 37. Ester-hydrolysis of 12, followed by EDC coupling with 36, borane reduction of the resulting amine and removal of the Boc protecting group gives the desired final products of type 38.

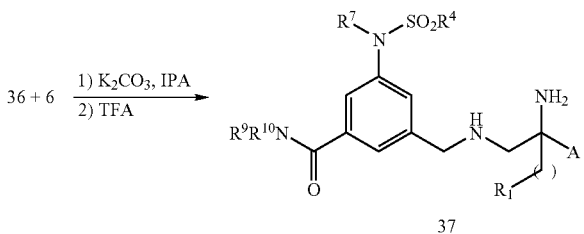

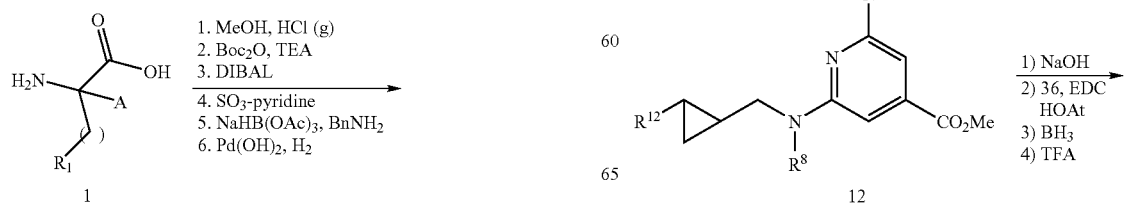

-continued

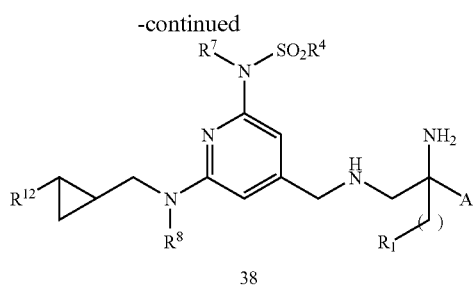

38

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic, trifluoroacetic acid and the like. Particularly preferred are citric, hydrobromic, hydrochloric, maleic, phosphoric, sulfuric, fumaric, tartaric and trifluoroacetic acids.

The present invention is directed to the use of the compounds disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The present invention is further directed to a method for the manufacture of a medicament or a composition for inhibiting β-secretase enzyme activity or β-site amyloid precursor protein-cleaving enzyme activity in humans and animals comprising combining a compound of the present invention with a pharmaceutical carrier or diluent. The invention is also directed to a method for the manufacture of a medicament or a composition for treating Alzheimer's Disease in humans and animals, comprising combining a compound of the present invention with a pharmaceutical carrier or diluent.

The compounds of the present invention have utility in treating Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, Down syndrome, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with: anti-Alzheimer's agents, for example other beta-secretase inhibitors or gamma-secretase inhibitors; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine $H_3$ antagonists; AMPA agonists; PDE IV inhibitors; $GABA_A$ inverse agonists; neuronal nicotinic agonists; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, which may be formulated according to the known art, or may be administered in the form of suppositories for rectal administration of the drug.

The compounds of the present invention may also be administered by inhalation, by way of inhalation devices known to those skilled in the art, or by a transdermal patch.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician. As used herein, the term "treatment" refers to the treatment of the mentioned conditions, particularly in a patient who demonstrates symptoms of the disease or disorder.

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating Alzheimer's disease or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

Specific dosages of the compounds of the present invention, or pharmaceutically acceptable salts thereof, for administration include 1 mg, 5 mg, 10 mg, 30 mg, 80 mg, 100 mg, 150 mg, 300 mg and 500 mg. Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions useful for treatment may comprise about 1 mg, 5 mg, 10 mg, 30 mg, 80 mg, 100 mg, 150 mg, 300 mg and 500 mg of active ingredient.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

FRET Assay: A homogeneous end point fluorescence resonance energy transfer (FRET) assay is used with the substrate ([TAMRA-5-CO-EEISEVNLDAEF-NHQSY] QFRET), which is cleaved by BACE 1 to release the fluorescence from TAMRA. The Km of the substrate is not determined due to the limit of solubility of the substrate. A typical reaction contains approximately 30 nM enzyme, 1.25 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction proceeds for 30 min and the liberation of TAMRA fragment is measured in a 96-well plate LJL Analyst AD using an excitation wavelength of 530 nm and an emission wavelength of 580 nm. Under these conditions, less than 10% of substrate is processed by BACE 1. The enzyme used in these studies was soluble (transmembrane domain and cytoplasmic extension excluded) human protein produced in a baculovirus expression system. To measure the inhibitory potency of compounds, solutions of inhibitor in DMSO (four concentrations of the inhibitors were prepared: 1 mM, 100 μM, 10 μM, 1 μM) were included in the reactions mixture (final DMSO concentration is 0.8%). All experiments were conducted at rt using the standard reaction conditions described above. To determine the $IC_{50}$ of the compound, competitive equation V0/Vi=1+[I]/[IC50] was used to predict the inhibitory potency of the compounds. The errors in reproducing the dissociation constants are typically less than two-fold.

HPLC assay: A homogeneous end point HPLC assay is used with the substrate (coumarin-CO-REVNFEVEFR), which is cleaved by BACE 1 to release the N-terminal fragment attached with coumarin. The Km of the substrate is greater than 100 μM and can not be determined due to the limit of solubility of the substrate. A typical reaction contains approximately 2 nM enzyme, 1.0 μM of the substrate, and buffer (50 mM NaOAc, pH 4.5, 0.1 mg/ml BSA, 0.2% CHAPS, 15 mM EDTA and 1 mM deferoxamine) in a total reaction volume of 100 μl. The reaction proceeds for 30 min and the reaction is stopped by the addition of 25 μL of 1 M Tris-HCl, pH 8.0. The resulting reaction mixture is loaded on the HPLC and the product is separated from substrate with 5 min linear gradient. Under these conditions, less than 10% of substrate is processed by BACE 1. The enzyme used in these studies was soluble (transmembrane domain and cytoplasmic extension excluded) human protein produced in a baculovirus expression system. To measure the inhibitory potency for compounds, solutions of inhibitor in DMSO (12 concentrations of the inhibitors were prepared and the concentration rage was dependent on the potency predicted by FRET) were included in the reaction mixture (final DMSO concentration is 10%). All experiments were conducted at rt using the standard reaction conditions described above. To determine the $IC_{50}$ of the compound, four parameters equation is used for curve fitting. The errors in reproducing the dissociation constants are typically less than two-fold.

In particular, the compounds of the following examples had activity in inhibiting the beta-secretase enzyme in the aforementioned assays, generally with an $IC_{50}$ from about 1 nM to 100 μM. Such a result is indicative of the intrinsic activity of the compounds in use as inhibitors the beta-secretase enzyme activity.

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

The following abbreviations are used throughout the text:
Me: methyl
Et: ethyl
Bu: butyl
t-Bu: tert-butyl
Ar: aryl
Ph: phenyl
Ac: acetyl
Bn: benzyl
Boc: tert-butyloxy carbonyl
Pyr: pyridine
TFA: trifluoroacetic acid
DMF: N,N'-dimethyl formamide
DIPEA: Diisopropylethylamine
NIS: N-iodosuccinimide
DMF: (1,3-dimethyl)-2-imidazolidinone
TBAF: tetra-n-butylammonium fluoride
HMDS: hexamethyldisilazane
THF: tetrahydrofuran
DMSO: dimethylsulfoxide
EDTA: ethylene diamine tetraacetic acid
rac: racemic
CBz: Benzyloxycarbonyl
CDI: N,N'-carbonyldiimidazole
DIBAL: diisobutylaluminium hydride
BOP: Benzotriazol-1-yloxy-tris(dimethylamino)phosphonium hexafluorophosphate
TMS: trimethylsilyl
BSA: bovine serum albumin
CHAPS: 3-[(3-cholamidopropyl)dimethylammonio]-2-hydroxy-1-propanesulfonate
rt: room temperature
HPLC: high performance liquid chromatography

Intermediate I 2-amino-2-methyl-3-phenylpropan-1-ol (Scheme 1)

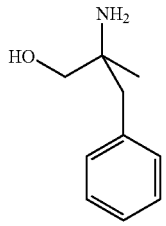

To a solution of rac-α-methyl-phenylalanine (1.74 g, 9.71 mmol) in 30 mL THF at rt was added NaBH$_4$ (0.92 g 24.27 mmol) in one portion. The solution was cooled to 0° C. Iodine (2.46 g, 9.71 mmol) in 5 mL THF was added dropwise over 30 min. After the addition was complete, the reaction was heated to reflux for 2 days. The reaction was then cooled to 0° C. and quenched by the addition of methanol until the bubbling subsided. The reaction mixture was acidified by the addition of 6N HCl until pH 1, stirred at 50° C. for 30 min and concentrated in vacuo. Purification using ion exchange chromatography (SCX cartridge) afforded 2-amino-2-methyl-3-phenylpropan-1-ol I as a white solid. $^1$H NMR (400 MHz, CDCl$_3$) δ 7.35-7.18 (m, 5H), 3.36 (A of AB, d, J=10.4 Hz, 1H), 3.31 (B of AB, d, J=10.4 Hz, 1H), 2.70 (s, 2H), 1.04 (s, 3H).

Intermediate II 2-amino-2-benzylhexan-1-ol (Scheme 1)

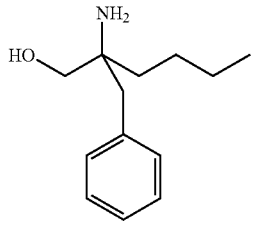

Step A: Alkylation

To a solution of rac-methyl-N-(diphenylmethylene)phenylalaninate (0.50 g, 1.4 mmol) (for synthesis see: O'Donnell et al, *J. Org. Chem.* 1982, 47, 2663-2666) in 6 mL DMF at 0° C. was added 95% NaH (0.14 g, 5.6 mmol). After 30 min, butyl iodide was added via syringe to the dark red reaction. After 30 min at 0° C., the reaction was warmed to rt for 14 h, then quenched by the addition of water. The aqueous layer was extracted with EtOAc (2×), the combined organics were washed with brine, dried over Na$_2$SO$_4$, filtered and concentrated. Purification by silica gel chromatography (40 g silica, 0->8% EtOAc/hexanes) afforded methyl-α-butyl-N-(diphenylmethylene)phenylalaninate as a viscous oil. $^1$H NMR (400 MHz, CDCl$_3$) δ 7.57 (m, 2H), 7.37-7.17 (m, 11H), 7.05-7.03 (m, 2H), 3.36 (d, J=11.5 Hz, 1H), 3.32 (d, J=11.5 Hz, 1H), 3.24 (s, 3H), 1.78 (m, 2H), 1.41 (m, 2H), 1.29-1.24 (m, 2H), 0.89 (t, J=7.2 Hz, 3H). LC/MS M+H=400.

Step B: Deprotection

To a solution of methyl-α-butyl-N-(diphenylmethylene)phenylalaninate (0.31 g, 0.78 mmol) from step A in 10 mL MeOH was added 3.33M hydrochloric acid (0.69 mL, 2.3 mmol). After 1.5 h at rt, the reaction was concentrated in vacuo to remove volatiles, then redissolved in saturated aqueous NaHCO$_3$. The aqueous layer was extracted with EtOAc (2×), the combined organics were washed with water, brine, dried over Na$_2$SO$_4$, filtered and concentrated. Purification by silica gel chromatography (20 g silica, 0->30% EtOAc/hexanes) afforded methyl-α-butylphenylalaninate as a viscous oil. $^1$H NMR (400 MHz, d$_4$-MeOH) δ 7.30-7.23 (m, 3H), 7.14-7.12 (m, 2H), 3.68 (d, J=13.1, 1H), 3.18 (d, J=13.1, 1H), 1.92 (m, 1H), 1.61 (m, 1H), 1.51-1.32 (m, 3H), 1.12 (m, 1H) M+H=236.

Step C: Reduction

To a solution of methyl ester (0.13 g, 0.55 mmol) from step B in 7.8 mL THF was added LiBH$_4$ (2.3 mL, 4.6 mmol, 2M in THF). After 2 h at reflux, the reaction was cooled to rt and quenched by the dropwise addition of MeOH, followed by acetone. After the volatiles were removed in vacuo, the remaining residue was redissolved in 23 mL 1N HCl and heated to 45° C. for 1.5 h. The volatiles were removed in vacuo, and the remaining residue was redissolved in saturated aqueous NaHCO$_3$. The aqueous layer was extracted with CHCl$_3$ (4×), the combined organics layers were dried over Na$_2$SO$_4$, filtered and concentrated to afford 2-amino-2-benzylhexan-1-ol II which was used for the next reaction without further purification. $^1$H NMR (400 MHz, CDCl$_3$) δ 7.32-7.18 (m, 5H), 3.32 (m, 2H), 7.70 (m, 2H), 1.53-1.31 (m, 6H), 0.93 (t, J=6.8 Hz, 3H) LCMS M+H=208.

Intermediate III 3-(bromomethyl)-N-[(1R)-1-(4-fluorophenyl)ethyl]-5-[methyl(methylsulfonyl)amino]benzamide (Scheme 2)

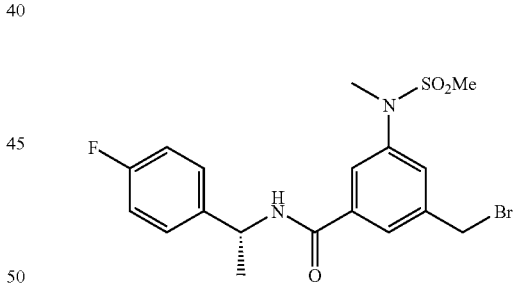

Step A: Sulfonylation

To a stirred slurry of dimethyl 5-aminoisophthalate (5.0 g, 23.90 mmol) in 100 mL CH$_2$Cl$_2$/pyridine (3:1) at 0° C. was added methanesulfonyl chloride (1.85 mL, 23.90 mmol). The resulting mixture was stirred for 4 h at rt. The solvent was removed in vacuo and ethyl acetate (100 mL) was added resulting in precipitate formation. The product was collected by filtration to give the sulfonamide as a white solid. 1H NMR (DMSO$_{d6}$) δ 8.15 (s, 1H), 8.02 (s, 2H), 3.89 (s, 6H), 3.02 (s, 3H) LCMS [M-OCH$_3$]$^+$=256.16.

Step B: Methylation

To a solution of sodium hydride (0.153 g, 3.83 mmol, 60% oil dispersion) in 10 mL DMF was added sulfonamide (1.0 g, 3.48 mmol) from step A followed by methyl iodide (0.43 mL, 6.97 mmol). After 1 hr the reaction was quenched with H₂O (100 mL) and extracted with EtOAc (3×50 nL). The organic extracts were dried over MgSO₄ and evaporated to give the product. ¹H NMR (DMSO$_{d6}$) δ 8.40 (s, 1H), 8.19 (s, 2H), 3.91 (s, 6H), 3.34 (s, 3H), 3.01 (s, 3H). LCMS [M+H]=302.15.

Step C: Hydrolysis

Diester (1.03 g, 3.38 mmol) from step B was dissolved in 50 mL THF:MeOH (1:1) and cooled to 0° C. 1N NaOH (3.38 mL, 3.38 mmol) was added and the reaction was allowed to warm to rt over 8 h. The solution was acidified with 1N HCl (30 mL) and extracted with EtOAc (3×50 mL). The combined organic extracts were washed with brine and dried over MgSO₄, filtered and concentrated in vacuo. Purification by silica gel chromatography (5% MeOH/CHCl₃ containing 1% HOAc) gave the mono acid. ¹H NMR (DMSO$_{d6}$) δ 8.30 (s, 1H), 8.10 (s, 2H), 3.84 (s, 3H), 3.27 (s, 3H), 2.94 (s, 3H). LCMS (M+H)=288.16.

Step D: Amine Coupling

A solution containing 0.133 g (0.46 mmol) of the monoacid from step C in 5 mL CH₂Cl₂, BOP reagent (0.235 g, 0.55 mmol), (R)-(+)-α-methylbenzylamine (0.071 mL, 0.55 mmol), and diisopropylamine (0.24 mL, 1.39 mmol) was stirred at ambient temperature for 1 h. Evaporation of the solvent and column chromatography on silica gel (90% EtOAc/Hexanes) afforded the benzyl amide. ¹H NMR (CDCl₃) δ 8.26 (s, 1H), 8.17 (s, 1H), 8.06 (s, 1H), 7.31 (m, 5H), 6.50 (d, J=7.1 Hz, 1H), 5.33 (q, J=7.1 Hz, 1H), 3.96 (s, 3H), 3.37 (s, 3H), 2.88 (s, 3H), 1.64 (d, J=7.0 Hz, 3H). LCMS (M+H)=391.20.

Step E: Reduction

To a solution of methyl ester from step D (627 mg, 1.54 mmol) in 5 mL THF cooled to 0° C. was added LiBH₄ (2.3 ml, 4.62 mmol, 2.0 M in THF) dropwise. The reaction mixture was stirred at 0° C. for 20 min, warmed to rt for 14 h, then quenched by adding MeOH dropwise. The volatiles were removed in vacuo, and the residue was taken in EtOAc, washed with water, brine, dried over sodium sulfate and concentrated in vacuo to provide crude alcohol which was brominated as is in step F.

Step F: Bromination

To a solution of crude alcohol from step E (355 mg, 0.93 mmol) and carbon tetrabromide (0.4 g, 1.2 mmol) in 4.6 mL 1:1 CH₃CN:CH₂Cl₂ was added triphenylphosphine (0.29 g, 1.1 mmol) in 4.6 mL 1:1 CH₃CN:CH₂Cl₂ dropwise. After stirring at rt for 45 min, two additional batches of carbon tetrabromide and triphenyl phosphine (200 mg/150 mg and 20 mg/15 mg) were added at 30 min intervals, until the reaction appeared complete by LC/MS analysis. The reaction mixture was concentrated and purified by flash chromatography (40 g silica, 25->60% EtOAc/hexanes) to afford 220 mg of 3-(bromomethyl)-N-[(1R)-1-(4-fluorophenyl)ethyl]-5-[methyl(methylsulfonyl)amino]benzamide. ¹H NMR (400 MHz, CDCl₃) δ 7.73 (s, 1H), 7.65 (s, 1H), 7.57 (s, 1H), 7.32-7.40 (m, 2H), 7.09-7.01 (m, 2H), 6.32 (d, J=7.6 Hz, 1H), 5.36-5.24 (m, 1H), 4.50 (s, 2H), 3.36 (s, 2H), 2.78 (s, 3H), 1.62 (d, J=6.5 Hz, 3H).

Intermediate IV tert-butyl (1-benzyl-2-hydroxy-1-methylethyl)carbamate (Scheme 1)

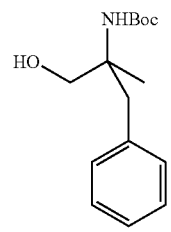

A solution of 2-amino-2-methyl-3-phenylpropan-1-ol (255 mg, 1.54 mmol, Intermediate I, Scheme 1) and diter-tbutyldicarbonate (337 mg, 1.54 mmol) was stirred at rt for 16 h, concentrated in vacuo and purified by flash chromatography (silica, 0-25% EtOAc/hexanes) to provide tert-butyl (1-benzyl-2-hydroxy-1-methylethyl)carbamate, as a white solid. ¹H NMR (400 MHz, CDCl₃) δ 7.35-7.15 (m, 5H), 4.48 (br s, 1H), 4.17 (br s, 1H), 3.76-3.62 (m, 2H), 3.19 (A of AB, d, J=13.6 Hz, 1H), 2.81 (B of AB, d, J=13.6 Hz, 1H), 1.47 (s, 9H), 1.07 (s, 3H).

Intermediate V

N-benzyl-1-(2-trans-methylcyclopropyl)methanamine

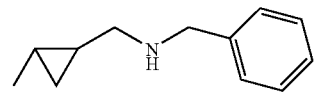

Step A: Coupling

In a 2 L flask trans-crotonoic acid (15.0 g, 174 mmol), benzyl amine (20.5 g, 192 mmol) and DIPEA (36.7 g, 192 mmol) were dissolved in 700 mL of dichloromethane. To this solution at rt. EDC-HCl (36.7 g, 192 mmol) was added as a solid portionwise and stirred overnight. The reaction mixture was poured onto 10% aq. KHSO₄ (250 mL). The layers were separated and washed once again with 10% aq. KHSO₄. The organic layer was subsequently washed with H₂O (200 mL) followed by brine (150 mL), dried over Na₂SO₄ and concentrated to dryness to white crystals of (2E)-N-benzylbut-2-enamide: ¹H NMR (400 MHz, CDCl₃) δ 7.28 (m, 5H), 6.85 (sext, J=6.8 Hz, 1H), 5.78 (dd, J=15.2, 1.6 Hz, 2H), 4.47 (d, J=5.6 Hz, 2H), 1.82 (dd, J=7.2, 1.6 Hz, 3H).

Step B: Cyclopropanation

In an Erlenmeyer flask containing Et₂O (300 mL) and aq. 40% KOH (111 mL) with vigorous stirring was added 1-methyl-3-nitro-1-nitrosoguanidine (11.1 g, 67 mmol) portionwise over 5 min. at rt. Upon complete addition stirring was ceased and the aq. layer frozen in a −78° bath. The ether layer was decanted into an Erlenmeyer with KOH pellets. The contents allowed to stand for 5 min., decanted into a third flask with KOH pellets and then poured onto a Et₂O/THF solution (200 mL/50 mL) containing (2E)-N-benzyl-but-2-enamide (3.0 g, 17.1 mmol from step A). Pd(OAc)₂

(180 mg, 0.9 mmol) was subsequently added and the reaction allowed to warm to rt and stir for 1 h. Nitrogen was bubbled through the reaction for 10 min. The mixture was washed with H$_2$O (150 mL). The organic layer was isolated and subsequently dried over Na$_2$SO$_4$. Solvent removal and purification by flash chromatography on SiO$_2$ (EtOAc/hexanes) gave N-benzyl-trans-2-methylcyclopropanecarboxamide: $^1$H NMR (400 MHz, CDCl$_3$) δ 7.28 (m, 5H), 5.81 (br s, 1H), 4.43 (dd, J=5.6, 2.4 Hz, 2H), 1.37 (m, 1H), 1.17 (m, 1H), 1.07 (d, J=6.0 Hz, 3H), 1.04 (overlapping m, 1H), 0.56 (m, 1H).

Step C: Reduction

A 500 mL flask charged with N-benzyl-traits-2-methyl-cyclopropanecarboxamide (from step B, 3.9 g, 20.6 mmol) in THF (80 mL) was added BH$_3$-THF (1.0 M, 105 mL, 105 mmol) dropwise via an addition funnel. Upon complete addition (10 min.) the mixture was refluxed for 5 h. The mixture was allowed to cool to rt and quenched carefully with MeOH (15 mL). The mixture was concentrated to dryness, dissolved in dichloromethane and washed with 3M KOH. The organic layer was isolated, washed with brine, then dried over Na$_2$SO$_4$ and concentrated to dryness. The crude material was treated with 1N HCl in dioxane for 1 h at 50° C. The mixture was concentrated to give hydrochloride salt as a white solid. The solid was dissolved in sat. aq. NaHCO$_3$ (80 mL) and extracted with CHCl$_3$ (2×150 mL). The combined organic layers were washed with brine, dried over Na$_2$SO$_4$ and the solvent removed via rotorary evaporation to give after drying in vacuo N-benzyl-1-(2-trans-methylcyclopropyl)methanamine as an off-white semi-solid (quant.): $^1$H NMR (400 MHz, CDCl$_3$) δ 7.28 (m, 5H), 3.80 (s, 2H), 2.50 (d, J=6.8 Hz, 2H), 2.4 (br s, 1H), 1.02 (d, J=6.0 Hz, 3H), 0.69 (m, 1H), 0.52 (m, 1H), 0.23 (m, 2H).

Intermediate VI tert-butyl [1-benzyl-2-({2-chloro-6-[(methylsulfonyl)propyl)amino]pyridin-4-yl}methoxy)-1-methylethyl]carbamate (Scheme 4A)

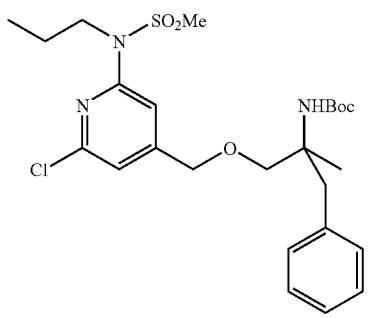

Step A: Sulfonamide Installation

Methyl 2,6-dichloroisonicotinate (10 g, 48.5 mmol), methyl(propylsulfonyl)amine (7.99 g, 58.2 mmol), potassium phosphate (14.4 g, 68 mmol), Xantphos (1.69 g, 2.9 mmol) and tris(dibenzylideneacetone)dipalladium (0.89 g, 0.97 mmol) were added to a dry, argon flushed flask. Dioxane (400 mL) was added, the solution degassed with argon and the reaction was heated to 100° C. for 16 h. The reaction was cooled to rt, filtered through celite and evaporated in vacuo. Flash chromatography (silica, 0-35% EtOAc/hexanes) gave methyl 2-chloro-6-[(methylsulfonyl)(propyl)amino]isonicotinate as a yellow oil: $^1$H NMR (400 MHz, CD$_3$OD) δ 7.88 (s, 1H), 7.72 (s, 1H), 3.96 (s, 3H), 3.91 (t, J=6.4 Hz, 2H), 3.13 (s, 3H), 1.68-1.53 (m, 2H), 0.93 (t, J=7.5 Hz, 3H).

Step B: Reduction

To a solution of methyl 2-chloro-6-[(methylsulfonyl)(propyl)amino]isonicotinate (3.5 g, 11.5 mmol) in THF (50 mL) cooled to 0° C. was added LiBH$_4$ (17.2 mL, 34.4 mmol, 2 M in THF). After 10 min, the reaction mixture was allowed to warm to rt and stirred for 3.5 h. The reaction mixture was carefully quenched with EtOAc, MeOH and water. Following dilution with EtOAc, the organic layer was extracted, washed with brine, dried over sodium sulfate and concentrated in vacuo to provide N-[6-chloro-4-(hydroxymethyl)pyridin-2-yl]-N-propylmethanesulfonamide which was used as is in the bromination step.

Step C: Bromination

To a solution of N-[6-chloro-4-(hydroxymethyl)pyridin-2-yl]-N-propylmethanesulfonamide (740 mg, 2.65 mmol) in dichloromethane (20 mL) cooled to 0° C. was added carbon tetrabromide (967 mg, 2.92 mmol) and triphenylphosphine (765 mg, 2.92 mmol). After 10 min, the reaction mixture was allowed to warm to rt and stirred for 0.5 h. The reaction mixture was concentrated in vacuo and purified by flash chromatography (silica, 0-25% EtOAc/hexanes) to provide N-[4-(bromomethyl)-6-chloropyridin-2-yl]-N-propyl-methanesulfonamide as a white solid. $^1$H NMR (400 MHz, CDCl$_3$) δ 7.34 (s, 1H), 7.22 (s, 1H), 4.35 (s, 2H), 3.85 (t, J=7.6 Hz, 2H), 3.04 (s, 3H), 1.64-1.50 (m, 2H), 0.93 (t, J=7.2 Hz, 3H).

Step D: Ether Installation

To a solution of tert-butyl (1-benzyl-2-hydroxy-1-methylethyl)carbamate (250 mg, 0.94 mmol, intermediate IV) and N-[4-(bromomethyl)-6-chloropyridin-2-yl]-N-propyl-methanesulfonamide (290 mg, 0.85 mmol) in dichloromethane (20 mL) was added silver triflate (290 mg, 1.13 mmol) and 2,6-ditertbutylpyridine polymer bound (1.84 g, 2.83 mmol, Aldrich 37, 782-1). The reaction mixture was stirred at 50° C. in an oil bath for 16 h and then irradiated under microwave (Smith Synthesizer) at 90° C. for 45, 60 and 90 min intervals (3 runs, with addition of additional silver triflate and 2,6-ditertbutylpyridine polymer bound before 2nd and 3rd run). The reaction mixture was filtered on celite, rinsed with dichloromethane, concentrated in vacuo and purified by flash chromatography (silica, 0-30% EtOAc/hexanes) to provide tert-butyl [1-benzyl-2-({2-chloro-6-[(methylsulfonyl)(propyl)amino]pyridin-4-yl}methoxy)-1-methylethyl]carbamate. $^1$H NMR (400 MHz, CDCl$_3$) δ 7.34-7.16 (m, 7H), 4.56 (s, 2H), 4.50 (s, 1H), 3.83 (t, J=6.8 Hz, 2H), 3.66 (A of AB, d, J=9.2 Hz, 1H), 3.54 (B of AB, d, J=9.2 Hz, 1H), 3.15 (A of AB, d, J=13.2 Hz, 1H), 3.03 (s, 3H), 2.90 (B of AB, d, J=13.2 Hz, 1H), 1.64-1.50 (m, 2H), 1.47 (s, 9H), 1.26 (s, 3H), 0.92 (t, J=7.2 Hz, 3H).

Intermediate VII

4-{2-[tert-butoxycarbonyl)amino]-2-methyl-3-phenylpropoxy}methyl)-6-[(methylsulfonyl)(propyl)amino]pyridine-2-carboxylic acid (Scheme 7)

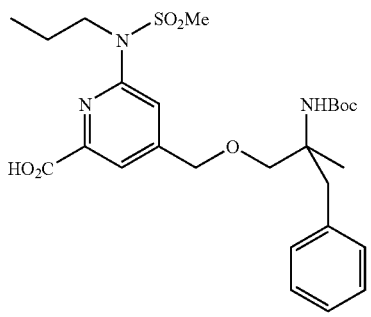

A suspension of tert-butyl [1-benzyl-2-({2-chloro-6-[(methylsulfonyl)(propyl)amino]pyridin-4-yl}methoxy)-1-methylethyl]carbamate (115 mg, 0.22 mmol, intermediate VI), sodium carbonate (70 mg, 0.66 mmol), PdCl$_2$(PhCN)$_2$ (2 mg, 0.004 mmol), 4A sieves and 1-[2-(dicyclohexylphasphanyl)ferrocenyl]ethyldicyclohexylphosphane (11 mg, 0.017 mmol, STREM) in n-butanol (2 ml, degassed with Argon), was purged with CO and stirred at 100° C. for 16 h under 1 atm of CO. The reaction mixture was diluted with dichloromethane, washed with water and brine, dried over sodium sulfate, concentrated in vacuo, azeothroped with toluene, and purified by flash chromatography (silica, 0-35% EtOAc/hexanes) to provide butyl 4-({2-[(tert-butoxycarbonyl)amino]-2-methyl-3-phenylpropoxy}methyl)-6-[(methylsulfonyl)(propyl)amino]pyridine-2-carboxylate as a yellow oil which was dissolved in 1:1 THF:MeOH (1.6 mL) and treated with aq LiOH (0.38 mL, 0.38 mmol, 1N) for 2 h at rt. The reaction mixture was acidified to pH 3-4 with 1N HCl, extracted with dichloromethane, dried over sodium sulfate, concentrated in vacuo, azeothroped with toluene to give 4-({2-[(tert-butoxycarbonyl)amino]-2-methyl-3-phenylpropoxy}methyl)-6-[(methylsulfonyl)(propyl)amino]pyridine-2-carboxylic acid as a yellow oil. $^1$H NMR (400 MHz, CDCl$_3$) δ 8.03 (s, 1H), 7.71 (s, 1H), 7.34-7.13 (m, 5H), 4.67 (s, 2H), 4.49 (s, 1H), 3.93 (t, J=7.6 Hz, 2H), 3.72 (A of AB, d, J=9.2 Hz, 1H), 3.62 (B of AB, d, J=9.2 Hz, 1H), 3.17 (A of AB, d, J=13.6 Hz, 1H), 3.05 (s, 3H), 2.90 (13 of AB, d, J=13.6 Hz, 1H), 1.70-1.55 (m, 2H), 1.46 (s, 9H), 1.27 (s, 3H), 0.96 (t, J=7.6 Hz, 3H).

Intermediate VIII

3-[(Z)-2-(2-methylcyclopropyl)vinyl]-5-[methyl(methylsulfonyl)amino]benzoic acid (Scheme 6)

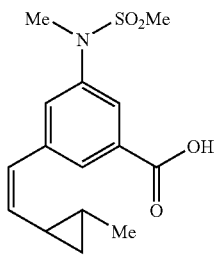

Step A: Iodination

To 3-Nitrobenzoate (35.3 g, 195 mmol) in triflic acid (100 mL) at 0° C. was added NIS (43.8 g, 195 mmol) in ten portions. Remove ice bath and stir for 48 hrs. The reaction typically goes to 50% completion. At this time more NIS could be added or cool to 0° C. and quench with careful dropwise addition of water. The mixture was extracted three times with EtOAc (250 mL) and the combined extracts were washed with a 10% NaHSO$_3$ solution, followed by water. The organics were dried over Na$_2$SO$_4$, concentrated, and purified on silica gel (10% EtOAc in Hex) affording the desired iodide.

Step B: Nitro Reduction

Tin chloride (88.6 g, 392 mmol) in EtOH (50 mL) was refluxed and the nitrobenzoate from step A (24.1 g, 78.4 mmol) in 1:1 THF:EtOH (100 mL) was added dropwise. The reaction mixture was refluxed for 30 minutes then cooled to 0° C. The resulting solution was basified to pH 8-9 with aq. Na$_2$CO$_3$. The aqueous layer was extracted three times with EtOAc (700 mL) and the combined extracts were washed with saturated NaHCO$_3$ then brine. The organics were dried over Na$_2$SO$_4$ and concentrated to afford the desired aniline which was used without further purification.

Step C: Mesylation

To a 0° C. solution of aniline from step B (21.7 g, 78.3 mmol) in 3:1 CH$_2$Cl$_2$:pyridine (75 mL) was added methanesulfonyl chloride (6.36 mL, 82.2 mmol). The ice bath was removed after 15 minutes and the solution was stirred overnight at rt. The reaction mixture was extracted several times with 1N HCl. The organic phase was dried, concentrated, and chromatographed (1:1 EtOAc:Hex) to afford the desired sulfonamide as a white solid.

Step D: Methylation

The sulfonamide from step C (23.6 g, 66.5 mmol) in DMF (75 mL) at 0° C. was treated with 60% NaH (2.92 g, 73.1 mmol). The solution stirred for 30 minutes before MeI (4.55 mL, 73.1 mmol) was added. The ice bath was removed and the solution was stirred at rt for 12 h. The reaction was quenched with saturated NH$_4$Cl solution and extracted three times with EtOAc (150 mL). The combined organics were washed with water (5×50 mL), dried, concentrated to afford 25.3 g of the desired methylated anilide which was used without further purification.

Step E: Oxidation

Trans-2-methylcyclopropanemethanol (7.0 g, 81 mmol) was added to a solution of PCC (28 g, 130 mmol) in CH$_2$Cl$_2$ (225 mL). The solution became black and was stirred for 3 h at rt. The reaction mixture was diluted with ether (250 mL) and decanted. The liquid solution was filtered through a 4 inch plug of Florisil and the solvent was removed by distillation through a Vigreux column to afford the desired aldehyde.

Step F: Corey-Fuchs Reaction

To a solution of PPh₃ (12.4 g, 47.5 mmol) in CH₂Cl₂ (100 mL) at 0 C was added CBr₄ (7.88 g, 23.7 mmol). The reaction mixture was stirred for 10 minutes then treated with the carboxaldehyde from step E (1.0 g, 12 mmol). The solution was stirred for 30 minutes at 0° C. then 1 hr at rt. Hexane was added and the solids were filtered, and the filtrate was concentrated to afford the desired dibromide.

Step G: Alkyne Formation

The dibromide from step F (15.4 g, 64.1 mmol) in 60 mL of cyclohexane at −78° C. was treated with 2.0 M n-BuLi in cyclohexane (64.1 mL, 128 mmol). The resulting reaction mixture was stirred at −78° C. for 1 hr then warmed to rt where it was stirred for 2 hr. The reaction was quenched with water and extract with cyclohexane (3×25 mL). The product was purified by distillation (bp=69-72° C.).

Step H: Coupling

A 100 mL 3-neck round bottom flask was charged with InCl₃ (0.829 g, 10.4 mmol) and dried under vacuum with a heat gun for 2 minutes. THF (16 mL) was added under nitrogen and the flask was immersed in a −78° C. ice bath. DIBAL-H (12.4 mL, 1M in hexanes) was then added dropwise and the resulting solution was stirred for 30 minutes at −78° C. After this time, the acetylene from step G (10.4 mmol) was added followed by 1.0 M Et₃B (1.6 mL, 1M in hexanes). This reaction mixture was stirred at −78° C. for 2.5 hr then warmed to rt. DMI (12 mL) and aryliodide from step D (1.47 g, 4.0 mmol) was added followed by a palladium trifurylphosphine complex (prepared from Pd₂(DBA)₃CHCl₃ (20 mg) and trifurylphosphine (28 mg) in THF (6 mL)). The resulting reaction mixture was heated at 60° C. for 2 hr, quenched with water and extracted with ether (3×50 mL). The combined organic extracts were dried, and concentrated and the product was purified on a chiral OJ column (60:40 Hexane w/0.1% TFA:EtOH). Collection of the first peak afforded the desired diastereomer.

Step I: Ester Hydrolysis

To 276 mg (0.853 mmol) of the ester from step H in 10 mL THF:MeOH:water (3:1:1) was added 2 N NaOH (0.64 mL, 1.28 mmol). The solution was stirred at rt for 2 h. The reaction mixture was concentrated and acidified with 2 N HCl (10 mL) and extracted with CHCl₃ (3×20 mL). The combined organic extracts were dried over MgSO₄, filtered, and concentrated to yield the desired carboxylic acid. LCMS (M+H)=310.12

Intermediate IX

3-[(Z)-2-(2-methylcyclopropyl)vinyl]-5-[propyl(methylsulfonyl)amino]benzoic acid (Scheme 6)

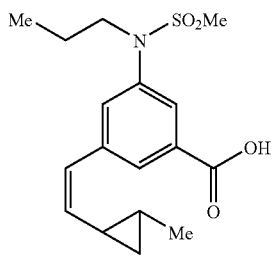

This compound was prepared analogously to 3-[(Z)-2-(2-methylcyclopropyl)vinyl]-5-[methyl(methylsulfonyl)amino]benzoic acid, the only difference being the substitution of methyl iodide with propyl iodide in Step D.

Intermediate X

N-({3-(bromomethyl)-5[(Z)-2(2-methylcyclopropyl)vinyl]phenyl}-N-propylmethanesulfonamide (Scheme 6)

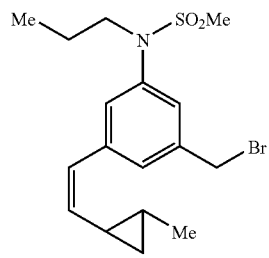

Step A: Acid Reduction

To a solution of 3-[(Z)-2-(2-methylcyclopropyl)vinyl]-5-[propyl(methylsulfonyl)amino]benzoic acid (0.072 g, 0.213 mmol) in 2.5 mL THF was added carbonyldiimidazole (CDI) (0.052 g, 0.320 mmol) in one portion. After 2 h at rt, NaBH₄ (0.024 g, 0.640 mmol) was added in one portion, and the reaction was allowed to proceed at rt for 16 h. Concentrated and partitioned residue between EtOAc and H₂O. Separated, washed aqueous with EtOAc (2×), dried combined organics over Na₂SO₄, filtered and concentrated, and the residue was purified by silica gel chromatography (20-75% EtOAc/hexanes) to afford the desired alcohol as a viscous oil. ¹H NMR (400 MHz, CDCl₃) δ 7.79 (s, 1H), 7.08 (s, 1H), 6.99 (s, 1H), 6.25 (d, J=11.2 Hz, 1H), 5.15 (app t, J=11.2 Hz, 1H), 4.70 (s, 2H), 3.61 (t, J=7.2 Hz, 2H), 2.89 (s, 3H), 1.54-1.43 (m, 3H), 1.06 (d, J=6.0 Hz, 3H), 0.89-0.73 (m, 4H), 0.69-0.57 (m, 2H). LCMS [M+H]⁺=324.

Step B: Bromination

To a solution of alcohol from Step A (0.069 g, 0.213 mmol) and CBr₄ (0.113 g, 0.341 mmol) in 1.0 mL CH₂Cl₂ and 1.0 mL CH₃CN at 0° C. was added Ph₃P (0.090 g, 0.341 mmol) in 0.50 mL CH₂Cl₂ and 0.50 mL CH₃CN via cannula. After 2 h at 0° C., the reaction was quenched by the addition of 0.5 mL MeOH, concentrated, and purified by silica gel chromatography (5->75% EtOAc/hexanes) to afford N-{3-(bromomethyl)-5-[(Z)-2-(2-methylcyclopropyl)vinyl]phenyl}-N-propylmethanesulfonamide as a clear oil. ¹H NMR (400 MHz, CDCl₃) δ 7.37 (s, 1H), 7.31 (s, 1H), 7.19 (s, 1H), 6.24 (d, J=11.5 Hz, 1H), 5.15 (dd, J=11.3, 9.9 Hz, 1H), 4.46 (s, 2H), 3.61 (t, J=7.1 Hz, 2H), 2.87 (s, 3H), 1.54-1.46 (m, 3H), 1.11 (d, J=5.9 Hz, 3H), 0.92-0.88 (m, 4H), 0.68-0.59 (m, 2H). LCMS [M+H]⁺=386, 388 (bromine pattern).

Intermediate XI 3-({2-[(tert-butoxycarbonyl)amino]-2-methyl-3-phenylpropoxy}methyl)-5-[(methylsulfonyl)(propyl)amino]benzoic acid (Scheme 8)

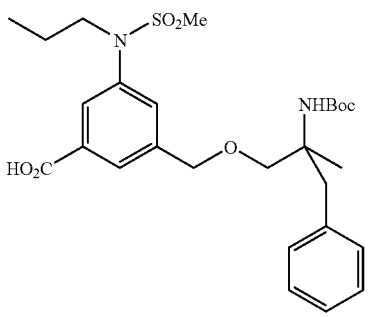

Step A: Reduction

To a solution of: 3-(methoxycarbonyl)-5-[(methylsulfonyl)(propyl)amino]benzoic acid (12.0 g, 38.1 mmol, prepared from dimethyl 5-aminoisophthalate and propyl iodide using a similar procedure as described for the preparation of intermediate A) in THF (250 mL) cooled to 0° C. was added BH$_3$-THF (190.3 mL, 190.3 mmol, 1 M in THF). After 10 min, the reaction mixture was allowed to warm to rt and stirred for 15 h. The reaction mixture was cooled back down to 0° C. and carefully quenched with MeOH. The mixture was concentrated to half its original volume and diluted with EtOAc and water. Following dilution, the organic layer was extracted, washed with sat. aq. NaHCO$_3$ and brine, dried over sodium sulfate and concentrated in vacuo to provide methyl 3-(hydroxymethyl)-5-[(methylsulfonyl)(propyl)amino]benzoate as a yellow oil. $^1$H NMR (400 MHz, CDCl$_3$) δ 8.02 (s, 1H), 7.89 (s, 1H), 7.60 (s, 1H), 4.79 (d, J=5.7 Hz, 2H), 3.94 (s, 3H), 3.67 (t, J=7.2 Hz, 2H), 2.90 (s, 3H), 1.87 (br t, J=5.7 Hz, 1H), 1.55-1.45 (m, 2H), 0.92 (t, J=7.4 Hz, 3H).

Step B: Bromination

To a solution of methyl 3-(hydroxymethyl)-5-[(methylsulfonyl)(propyl)amino]benzoate (2.99 g, 9.92 mmol) in dichloromethane (90 mL) were added carbon tetrabromide (4.28 g, 12.9 mmol) and triphenylphosphine (3.12 g, 11.9 mmol). After 15 h, the reaction mixture was concentrated in vacuo and purified by flash chromatography (silica, 0-40% EtOAc/hexanes) to provide methyl 3-(bromomethyl)-5-[(methylsulfonyl)(propyl)amino]benzoate as a white solid. $^1$H NMR (400 MHz, CDCl$_3$) δ 8.04 (s, 1H), 7.91 (s, 1H), 7.61 (s, 1H), 4.50 (s, 2H), 3.94 (s, 3H), 3.67 (t, J=7.2 Hz, 2H), 2.90 (s, 3H), 1.56-1.46 (m, 2H), 0.92 (t, J=7.3 Hz, 3H).

Step C: Ether Installation

To a solution of tert-butyl (1-benzyl-2-hydroxy-1-methylethyl)carbamate (728 mg, 2.75 mmol) and methyl 3-(bromomethyl)-5-[(methylsulfonyl)(propyl)amino]benzoate (500 mg, 1.37 mmol) in dichloromethane (30 mL) were added silver triflate (423 mg, 1.65 mmol) and 2,6-ditertbutylpyridine polymer bound (1.53 g, 2.75 mmol, loading=1.8 mmol N/g resin, Aldrich 37, 782-1). The reaction mixture was stirred at rt in a sealed flask for 16 h. The reaction mixture was filtered on celite, rinsed with dichloromethane and MeOH, concentrated in vacuo and purified by flash chromatography (silica, 0-45% EtOAc/hexanes) to provide methyl 3-({2-[(tert-butoxycarbonyl)amino]-2-methyl-3-phenylpropoxy}methyl)-5-[(methylsulfonyl)(propyl)amino]benzoate as a white foam (intermediate xx). $^1$H NMR (400 MHz, CDCl$_3$) δ 7.99 (s, 1H), 7.92 (s, 1H), 7.57 (s, 1H), 7.30-7.20 (m, 3H), 7.18-7.7.14 (m, 2H) 4.60 (s, 2H), 4.56 (s, 1H), 3.95 (s, 3H), 3.68 (t, J=6.7 Hz, 2H), 3.57 (A of AB, d, J=8.9 Hz, 1H), 3.47 (B of AB, d, J=8.9 Hz, 1H), 3.15 (A of AB, d, J=13.2 Hz, 1H), 2.94 (B of AB, d, J=13.2 Hz, 1H), 2.90 (s, 3H), 1.55-1.45 (m, 2H), 1.47 (s, 9H), 1.27 (s, 3H), 0.92 (t, J=7.3 Hz, 3H).

Step D: Saponification

To a solution of methyl 3-({2-[(tert-butoxycarbonyl)amino]-2-methyl-3-phenylpropoxy}methyl)-5-[(methylsulfonyl)(propyl)amino]benzoate (462 mg, 0.842 mmol) in THF (15 mL) was added aq. LiOH (4.21 mL, 4.21 mmol, 1N). After stirring vigorously at rt for 20 h, the reaction mixture was acidified to pH 4 with HCl (4.07 nL, 4.07 mmol, 1N), extracted with dichloromethane, dried over sodium sulfate and concentrated in vacuo to provide 3-({2-[(tert-butoxycarbonyl)amino]-2-methyl-3-phenylpropoxy}methyl)-5-[(methylsulfonyl)(propyl)amino]benzoic acid as a white foam. $^1$H NMR (400 MHz, CDCl$_3$) δ 8.05 (s, 1H), 7.96 (s, 1H), 7.61 (s, 1H), 7.30-7.20 (m, 3H), 7.18-7.13 (m, 2H) 4.66-4.57 (m, 3H), 3.68 (t, J=7.2 Hz, 2H), 3.59 (A of AB, br d, J=8.5 Hz, 1H), 3.49 (B of AB, br d, J=8.5 Hz, 1H), 3.15 (A of AB, d, J=13.3 Hz, 1H), 2.93 (B of AB, d, J=13.3 Hz, 1H), 2.91 (s, 3H), 1.57-1.45 (m, 2H), 1.47 (s, 9H), 1.27 (s, 3H), 0.92 (t, J=7.4 Hz, 3H).

Intermediate XII

N-[3-[(2-amino-2-methyl-3-phenylpropoxy)methyl]-5-(bromomethyl)phenyl]-N-propylmethanesulfonamide

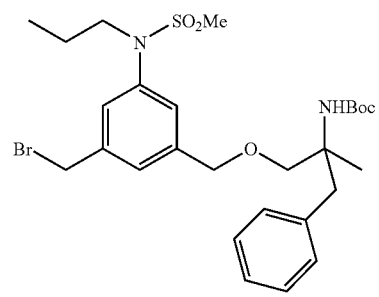

Step A: Reduction

To a solution of 3({2-[(tert-butoxycarbonyl)amino]-2-methyl-3-phenylpropoxy}methyl)-5-[(methylsulfonyl)(propyl)amino]benzoic acid (intermediate XI, 145 mg, 0.271 mmol) in THF (2 mL) cooled to 0° C. was added BH$_3$-THF (1.356 mL, 1.356 mmol, 1 M in THP). After 10 min, the reaction mixture was allowed to warm to rt and stirred for 60 h. The reaction mixture was cooled back down to 0° C. and carefully quenched with MeOH. The mixture was concentrated to half its original volume and diluted with EtOAc and water. Following dilution, the organic layer was extracted, washed with sat. aq. NaHCO$_3$ and brine, dried over sodium sulfate and concentrated in vacuo to provide N-[3-[(2-amino-2-methyl-3-phenylpropoxy)methyl]-5-(hydroxymethyl)phenyl]-N-propylmethanesulfonamide as a white foam. $^1$H NMR (400 MHz, CDCl$_3$) δ 7.33 (s, 1H), 7.29 (s, 1H), 7.28-7.20 (m, 4H), 7.17-7.13 (m, 2H), 4.74 (s, 2H), 4.60-4.51 (m, 3H), 3.63 (t, J=7.2 Hz, 2H), 3.53 (A of AB, d, J=8.8 Hz, 1H), 3.43 (B of AB, d, J=8.8 Hz, 1H), 3.12 (A of AB, d, J=13.2 Hz, 1H), 2.93 (B of AB, d, J=13.2 Hz, 1H), 2.88 (s, 3H), 1.55-1.45 (m, 2H), 1.46 (s, 9H), 1.25 (s, 3H), 0.91 (t, J=7.3 Hz, 3H).

Step B: Bromination

To a solution of methyl N-[3-[(2-amino-2-methyl-3-phenylpropoxy)methyl]-5-(hydroxymethyl)phenyl]-N-propyl-methanesulfonamide (140 mg, 0.269 mmol) in dichloromethane (2.5 mL) were added carbon tetrabromide (116 mg, 0.350 mmol) and triphenylphosphine (85.0 mg, 0.323 mmol). After 15 h, the reaction mixture was concentrated in vacuo and purified by flash chromatography (silica, 0-35% EtOAc/hexanes) to provide N-[3-[(2-amino-2-methyl-3-phenylpropoxy)methyl]-5-(bromomethyl)phenyl]-N-propylmethanesulfonamide as a colorless oil. $^1$H NMR (400 MHz, CDCl$_3$) δ 7.34 (s, 1H), 7.31 (s, 1H),), 7.30-7.20 (m, 4H), 7.18-7.14 (m, 2H), 4.60-4.50 (m, 3H), 4.49 (s, 2H), 3.64 (t, J=7.2 Hz, 2H), 3.55 (A of AB, d, J=8.7 Hz, 1H), 3.45 (B of AB, d, J=8.7 Hz, 1H), 3.14 (A of AB, d, J=13.3 Hz, 1H), 2.94 (B of AB, d, J=13.3 Hz, 1H), 2.88 (s, 3H), 1.56-1.47 (m, 2H), 1.46 (s, 9H), 1.27 (s, 3H), 0.91 (t, J=7.4 Hz, 3H).

Intermediate XIII (R)-2 (1-methylbut-2-yn-1-yl)amine

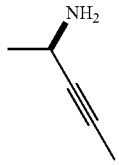

Step A: Auxiliary Installation

To a solution of acetaldehyde (2.8 g, 64.36 mmol) and (R)(+)-2-Methyl-2-propane sulfinamide (3.9 g, 32.18 mmol) in methylene chloride (20 mL) at rt was added powdered anhydrous magnesium sulfate (19 g, 160 mmol). The resultant slurry was stirred overnight at ambient temperature. The reaction was diluted with methylene chloride (200 mL) and filtered and the solids washed with another 100 mL portion of methylene chloride. The filtrate was concentrated at reduced pressure to give the product as an oil. $^1$H NMR (400 MHz, CDCL$_3$) δ 8.08 (q, J=5.1 Hz, 1H), 2.24 (d, J=5.1 Hz, 3H), 1.19 (s, 9H). LCMS [(M)+H]$^+$=150.

Step B: Grignard Addition

To a solution of the product of Step A above (400 mg, 2.72 mmol) in methylene chloride at 0° C. was added a solution of 1-propynyl magnesium bromide (6 mL of 0.5 N in THF) The reaction was warmed to rt and poured into water (100 mL) and extracted with ethyl acetate (2×100 nL). The combined organics were washed with brine (50 mL), dried over anhydrous sodium sulfate, filtered and concentrated at reduced pressure. The residue was chromatographed on silica gel eluting with a gradient of 50% to 75% Ethyl acetate/hexanes to give 2-methyl-N-(1-methylbut-2-yn-1-yl)propane-2-sulfinamide (280 mg) as a gummy solid. $^1$H NMR (400 MHz, CDCL$_3$) δ 4.13 (m, 1H), 3.33 (m, 1H), 1.82 (s, 3H), 1.40 (d, J=6.7 Hz, 3H), 1.21, (s, 9H) LCMS [(M)+H]$^+$=188.

Step C: Auxiliary Removal

To a solution of 2-methyl-N-(1-methylbut-2-yn-1-yl)propane-2-sulfinamide (310 mg, 1.65 mmol) in methanol (5 mL) at rt was added a solution of HCl in dioxane (8 mL of 4N HCl in dioxane, 32 mmol) and the solution allowed to stand for 1 h at rt. The solvent was then evaporated at reduced pressure to give a quantitative yield of (R)-2 (1-methylbut-2-yn-1-yl)amine hydrochloride. $^1$H NMR (400 MHz, CD$_3$OD) δ 4.15-4.17 (m, 1H), 1.86 (d, J=2.3 Hz, 3H), 1.49, (d, J=6.8 Hz, 3H). LCMS [(M)+H]$^+$=84.

Intermediate XIV 3-(bromomethyl)-N-[(1R)-1-(4-fluorophenyl)ethyl]-5-[propyl(methylsulfonyl)amino]benzamide
(Scheme 2)

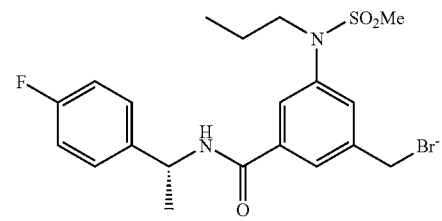

Prepared from 5-aminoisophthalate, methanesulfonyl chloride and n-propyl iodide following a similar procedure as described for the preparation of intermediate III.

Intermediate XV

Ethyl 3-(bromomethyl)-5-(1-cyanocyclopentyl)benzoate

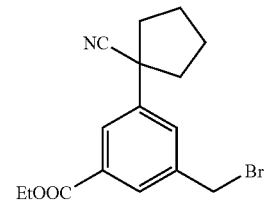

Step A: Bromination

To a solution of diethyl 5-(hydroxymethyl)benzene-1,3-dioate (3.5 g, 0.014 mol) and carbon tetrabromide (5.0 g, 0.015 mol) in 30 mL CH$_2$Cl$_2$, cooled to 0° C., was added dropwise a solution of triphenylphosphine (3.9 g, 0.015 mol) in 20 mL CH$_2$Cl$_2$. The reaction was stirred at 0° C. for 1.5 h, diluted with CHCl$_3$, and washed with water and brine. Drying, solvent evaporation and flash chromatography (silica gel, 0-30% EtOAc/hexanes) gave diethyl-5-(bromomethyl)benzene-1,3-dioate. $^1$H NMR (400 MHz, CDCl$_3$) δ 8.61 (s, 1H), 8.25 (app d, J=1.6 Hz, 2H), 4.55 (s, 2H), 4.42 (q, J=7.1 Hz, 4H), 1.42 (t, J=7.1 Hz, 6H).

Step B: Cyanation

To a solution of diethyl-5-(bromomethyl)benzene-1,3-dioate (1.9 g, 6.0 mmol) in 69 mL MeCN was added trimethylsilyl cyanide (1.2 mL, 9.0 mmol) and tetrabutylammonium fluoride (1M in THF, 9.0 mL, 9.0 mmol). The reaction was stirred for 0.5 h and concentrated. Flash chromatography (silica gel, 0-30% EtOAc/hexanes) gave diethyl 5-(cyanomethyl)benzene-1,3-dioate. ¹H NMR (400 MHz, CDCl₃) δ 8.65 (s, 1H), 8.20 (app t, J=0.7 Hz, 2H), 4.43 (q, J=7.1 Hz, 4H), 3.86 (s, 2H), 1.43 (t, J=7.1 Hz, 6H).

Step C: Alkylation

To a solution of diethyl 5-(cyanomethyl)benzene-1,3-dioate (500 mg, 1.9 mmol) in 18.6 mL THF was added potassium bis(trimethylsilyl)amide (1.1 g, 5.7 mmol) and the reaction was stirred at rt for 5 min. 1,4-Dibromobutane (0.25 mL, 2.1 mmol) was added, the mixture was stirred for 45 min and then quenched with 1N HCl. Ethyl acetate was added, the layers separated and the organic layer was washed with water and brine. Drying, solvent evaporation and flash chromatography (silica gel, 0-15% EtOAc/hexanes) gave diethyl 5-(1-cyanocyclopentyl)benzene-1,3-dioate. ¹H NMR (400 MHz, CDCl₃) δ 8.63 (m, 1H), 8.31 (m, 2H), 4.43 (q, J=7.1 Hz, 4H), 2.56 (m, 2H), 2.14-1.99 (m, 6H), 1.43 (t, J=7.1 Hz, 6H).

Step D: Ester Hydrolysis

A solution of diethyl 5-(1-cyanocyclopentyl)benzene-1,3-dioate (0.33 g, 1.05 mmol) and NaOH (1N in H₂O, 0.945 mL, 0.945 mmol) in 5 mL THF and 5 mL EtOH was stirred at rt overnight. The reaction mixture was concentrated, diluted with H₂O and extracted with ether. The aqueous phase was made acidic with 1N HCl, extracted with EtOAc and the combined organic layers were washed with brine. Drying and solvent evaporation gave 3-(ethoxycarbonyl)-5-(1-cyanocyclopentyl)benzoic acid. ¹H NMR (400 MHz, CD₃OD) δ 8.58 (m, 1H), 8.35 (m, 2H), 4.43 (q, J=7.1 Hz, 2H), 2.51 (m, 2H), 2.18 (m, 2H), 2.05 (m, 4H), 1.42 (t, J=7.1 Hz, 3H).

Step E: Acid Reduction and Bromination

To a solution of 3-(ethoxycarbonyl)-5-(1-cyanocyclopentyl)benzoic acid (0.4 g, 1.4 mmol) in 14 mL THF, cooled to 0° C., was added borane-tetrahydrofuran complex (1M in THF, 5.6 mL, 5.6 mmol) dropwise. The reaction was stirred at 0° C. for 1.5 h and then at rt for 3.5 h. The mixture was quenched with MeOH, concentrated, diluted with EtOAc and washed with water and brine. Drying and solvent evaporation gave ethyl 3-(1-(aminomethyl)cyclopentyl)-5-(hydroxymethyl)benzoate and ethyl 3-(1-cyanocyclopentyl)-5-(hydroxymethyl)benzoate. The crude mixture was dissolved in 6.6 mL CH₂Cl₂, cooled to 0° C. and treated with carbon tetrabromide (0.56 g, 1.7 mmol). A solution of triphenylphosphine (0.42 g, 1.6 mmol) in 6.6 mL CH₂Cl₂ was added and the reaction was stirred at 0° C. for 1 h. Concentration and flash chromatography (silica gel, 0-20% EtOAc/hexanes) gave ethyl 3-(bromomethyl)-5-(1-cyanocyclopentyl)benzoate. ¹H NMR (400 MHz, CDCl₃) δ 8.02 (t, J=1.9 Hz, 2H), 7.70 (t, J=1.7 Hz, 1H), 4.52 (s, 2H), 4.41 (q, J=7.1 Hz, 2H), 2.53 (m, 2H), 2.12-1.97 (m, 6H), 1.41 (t, J=7.1 Hz, 3H).

Intermediate XVI

Ethyl 3-((2-tert-butoxycarbonylamino-2-methyl-3-phenylpropoxy)methyl)-5-(1-cyanocyclopentyl)benzoate

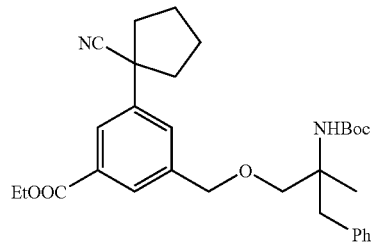

To a solution of ethyl 3-(bromomethyl)-5-(1-cyanocyclopentyl)benzoate (0.15 g, 0.45 mmol) and 2-tert-butoxycarbonylamino-2-methyl-3-phenylpropan-1-ol (0.21 g, 0.79 mmol in 8 mL dichloroethane was added 2,6-di-tert-butylpyridine, polymer bound (0.72 g, 1.3 mmol) and silver trifluoromethanesulfonate (0.20 g, 0.79 mmol). The reaction was stirred at rt overnight and filtered. Concentration and flash chromatography (silica gel, 0-25% EtOAc/hexanes) gave ethyl 3-((2-tert-butoxycarbonylamino-2-methyl-3-phenylpropoxy)methyl)-5-(1-cyanocyclopentyl)benzoate. ¹H NMR (400 MHz, CDCl₃) δ 8.03 (app d, J=1.5 Hz, 1H), 7.96 (s, 1H), 7.67 (s, 1H), 7.28-7.22 (m, 3H), 7.17 (m, 2H), 4.60 (s, 2H), 4.57 (s, 1H), 4.40 (q, J=7.1 Hz, 2H), 3.55 (d, J=8.9 Hz, 1H), 3.45 (d, J=9.0 Hz, 1H), 3.14 (d, J=13.3 Hz, 1H), 2.95 (d, J=13.2 Hz, 1H), 2.52 (m, 2H), 2.13-1.96 (m, 6H), 1.46 (s, 9H), 1.41 (t, J=7.1 Hz, 3H), 1.28 (s, 3H).

Intermediate XVII 3-((2-tert-Butoxycarbonylamino-2-methyl-3-phenylpropoxy)methyl)-5-(1-cyanocyclopentyl)benzoic acid

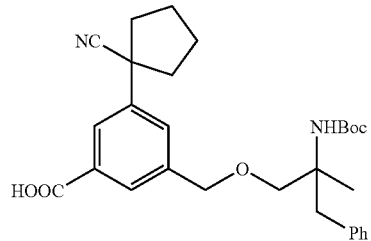

A solution of ethyl 3-((2-tert-butoxycarbonylamino-2-methyl-3-phenylpropoxy)methyl)-5-(1-cyanocyclopentyl)benzoate (0.13 g, 0.25 mmol) and LiOH.H₂O (31 mg, 0.75 mmol) in 6.5 mL THF and 2.5 mL H₂O was stirred at rt overnight. Additional LiOH.H₂O (25 mg, 0.60 mmol) was added and the reaction was continued for 64 h. The mixture was concentrated, diluted with H₂O, made acidic with 10% citric acid solution and extracted with EtOAc. The combined organic layers were washed with brine. Drying and solvent evaporation gave 3-((2-tert-butoxycarbonylamino-2-methyl-3-phenylpropoxy)methyl)-5-(1-cyanocyclopentyl)benzoic acid. ¹H NMR (500 MHz, CDCl₃) δ 8.09 (app d, J=1.5 Hz, 1H), 8.04 (s, 1H), 7.74 (s, 1H), 7.28-7.20 (m, 3H), 7.17

(m, 2H), 4.62 (s, 3H), 3.58 (bs, 1H), 3.48 (d, J=8.5 Hz, 1H), 3.15 (d, J=12.9 Hz, 1H), 2.95 (d, J=13.2 Hz, 1H), 2.54 (m, 2H), 2.14-1.96 (m, 6H), 1.47 (s, 9H), 1.28 (s, 3H).

Intermediate XVIII

2-Amino-2-(difluoromethyl)-3-phenylpropan-1-ol

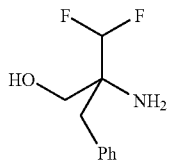

To a solution of methyl 2-amino-2-benzyl-3,3-difluoropropanoate (0.11 g, 0.48 mmol) (for synthesis see: Bey et al, *J. Org. Chem.* 1979, 44, 2732-2742) in 6.8 mL THF was added lithium borohydride (2M in THF, 1.45 mL, 2.9 mmol) dropwise. The reaction was heated at reflux temperature for 2 h, quenched with MeOH and acetone and concentrated. Hydrochloric acid (1M, 14.5 mL, 14.5 mmol) was added, the mixture was heated to 45° C. for 1.5 h and concentrated. The reaction was made basic with saturated NaHCO$_3$ and extracted with CHCl$_3$. Drying and solvent evaporation gave 2-amino-2-(difluoromethyl)-3-phenylpropan-1-ol. $^1$H NMR (400 MHz, CDCl$_3$) δ 7.35-7.24 (m, 5H), 5.67 (t, J=56.5 Hz, 1H), 3.56 (A of AB, d, J=11.0 Hz, 1H), 3.46 (B of AB, d, J=11.0 Hz, 1H), 2.89 (A of AB, d, J=13.6 Hz, 1H), 2.84 (B of AB, d, J=13.6 Hz, 1H).

Intermediate XIX

2-Amino-2-(fluoromethyl)-3-phenylpropan-1-ol

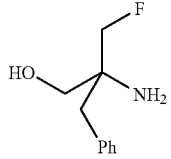

To a suspension of 2-amino-2-benzyl-3-fluoropropanoic acid (50 mg, 0.25 mmol) (for synthesis see EP 0 040 150 A1) in 2.5 mL THF, cooled to 0° C., was added borane-tetrahydrofuran complex (1M in THF, 0.75 mL, 0.75 mmol) dropwise. The reaction was stirred at rt overnight, quenched with MeOH and concentrated. Hydrochloric acid (1M, 7.5 mL, 7.5 mmol) was added, the mixture was heated to 45° C. for 1 h and concentrated. The reaction was made basic with saturated NaHCO$_3$ and exacted with CHCl$_3$. Drying and solvent evaporation gave 2-amino-2-(fluoromethyl)-3-phenylpropan-1-ol. $^1$H NMR (400 MHz, CDCl$_3$) δ 7.35-7.21 (m, 5H), 4.30-4.11 (two q, ABX system, J=47.4 Hz, J=20.8 Hz, J=9.0 Hz, 2H), 3.49 (m, 2H), 2.76 (m, 2H).

Intermediate XX

2-{[(2-methylcyclopropyl)methyl]amino}-6-[methyl(methylsulfonyl)amino]isonicotinic acid (Schemes 4 and 10)

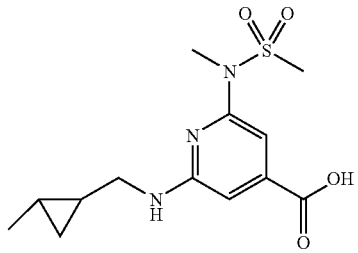

Step A: Sulfonamide Incorporation

Methyl 2,6-dichloroisonicotinate (5.0 g, 24.3 mmol), methyl(methylsulfonyl)amine (3.18 g, 29.12 mmol), potassium phosphate (7.22 g, 34.0 mmol), Xantphos (0.87 g, 1.50 mmol) and tris(dibenzylideneacetone)dipalladium (0.68 g, 0.51 mmol) were added to a dry, argon flushed flask. Dioxane (195 mL) was added, the solution degassed with argon and the reaction was heated to 100° C. for 16 h. The reaction was cooled to rt, filtered through celite and evaporated in vacuo. Flash chromatography (silica, 0-50% EtOAc/CH$_2$Cl$_2$) gave methyl 2-chloro-6-[methyl(methylsulfonyl)amino]isonicotinate as a yellow oil: $^1$H NMR (400 MHz, CDCl$_3$) δ 7.88 (s, 1H), 7.68 (s, 1H), 3.96 (s, 3H), 3.44 (s, 3H), 3.11 (s, 3H).

Step B: Amination

A solution of methyl 2-chloro-6-[methyl(methylsulfonyl)amino]isonicotinate (1.2 g, 4.30 mmol), amine intermediate V (1.0 g, 5.60 mmol), potassium phosphate (2.74 g, 12.9 mmol), and palladium bis(tri-t-butylphosphine) (0.11 g, 0.22 mmol) in degassed toluene (15 mL) was sealed in a glass tube and heated to 110° C. for 16 h. The reaction was filtered through celite, rinsed with ethyl acetate and concentrated in vacuo. Flash chromatography (silica, 20% EtOAc/hexanes) gave methyl 2-{benzyl[(2-trans-methylcyclopropyl)methyl]amino}-6-[methyl(methylsulfonyl)amino]isonicotinate: $^1$H NMR (400 MHz, MeOD) δ 7.28 (m, 5H), 7.01 (d, J=0.8 Hz, 1H), 6.98 (d, J=0.8 Hz, 1H), 4.83 (s, 2H), 3.87 (s, 3H), 3.62 (dd, J=6.0, 14.8 Hz, 1H), 3.30 (dd, J=7.2, 14.8 Hz, 1H), 3.23 (s, 3H), 2.88 (s, 3H), 0.93 (d, J=6.0 Hz, 3H), 0.81 (m, 1H), 0.62 (m, 1H), 0.39 (m, 1H), 0.22 (m, 1H)

Step C: Hydrogenation

A solution of 2-{benzyl[(2-methylcyclopropyl)methyl]amino}-6-[methyl(methylsulfonyl)amino]isonicotinate (0.93 g, 2.23 mmol), 20% palladium hydroxide on carbon (0.042 g, 0.06 mmol) and trifluoroacetic acid (0.13 g, 1.11 mmol) in ethanol (10 mL) was placed under a hydrogen atmosphere and heated to 60° C. for 3 h. The reaction was cooled to ambient temperature, filtered over celite, rinsed with methanol and evaporated in vacuo to give methyl 2-{[(2-trans-methylcyclopropyl)methyl]amino}-6-[methyl(methylsulfonyl)amino)isonicotinate: LC-MS [M+H]=328.1

Step D: Saponification

A solution of methyl 2-{[(2-trans-methylcyclopropyl)methyl]amino}-6-[methyl(methylsulfonyl)amino)isonicotinate (0.8 g, 2.44 mmol) in methanol (5 mL) and tetrahydrofuran (5 mL) was treated with 1N NaOH (4.9 mL, 4.9 mmol) and the reaction was heated to 50° C. for 1 h. The reaction was evaporated in vacuo and partitioned between 1M HCl and ethyl acetate. The combined organics were dried over sodium sulfate, filtered and evaporated in vacuo to give 2-{[(2-methylcyclopropyl)methyl]amino}-6-[methyl(methylsulfonyl)amino]isonicotinic acid as a white solid: $^1$H NMR (400 MHz, CD$_3$OD) δ 6.89 (s, 1H), 6.83 (s, 1H), 3.30 (s, 3H), 3.17 (d, J=6.8 Hz, 2H), 3.15 (s, 3H), 1.03 (d, J=6.0 Hz, 3H), 0.81 (m, 1H), 0.64 (m, 1H), 0.39 (m, 1H), 0.22 (m, 2H); HRMS (ES, M+H) calcd. for C$_{13}$H$_{19}$N$_3$O$_4$S: 314.1169, found: 314.1171.

Intermediate XXI

2-[(Isopropylsulfonyl)(methyl)amino]-6-{[(2-methylcyclopropyl)methyl]amino}isonicotinic acid
(Schemes 4 and 10)

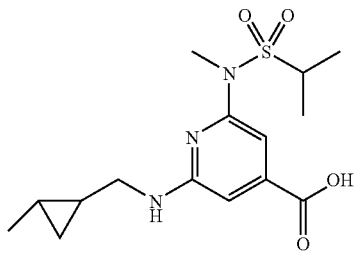

Prepared in manner similar to Intermediate XX using methyl(isopropylsulfonyl)amine: $^1$H NMR (400 MHz, CD$_3$OD) δ 6.90 (d, J=1.2 Hz, 1H), 6.82 (d, J=1.2 Hz, 1H), 4.05 (sept, J=6.8 Hz, 1H), 3.38 (s, 3H), 3.17 (AB of ABX$_2$, J$_{AX}$, J$_{BX}$=6.8 Hz, J$_{AB}$=13.6, 2H), 1.34 (d, J=6.8 Hz, 6H), 1.04 (d, J=6.0 Hz, 3H), 0.83 (m, 1H), 0.65 (m, 1H), 0.39 (m, 1H), 0.23 (m, 1H); LC-MS [M+H]=342.1.

Intermediate XXII tert-butyl (2-amino-1-benzyl-1-methylethyl)carbamate
(Scheme 10)

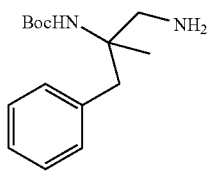

Step A: Boc Protection

In a flask α-methyl-dl-phenylalanine methyl ester hydrochloride (5.1 g, 22 mmol) in THF (75 mL) at rt was added TEA (2.9 mL, 22 mmol). The contents were filtered (remove TEA-HCl) and the filtrate treated with t-butoxycarbonyl anhydride (4.8 g, 22 mmol). The mixture was placed in 50° oil bath and stirred overnight. The crude mixture was poured onto EtOAc and washed with aq. NH$_4$Cl followed by water and brine. After drying over Na$_2$SO$_4$ and solvent removal, 6.6 g methyl methyl N-(tert-butoxycarbonyl)-α-methylphenylalaninate was obtained as a white solid (quant): $^1$H NMR (400 MHz, CD$_3$OD) δ 7.34 (m, 3H), 7.05 (m, 2H), 5.12 (br s, 1H), 3.74 (s, 3H), 3.34 (broad AB, J=9.6 Hz, 1H), 3.18 (AB, J=13.6 Hz, 1H), 1.55 (s, 3H), 1.45 (s, 9H); LC-MS [M-99, loss of Boc]=194.3.

Step B: Reduction

In a flask containing methyl N-(tert-butoxycarbonyl)-α-methylphenylalaninate (6.5 g, 22.1 mmol) in methylene chloride 80 mL at −78° C. was added dropwise di-iso-butyl aluminum hydride (1M toluene solution, 22 mL, 22 mmol) over 20 min. The reaction was maintained at or below −70° C. for 2 h, then warmed to rt for 1 h, re-cooled to 0° C. and quenched with 100 mL 1N HCl. The product was extracted repeatedly with methylene chloride, the organic layers combined, washed with brine, and dried over Na$_2$SO$_4$. Upon solvent removal under reduced pressure 5.8 g of methyl tert-butyl (1-benzyl-2-hydroxy-1-methylethyl)carbamate was obtained (99%): LC-MS [M-99, loss of Boc]=166.3.

Step C: Oxidation

In a flask containing above intermediate from step B methyl tert-butyl (1-benzyl-2-hydroxy-1-methylethyl)carbamate (3.6 g, 13.5 mmol) in DCM (50 mL) and DMSO (113 mL) at 0° C. was added SO$_3$-pyridine (5.4 g, 13.6 mmol). The mixture was warmed to rt and stirred for 5 h. Dilute with EtOAc, wash organic layer successively with H$_2$O (100 mL), 10% aq. KHSO4, aq. NaHCO$_3$, 3M aq. LiCl followed by brine. Upon drying over Na$_2$SO4 and solvent removal 3 g of crude was obtained. Purification via flash chromatography on silica gel (25% EtOAc/hexanes) afforded 1.7 g final tert-butyl (1-benzyl-1-methyl-2-oxoethyl)carbamate (48%): LC-MS [M-99, loss of Boc]=164.2.

Step D: Reductive Alkylation

In a 100 mL flask intermediate from step C tert-butyl (1-benzyl-1-methyl-2-oxoethyl)carbamate (1.7 g, 6.5 mmol), and benzyl amine (0.7 g, 6.5 mmol) were dissolved in DCE (25 mL). NaHB(OAc)$_3$ (2.1 g, 9.7 mmol) was added as a solid in portions. The reaction was allowed to stir at rt for 48 h, diluted with aq. NaHCO$_3$, concentrated to ½ volume and extracted with EtOAc (2×20 nL). The combined organic layers were washed with brine, dried over Na$_2$SO$_4$ and concentrated to dryness to give 2.4 g crude product. SCX ion exchange chromatography was performed to give 610 mg clear oil identified as desired product, tert-butyl [1-benzyl-2-(benzylamino)-1-methylethyl]carbamate (27%): LC-MS [M+H]=355.2.

Step E: Benzyl Removal

To an argon purged EtOH solution containing tert-butyl [1-benzyl-2-(benzylamino)-1-methylethyl]carbamate (600 mg, 1.7 mmol), intermediate from step D above, was added 20% Pd(OH)$_2$ (12 mg, 0.1 mmol). H$_2$ (g) was bubbled through the mixt. using a needle attached to a balloon from 15 min. The mixture was maintained under an H$_2$ atmosphere, placed in a 60° C. oil bath and stirred for 16 h. The mixture was cooled to rt and additional catalyst and TFA (193 mg, 1.7 mmol) added. After heating further for 48 h the reaction was filtered over Celite, concentrated to dryness and purified by RP-HPLC to give desired intermediate tert-butyl (2-amino-1-benzyl-1-methylethyl)carbamate: $^1$H NMR (400 MHz, CD$_3$OD) δ 7.34 (m, 3H), 7.18 (m, 2H), 3.63 (d, J=12.8 Hz, 1H), 3.31 (overlapping d with CHD$_2$OH), 1H), 2.99 (d, J=12.8 Hz, 1H), 2.66 (d, J=13.2 Hz, 1H), 1.50 (s, 9H), 1.11 (s, 3H); LC-MS [M+H]=265.3.

EXAMPLE 1

3-[(2-amino-2-methyl-3-phenylpropoxy)methyl]-N-[(1R)-1-(4-fluorophenyl)ethyl]-[methyl(methylsulfonyl)amino]benzamide (Scheme 2)

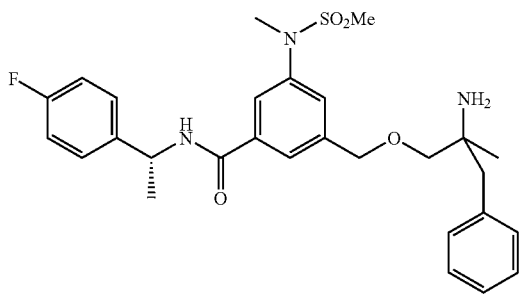

To a solution of 2-amino-2-methyl-3-phenylpropan-1-ol I (28 mg, 0.17 mmol) in 0.5 nL DMF cooled to 0° C. was added sodium hexamethyldisylazide (0.17 mL, 0.17 mmol, 1 M in THF). The reaction mixture was stirred at 0° C. for 5 min and intermediate III 3-(bromomethyl)-N-[(1R)-1-(4-fluorophenyl)ethyl]-5-[methyl(methylsulfonyl)amino]benzamide (25 mg, 0.06 mmol) in 0.5 mL DMF was added dropwise. The reaction mixture was stirred at 0° C. for 0.5 h and purified by preparative HPLC (5%->95% CH$_3$CN in water containing 0.1% TFA, C18 PRO YMC 20×150 mm) to afford 3-[(2-amino-2-methyl-3-phenylpropoxy)methyl]-N-[(1R)-1-(4-fluorophenyl)ethyl]-5-[methyl(methylsulfonyl)amino]benzamide. $^1$H NMR (400 MHz, d$_4$-MeOH) δ 8.87 (d, J=8 Hz, 1H), 7.86-7.80 (m, 2H), 7.66 (s, 1H), 7.45-7.40 (m, 2H), 7.36-7.24 (m, 3H), 7.22-7.16 (m, 2H), 7.10-7.02 (m, 2H), 5.30-5.20 (m, 1H), 4.73-4.64 (m, 2H), 3.44 (A of AB, d, J=10 Hz, 1H), 3.39 (B of AB, d, J=10 Hz, 1H), 3.35 (s, 3H), 3.09 (A of AB, d, J=13.2 Hz, 1H), 2.94 (s, 3H), 2.87 (B of AB, d, J=13.2 Hz, 1H), 1.59 (d, J=7.2 Hz, 3H), 1.25 (s, 3H).

EXAMPLE 2

3-{[(2-amino-2-benzylpent-4-en-1-yl)oxy]methyl}-N-[(1R)-1-(4-fluorophenyl)ethyl]-5-methyl(methylsulfonyl)amino]benzamide (Scheme 2)

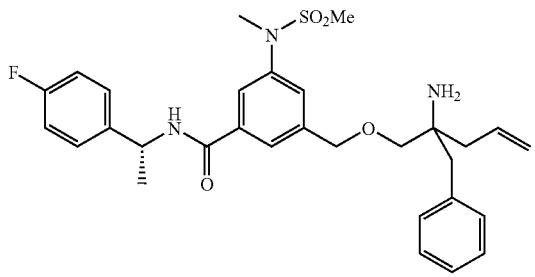

To a solution of 2-amino-2-benzylpent-4-en-1-ol hydrochloride (0.031 mg, 0.135 mmol) (for synthesis of amino alcohol, see: Kaptein et al, *Tetrahedron Lett.* 1994, 35, 1777-1780 and references cited therein) in 0.50 mL DMF cooled to 0° C. was added sodium hexamethyldisylazide (0.271 mL, 0.271 mmol, 1 M in THF). The reaction mixture was stirred at 0° C. for 15 min and intermediate A 3-(bromomethyl)-N-[(1R)-1-(4-fluorophenyl)ethyl]-5-[methyl(methylsulfonyl)amino]benzamide (0.040 g, 0.090 mmol) in 0.50 mL DMF was added dropwise. The reaction mixture was stirred at 0° C. for 2 h, quenched with methanol, concentrated in vacuo, redissolved in 0.55 mL DMF and purified by preparative HPLC (5->95% CH$_3$CN/H$_2$O, 0.1% added TFA, C18 PRO YMC 20×150 mm) to afford 3-{[(2-amino-2-benzylpent-4-en-1-yl)oxy]methyl}-N-[(1R)-1-(4-fluorophenyl)ethyl]-5-[methyl(methyl sulfonyl)amino]benzamide as its trifluroacetate salt. $^1$H NMR (400 MHz, d$_4$-MeOH) δ 8.87 (d, J=7.5 Hz, 1H), 7.82 (s, 1H), 7.80 (s, 1H), 7.63 (s, 1H), 7.41 (m, 2H), 7.32-7.26 (m, 3H), 7.19 (m, 2H), 7.03 (m, 2H), 5.85 (m, 1H), 5.30-5.20 (m, 3H), 6.27 (d, J=12.5 Hz, 1H), 4.63 (d, J=12.5 Hz, 1H), 3.49 (d, J=10.1 Hz, 1H) 3.43 (d, J=10.1 Hz, 1H), 3.34 (s, 3H), 3.06 (d, J=13.7 Hz, 1H), 2.93 (d, J=13.7 Hz, 1H), 2.91 (s, 3H), 2.42 (dd, J=7.5, 6.8 Hz, 1H), 2.34 (dd, J=7.5, 7.2 Hz, 1H), 1.56 (d, J=7.0 Hz). LCMS M+H=554.

EXAMPLE 3

3-{[(2-amino-2-benzylpentyl)oxy]methyl}-N-[(1R)-1-(4-fluorophenyl)ethyl]-5-[methyl(methylsulfonyl)amino]benzamide (Scheme 2)

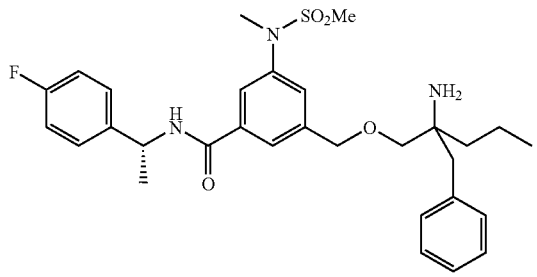

To a solution of 3-{[(2-amino-2-benzylpent-4-en-1-yl)oxy]methyl}-N-[(1R)-1-(4-fluorophenyl)ethyl]-5-[methyl(methyl sulfonyl)amino]benzamide (0.004 g, 0.006 mmol) in 1 mL EtOH was added a spatula tip of Pd/C. The reaction vessel was then evacuated and opened to a balloon of H$_2$ (3×), and stirred under an atmosphere of H$_2$ for 2 h. The reaction vessel was then evacuated and opened to N$_2$ (3×) and filtered through a pad of celite, rinsing with EtOAc. After the volatiles were removed in vacuo, the remaining residue was redissolved in 0.55 mL DMF and purified by preparative HPLC (5->95% CH$_3$CN/H$_2$O, 0.1% added TFA, C18 PRO YMC 20×50 mm) to afford 3-{[(2-amino-2-benzylpentyl)oxy]methyl}-N-[(1R)-1-(4-fluorophenyl)ethyl]-5-[methyl(methyl sulfonyl)amino]benzamide as its trifluroacetate salt. $^1$H NMR (400 MHz, d$_4$-MeOH) δ 8.86 (d, J=7.3 Hz, 1H), 7.82 (s, 1H), 7.80 1H), 7.63 (s, 1H), 7.42-7.39 (m, 2H), 7.33-7.28 (m, 3H), 7.16 (m, 2H), 7.03 (m, 2H), 5.23 (m, 1H), 4.65 (s, 2H), 3.50 (d, J=10.0 Hz, 1H), 3.42 (d, J=10.0 Hz, 1H), 3.34 (s, 3H), 3.03 (d, J=13.7 Hz, 1H), 2.93 (d, J=13.7 Hz, 1H), 2.91 (s, 3H), 1.56 (d, J=7.1 Hz), 1.50-1.33 (m, 4H), 0.94 (m, 3H). LCMS M+H=556.

EXAMPLE 4

3-{[(2-amino-2-benzylhex)oxy]methyl}-N-[1R)-4-fluorophenyl)ethyl]-5-[methyl(methylsulfonyl)amino]benzamide (Scheme 2)

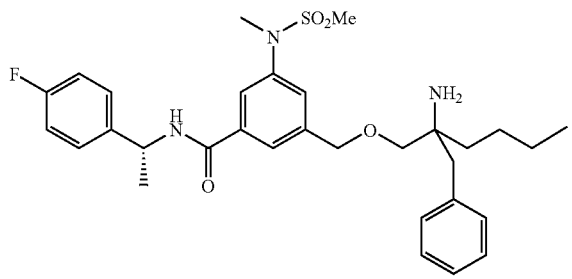

To a solution of 2-amino-2-benzylhexane-1-ol intermediate II (0.100 mg, 0.48 mmol) in 1.1 mL DMF cooled to 0° C. was added sodium hexamethyldisylazide (0.48 mL, 0.48 mmol, 1 M in THF). The reaction mixture was stirred at 0° C. for 5 min and intermediate A 3-(bromomethyl)-N-[(1R)-1-(4-fluorophenyl)ethyl]-5-[methyl(methylsulfonyl)amino] benzamide (0.040 g, 0.090 mmol) in 1.8 mL DMF was added dropwise. The reaction mixture was stirred at 0° C. for 1.5 h, and quenched by adding water. The aqueous layer was washed with EtOAc (3×), and the combined organics were washed with brine, dried over $Na_2SO_4$, filtered and concentrated. Purification by silica gel chromatography (20 g silica, 0->8% 0.1% $NH_4OH$ in i-PrOH/hexanes) afforded 3-{[(2-amino-2-benzylhexyl)oxy]methyl}-N-[(1R)-1-(4-fluorophenyl)ethyl]-5-[methyl(methyl sulfonyl)amino]benzamide. $^1$H NMR (400 MHz, $CDCl_3$) δ 7.73 (s, 1H), 7.69 (s, 1H), 7.53 (s, 1H), 7.37-7.34 (m, 2H), 7.29-7.20 (m, 3H), 7.17-7.15 (m, 2H), 7.04 (m, 2H), 6.56 (br s, 1H), 5.30 (m, 1H), 4.56 (s, 2H), 3.34 (s, 3H), 3.20 (m, 2H), 1.59 (d, J=6.9 Hz, 3H), 1.60-1.39 (br m, 6H), 0.90 (t, J=7.0 Hz, 3H).

EXAMPLE 5

N-(4-[(2-amino-2-methyl-3-phenylpropoxy)methyl]-6-{benzyl[(2-methylcyclopropyl)methyl]amino}pyridin-2-yl)-N-propylmethanesulfonamide (Scheme 4A)

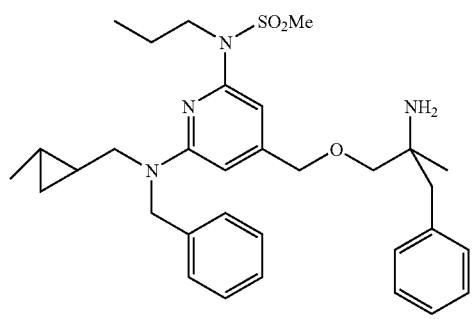

A suspension of tert-butyl [1-benzyl-2-({2-chloro-[(methylsulfonyl)(propyl)amino]pyridin-4-yl}methoxy)-1-methylethyl]carbamate (51 mg, 0.097 mmol, intermediate VI), N-benzyl-1-(2-trans-methylcyclopropyl)methanamine (25 mg, 0.145 mmol, intermediate V), potassium phosphate (62 m, 0.29 mmol) and palladium bis(tri-t-butylphosphine) (5 mg, 0.01 mmol) in degassed toluene (0.32 mL) was sealed in a glass tube and heated to 100° C. for 16 h. The reaction was filtered through celite, rinsed with ethyl acetate and concentrated in vacuo. Flash chromatography (silica, 10-40% EtOAc/hexanes) gave tert-butyl [1-benzyl-2-({2-{benzyl[(2-methylcyclopropyl)methyl]amino}-6-[(methylsulfonyl)(propyl)amino]pyridin-4-yl}methoxy)-1-methylethyl]carbamate. Boc removal in HCl(g) saturated EtOAc provided N-(4-[(2-amino-2-methyl-3-phenylpropoxy)methyl]-6-{benzyl[(2-methylcyclopropyl)methyl]amino}pyridin-2-yl)-N-propylmethanesulfonamide as the hydrochloride. $^1$H NMR (400 MHz, $CD_3OD$ and $CDCl_3$) δ 7.36-7.15 (m, 10H), 6.74 (s, 1H), 6.64 (br s, 1H), 4.92-4.79 (m, 2H), 4.61-4.52 (m, 2H), 3.72-3.60 (m, 3H), 3.46-3.35 (m, 3H), 3.08 (A of AB, d, J=13.2 Hz, 1H), 2.91 (s, 3H), 2.87 (B of AB, d, J=13.2 Hz, 1H), 1.58-1.44 (m, 2H), 1.26 (s, 3H), 0.97 (d, J=6.0 Hz, 3H), 0.88 (t, J=7.6 Hz, 3H), 0.89-0.79 (m, 1H), 0.69-0.61 (m, 1H), 0.45-0.38 (m, 1H), 0.31-0.25 (m, 1H). HRMS (ES, M+H) calcd. for $C_{32}H_{44}N_4O_3S$: 565.3207, found: 565.3208.

EXAMPLE 6

N-(4-[(2-amino-2-methyl-3-phenylpropoxy)methyl]-6-{[(2-methylcyclopropyl)methyl]amino}pyridin-2-yl-N-propylmethanesulfonamide (Scheme 4A)

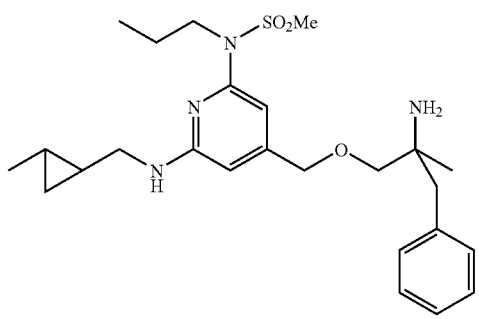

N-(4-[(2-amino-2-methyl-3-phenylpropoxy)methyl]-6-{[(2-methylcyclopropyl)methyl]amino}pyridin-2-yl)-N-propylmethanesulfonamide was prepared from intermediate VI and [(2-methylcyclopropyl)methyl]amine (prepared from N-benzyl-1-(2-trans-methylcyclopropyl)methanamine by hydrogenation on $Pd(OH)_2$, in EtOH, in the presence of TFA), following a similar procedure as described for the preparation of N-4-[(2-amino-2-methyl-3-phenylpropoxy)methyl]-6-{benzyl[(2-methylcyclopropyl)methyl]amino}pyridin-2-yl)-N-propylmethanesulfonamide. HRMS (ES, M+H) calcd. for $C_{25}H_{38}N_4O_3S$: 475.2737, found: 475.2719.

EXAMPLE 7

N-(4-[(2-methyl-3-phenylpropoxy)methyl]-6-{methyl[(2-methylcyclopropyl)methyl]amino}pyridin-2-yl)-N-propylmethanesulfonamide (Scheme 4A)

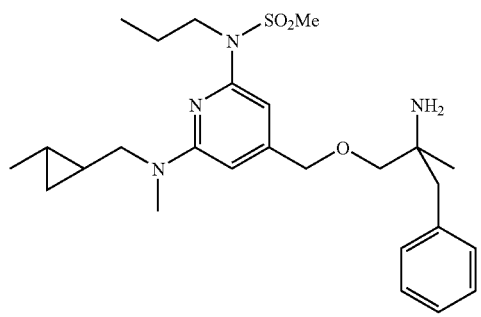

N-(4-[(2-amino-2-methyl-3-phenylpropoxy)methyl]-6-{methyl[(2-methylcyclopropyl)methyl]amino}pyridin-2-yl)-N-propylmethanesulfonamide was prepared from intermediate VI and N-methyl-1-(2-methylcyclopropyl) methanamine (prepared from intermediate V) by methylation with formaldehyde in dichloroethane/methanol, in the presence of NaBH(OAc)$_3$, followed by hydrogenation on Pd(OH)$_2$, in EtOH, in the presence of TFA), following a similar procedure as described for the preparation of N-(4-[(2-amino-2-methyl-3-phenylpropoxy)methyl]-6-{benzyl [(2-methylcyclopropyl)methyl]amino}pyridin-2-yl)-N-propylmethanesulfonamide. HRMS (ES, M+H) calcd. for C$_{26}$H$_{40}$N$_4$O$_3$S: 489.2893, found: 489.2891.

EXAMPLE 8

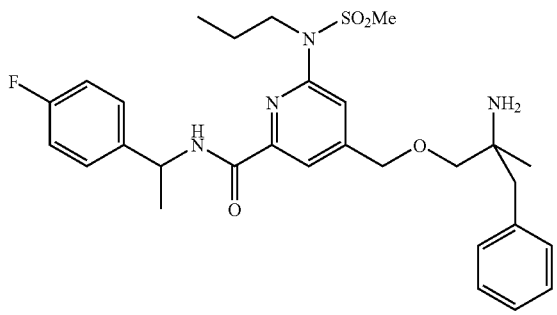

4-[(2-amino-2-methyl-3-phenylpropoxy)methyl]-N-[1-(4-fluorophenyl)ethyl]-6-[(methylsulfonyl)(propyl)amino]pyridine-2-carboxamide (Scheme 7)

To a solution of 4-({2-[(tert-butoxycarbonyl)amino]-2-methyl-3-phenylpropoxy}methyl)-6-[(methylsulfonyl)(propyl)amino]pyridine-2-carboxylic acid (10 mg, 0.019 mmol, intermediate VII) in DMF (0.5 mL) was added diisopropylethyl amine (0.05 mL, 0.028 mmol), [1-(4-fluorophenyl)ethyl]amine (0.008 mL, 0.056 mmol) and BOP reagent (10 mg, 0.022 mmol), and the reaction mixture was allowed to stand at rt for 40 min, purified by preparative HPLC (5->95% CH$_3$CN/H$_2$O, 0.1% added TFA, C18 PRO YMC 20×150 mm) to afford tert-butyl [1-benzyl-2-({2-({[1-(4-fluorophenyl)ethyl]amino}carbonyl)-6-[(methylsulfonyl)(propyl)amino]pyridin-4-yl}methoxy)-1-methylethyl]carbamate. Boc removal in HCl(g) saturated EtOAc and lyophilization from dioxane/water provided 4-[(2-amino-2-methyl-3-phenylpropoxy)methyl]-N-[1-(4-fluorophenyl)ethyl]-6-[(methylsulfonyl)(propyl)amino]pyridine-2-carboxamide as an hydrochloride white solid. $^1$H NMR (400 MHz, CD$_3$OD) δ 8.61 (d, J=8.0 Hz, 1H), 7.97 (s, 1H), 7.65 (s, 1H), 7.46-7.41 (m, 2H), 7.38-7.25 (m, 3H), 7.24-7.19 (m, 2H), 7.11-7.03 (m, 2H), 5.30-5.20 (m, 1H), 4.75 (s, 2H), 4.03-3.94 (m, 2H), 3.51 (A of AB, d, J=10.4 Hz, 1H), 3.46 (B of AB, d, J=10.4 Hz, 1H), 3.11 (A of AB, d, J=13.6 Hz, 1H), 3.10 (s, 3H), 2.92 (B of AB, d, J=13.6 Hz, 1H), 1.64-1.54 (m, 2H), 1.62 (d, J=7.2 Hz, 3H), 1.29 (s, 3H), 0.92 (t, J=7.6 Hz, 3H). HRMS (ES, M+H) calcd. for C$_{29}$H$_{37}$FN$_4$O$_4$S: 557.2593, found: 557.2613.

EXAMPLE 9

N-{4-[(2-amino-2-methyl-3-phenylpropoxy)methyl]-6-[(2-phenylpyrrolidin-1-yl)carbonyl]pyridin-2-yl}-N-propylmethanesulfonamide (Scheme 7)

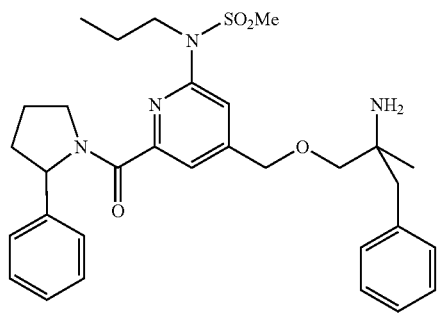

N-{4-[(2-amino-2-methyl-3-phenylpropoxy)methyl]-6-[(2-phenylpyrrolidin-1-yl)carbonyl]pyridin-2-yl}-N-propylmethanesulfonamide was prepared from 4-({2-[(tert-butoxycarbonyl)amino]-2-methyl-3-phenylpropoxy}methyl)-6-[(methylsulfonyl)(propyl)amino]pyridine-2-carboxylic acid (intermediate VII) and 2-phenylpyrrolidine following a similar procedure as described for the preparation of 4-[(2-amino-2-methyl-3-phenylpropoxy)methyl]-N-[1-(4-fluorophenyl)ethyl]-6-[(methylsulfonyl)(propyl)amino]pyridine-2-carboxamide. HRMS (ES, M+H) calcd. for C$_{31}$H$_{40}$N$_4$O$_4$S: 565.2843, found: 565.2859.

EXAMPLE 10

N-{3-({[(2R)-2-methyl-3-phenylpropyl]oxy}methyl)-5-[(Z)-2-(2-methylcyclopropyl)vinyl]phenyl}-N-propylmethanesulfonamide (Scheme 6)

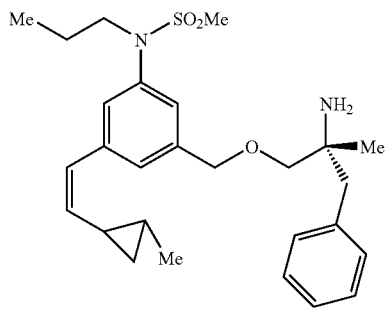

To a solution of (2R)-2-amino-2-methyl-3-phenylpropan-1-ol (0.055 g, 0.334 mmol) in 1 mL DMF at 0° C. was added 1M NaHMDS (0.330 mL, 0.330 mmol). After 10 minutes, N-{3-(bromomethyl)-5-[(Z)-2-(2-methylcyclopropyl)vinyl]phenyl}-N-propylmethanesulfonamide (0.043 g, 0.111 mmol) in 1 mL DMF was added dropwise via cannula. After 1.5 h at 0° C., the reaction was quenched by the addition of 0.5 mL MeOH, and concentrated. The residue was redissolved in 0.80 mL DMF, purified by preparative HPLC (5->95% $CH_3CN/H_2O$, 0.1% added TFA, C18 PRO YMC 20×150 mm), and the fractions containing the desired product were freeze dried to obtain N-{3-({[(2R)-2-amino-2-methyl-3-phenylpropyl]oxy}methyl)-5-[(Z)-2-(2-methylcyclopropyl)vinyl]phenyl}-N-propylmethanesulfonamide as its trifluoroacetate salt. $^1$H NMR (400 MHz, $d_4$-MeOH) δ 7.44 (s, 1H), 7.40 (s, 1H), 7.29-7.26 (m, 4H), 7.15-7.12 (m, 2H), 6.33 (d, J=11.3 Hz, 1H), 5.19 (dd, J=11.3, 10.1 Hz, 1H), 4.67-4.58 (m, 2H), 3.66 (t, J=6.8 Hz, 2H), 3.42 (d, J=9.9 Hz, 1H), 3.35 (9.9 Hz, 1H), 3.07 (d, J=13.4 Hz, 1H), 2.89 (s, 3H), 2.84 (d, J=13.4 Hz, 1H), 1.53-1.39 (m, 3H), 1.22 (s, 3H), 1.07 (d, J=5.9 Hz, 3H), 0.92-0.86 (m, 4H), 0.66 (m, 1H), 0.59 (m, 1H). LCMS [M+H]$^+$=471.

EXAMPLE 11

3-[(2-amino-2-methyl-3-phenylpropoxy)methyl]-N-(1,1-dimethylprop-2-yn-1-yl)-5-[(methylsulfonyl)(propyl)amino]benzamide

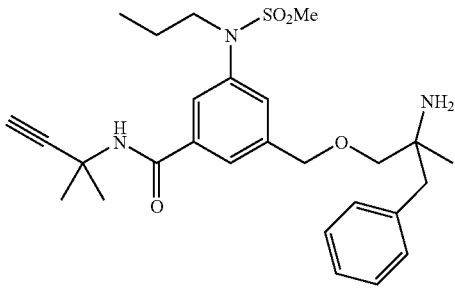

3-({2-[(tert-butoxycarbonyl)amino]-2-methyl-3-phenylpropoxy}methyl)-5-[(methylsulfonyl)(propyl)amino]benzoic acid (intermediate XI, 15.0 mg, 0.028 mmol) was taken up in HCl(g) saturated EtOAc (1 mL). After 30 min, it was concentrated under a flow of nitrogen to give 3-[(2-amino-2-methyl-3-phenylpropoxy)methyl]-5-[(methylsulfonyl)(propyl)amino]benzoic acid as a white solid which was then taken up in DMF (800 μL) with BOP reagent (15.0 mg, 0.033 mmol), ethyl(diisopropyl)amine (12.0 μL, 0.069 mmol), and (1,1-dimethylprop-2-yn-1-yl)amine (23.0 mg, 0.276 mmol). After sitting at RT for 5 hr, the reaction was purified by preparative HPLC (5->95% $CH_3CN/H_2O$, 0.1% added TFA, C18 PRO YMC 20×150 mm) to afford 3-[(2-amino-2-methyl-3-phenylpropoxy)methyl]-N-(1,1-dimethylprop-2-yn-1-yl)-5-[(methylsulfonyl)(propyl)amino]benzamide as a white solid. $^1$H NMR (400 MHz, $CDCl_3$) δ 7.81 (br s, 3H), 7.77 (s, 1H), 7.69 (s, 1H), 7.47 (s, 1H), 7.35-7.27 (m, 3H), 7.22-7.16 (m, 2H), 6.89 (s, 1H), 4.61 (A of AB, d, J=11.7 Hz, 1H), 4.54 (B of AB, d, J=11.7 Hz, 1H), 3.64 (t, J=7.1 Hz, 2H), 3.51 (A of AB, d, J=9.8 Hz, 1H), 3.45 (B of AB, d, J=9.8 Hz, 1H), 3.17 (A of AB, d, J=13.2 Hz, 1H), 3.00 (B of AB, d, J=13.2 Hz, 1H), 2.86 (s, 3H), 1.75 (s, 6H), 1.54-1.44 (m, 2H), 1.32 (s, 3H), 1.27 (s, 3H), 0.89 (t, J=7.3 Hz, 3H).

EXAMPLE 12

3-[(2-amino-2-methyl-3-phenylpropoxy)methyl]-5-[(methylsulfonyl)(propyl)amino]-N-(2,2,2-trifluoro-1-phenylethyl)benzamide

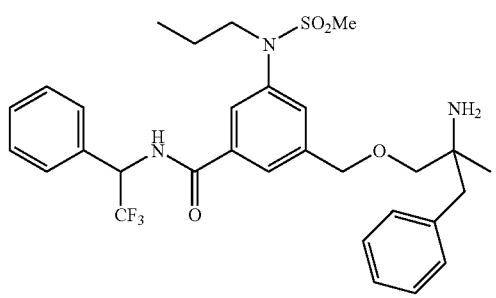

To a solution of 3-({2-[(tert-butoxycarbonyl)amino]-2-methyl-3-phenylpropoxy}methyl)-5-[(methylsulfonyl)(propyl)amino]benzoic acid (intermediate XI, 10.0 mg, 0.019 mmol) and (2,2,2-trifluoro-1-phenylethyl)amine (7.6 mg, 0.056 mmol) in DMF (500 μL) were added BOP reagent (10.0 mg, 0.022 mmol), ethyl(diisopropyl)amine (5.0 μL, 0.028 mmol). After sitting at rt for 4 hr, the reaction was purified by preparative HPLC (5->95% $CH_3CN/H_2O$, 0.1% added TFA, C18 PRO YMC 20×150 mm) to afford tert-butyl {1-benzyl-1-methyl-2-[(3-[(methylsulfonyl)(propyl)amino]-5-{[(2,2,2-trifluoro-1-phenylethyl)amino]carbonyl}benzyl)oxy]ethyl}carbamate which was taken up in HCl(g) saturated EtOAc (1 mL). After 15 hr, it was purified by preparative HPLC (5->95% $CH_3CN/H_2O$, 0.1% added TFA, C18 PRO YMC 20×150 mm) to provide 3-[(2-amino-2-methyl-3-phenylpropoxy)methyl]-5-[(methylsulfonyl)(propyl)amino]-N-(2,2,2-trifluoro-1-phenylethyl)benzamide as a white solid. $^1$H NMR (400 MHz, $CD_3OD$) δ 7.90 (s, 1H), 7.84 (s, 1H), 7.65 (s, 1H), 7.61-7.55 (m, 2H), 7.46-7.40 (m, 3H), 7.34-7.24 (m, 3H), 7.20-7.15 (m, 2H), 6.04-5.96 (m, 1H), 4.72 (A of AB, d, J=13.8 Hz, 1H), 4.68 (B of AB, d, J=13.8 Hz, 1H), 3.71 (t, J=7.1 Hz, 2H), 3.45 (A of AB, d, J=10.0 Hz, 1H), 3.40 (B of AB, d, J=10.0 Hz, 1H), 3.08 (A of AB, d, J=13.4 Hz, 1H), 2.96 (s, 3H), 2.87 (B of AB, d, J=13.4 Hz, 1H), 1.51-1.41 (m, 2H), 1.25 (s, 3H), 0.90 (t, J=7.4 Hz, 3H).

EXAMPLE 13

N-{3-[(2-amino-2-methyl-3-phenylpropoxy)methyl]-5-[(2-phenylpyrrolidin-1-yl)carbonyl]phenyl}-N-propylmethanesulfonamide

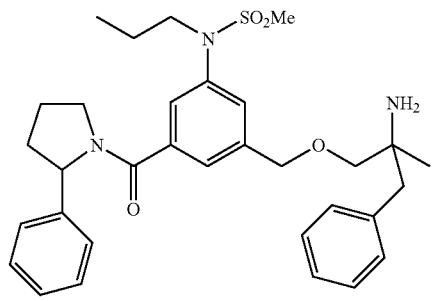

N-{3-[(2-amino-2-methyl-3-phenylpropoxy)methyl]-5-[(2-phenylpyrrolidin-1-yl)carbonyl]phenyl}-N-propyl-methanesulfonamide was prepared from 3-({2-[(tert-butoxycarbonyl)amino]-2-methyl-3-phenylpropoxy}methyl)-5-[(methylsulfonyl)(propyl)amino]benzoic acid (intermediate XI) and 2-phenylpyrrolidine following a similar procedure as described for the preparation of 3-[(2-amino-2-methyl-3-phenylpropoxy)methyl]-5-[(methylsulfonyl)(propyl)amino]-N-(2,2,2-trifluoro-1-phenylethyl)benzamide with additional purification by ion exchange chromatography (Varian Bond Elut SCX, eluting with MeOH followed by 2.0M.NH$_3$ in MeOH). HRMS (ES, M+H) calculated for $C_{32}H_{41}N_3O_4S$: 564.2891, found: 564.2891.

EXAMPLE 14

N-{3-[(2-amino-2-methyl-3-phenylpropoxy)methyl]-5-[(2-propylpyrrolidin-1-yl)carbonyl]phenyl}-N-propylmethanesulfonamide

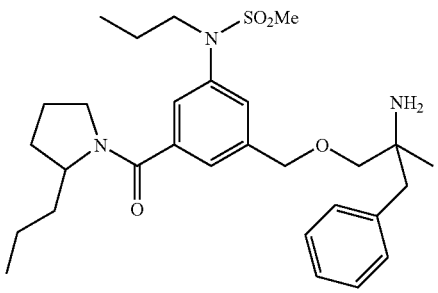

N-{3-[(2-amino-2-methyl-3-phenylpropoxy)methyl]-5-[(2-propylpyrrolidin-1-yl)carbonyl]phenyl}-N-propyl-methanesulfonamide was prepared from 3-({2-[(tert-butoxycarbonyl)amino]-2-methyl-3-phenylpropoxy}methyl)-5-[(methylsulfonyl)(propyl)amino]benzoic acid (intermediate XI) and 2-propylpyrrolidine following a similar procedure as described for the preparation of N-{3-[(2-amino-2-methyl-3-phenylpropoxy)methyl]-5-[(2-phenylpyrrolidin-1-yl)carbonyl]phenyl}-N-propylmethanesulfonamide. HRMS (ES, M+H) calculated for $C_{29}H_{43}N_3O_4S$: 530.3047, found: 530.3045.

EXAMPLE 15

3-[(2-amino-2-methyl-3-phenylpropoxy)methyl]-5-[(methylsulfonyl)(propyl)amino]-N,N-dipropylbenzamide

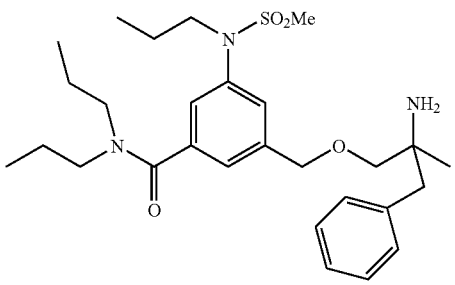

3-[(2-amino-2-methyl-3-phenylpropoxy)methyl]-5-[(methylsulfonyl)(propyl)amino]-N,N-dipropylbenzamide was prepared from 3-({2-[(tert-butoxycarbonyl)amino]-2-methyl-3-phenylpropoxy}methyl)-5-[(methylsulfonyl)(propyl)amino]benzoic acid (intermediate XI) and dipropylamine following a similar procedure as described for the preparation of N-{3-[(2-amino-2-methyl-3-phenylpropoxy)methyl]-5-[(2-phenylpyrrolidin-1-yl)carbonyl]phenyl}-N-propylmethanesulfonamide. HRMS (ES, M+H) calculated for $C_{28}H_{43}N_3O_4S$: 518.3047, found: 518.3051.

EXAMPLE 16

3-[(2-amino-2-methyl-3-phenylpropoxy)methyl]-N-(1-methylbut-2-yn-1-yl)-5-[(methylsulfonyl)(propyl)amino]benzamide

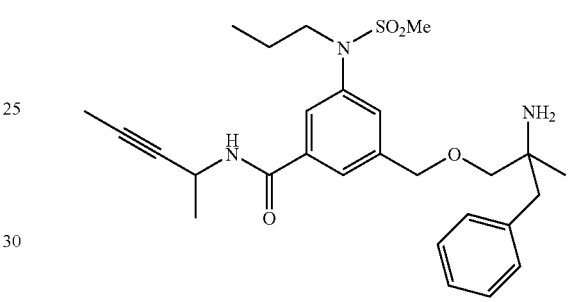

3-[(2-amino-2-methyl-3-phenylpropoxy)methyl]-N-(1-methylbut-2-yn-1-yl)-5-[(methylsulfonyl)(propyl)amino]benzamide was prepared from 3-({2-[(tert-butoxycarbonyl)amino]-2-methyl-3-phenylpropoxy}methyl)-5-[(methylsulfonyl)(propyl)amino]benzoic acid (intermediate XI) and (1-methylbut-2-yn-1-yl)amine (intermediate XIII) following a similar procedure as described for the preparation of N-{3-[(2-amino-2-methyl-3-phenylpropoxy)methyl]-5-[(2-phenylpyrrolidin-1-yl)carbonyl]phenyl}-N-propylmethanesulfonamide. HRMS (ES, M+H) calculated for $C_{27}H_{37}N_3O_4S$: 500.2578, found: 500.2595.

EXAMPLE 17

N-(3-[(2-amino-2-methyl-3-phenylpropoxy)methyl]-5-{[(2,2,2-trifluoro-1-phenylethyl)amino]methyl}phenyl)-N-propylmethanesulfonamide

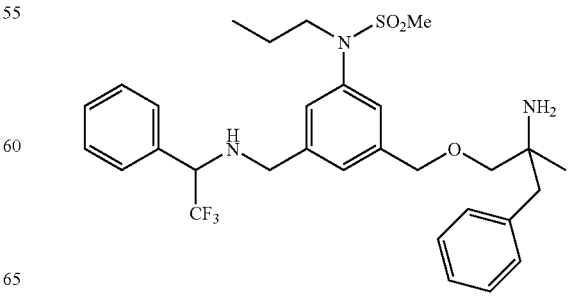

To a solution of N-[3-[(2-amino-2-methyl-3-phenylpropoxy)methyl]-5-(bromomethyl)phenyl]-N-propylmethanesulfonamide (intermediate XII, 25.0 mg, 0.043 mmol) in DMP (500 μL) was added (2,2,2-trifluoro-1-phenylethyl)amine (23.0 mg, 0.129 mmol). After heating at 100° C. for 20 min in the microwave (Smith Synthesizer), the reaction was purified by flash chromatography (silica, 0-35% EtOAc/hexanes) to provide tert-butyl {1-benzyl-1-methyl-2-[(3-[(methylsulfonyl)(propyl)amino]-5-{[(2,2,2-trifluoro-1-phenylethyl)amino]methyl}benzyl)oxy]ethyl}carbamate, which was taken up in HCl in dioxane (1.5 mL, 5.84 mmol, 4.0M). After 5 hr, it was lyophilized from dioxane to provide N-(3-[(2-amino-2-methyl-3-phenylpropoxy)methyl]-5-{[(2,2,2-trifluoro-1-phenylethyl)amino]methyl}phenyl)-N-propylmethanesulfonamide as a white solid. $^1$H NMR (400 MHz, CD$_3$OD) δ 7.58-7.44 (m, 7H), 7.38 (s, 1H), 7.34-7.28 (m, 3H), 7.21-7.17 (m, 2H), 4.89-4.81 (m, 1H), 4.69-4.61 (m, 2H), 4.16-4.0 (m, 2H), 3.66 (m, 2H), 3.47 (A of AB, d, J=10.1 Hz, 1H), 3.41 (B of AB, d, J=10.1 Hz, 1H), 3.09 (A of AB, d, J=13.4 Hz, 1H), 2.94 (s, 3H), 2.89 (B of AB, d, J=13.4 Hz, 1H), 1.50-1.40 (m, 2H), 1.26 (s, 3H), 0.90 (t, J=7.4 Hz, 3H).

EXAMPLE 18

3-[(2-amino-2-methyl-3-phenylpropoxy)methyl]-N-[(1R)-1-(4-fluorophenyl)ethyl]-5[propyl(methylsulfonyl)amino)]benzamide (Scheme 2)

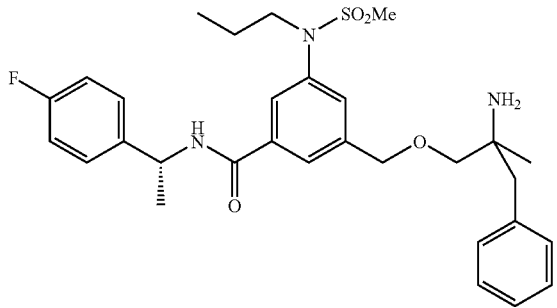

Prepared from 3-(bromomethyl)-N-[(1R)-1-(4-fluorophenyl)ethyl]-5-[propyl(methylsulfonyl)amino]benzamide (intermediate XIV) and 2-amino-2-methyl-3-phenylpropan-1-ol (intermediate I) following a similar procedure as described in Example 1. HRMS (ES, M+H) calcd. for C$_{30}$H$_{38}$FN$_3$O$_4$S: 556.2640, found: 556.2636.

EXAMPLE 19

3-[(2-amino-3-phenylpropoxy)methyl]-N-[1-(4-fluorophenyl)ethyl]-5-[methyl(methylsulfonyl)amino]benzamide

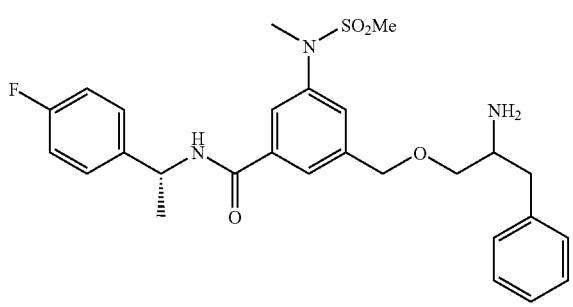

Prepared from 3-(bromomethyl)-N-[(1R)-1-4-fluorophenyl)ethyl]-5-[methyl(methylsulfonyl)amino]benzamide and N-Boc phenylalaninol using a similar procedure as described in Example 1. HRMS (ES, M+H) calcd. for C$_{27}$H$_{32}$FN$_3$O$_4$S: 514.2170, found: 514.2175.

EXAMPLE 20

3-((2-Amino-2-methyl-3-phenylpropoxy)methyl)-5-(1-cyanocyclopentyl)-N-((R)-1-(4-fluorophenyl)ethyl)benzamide

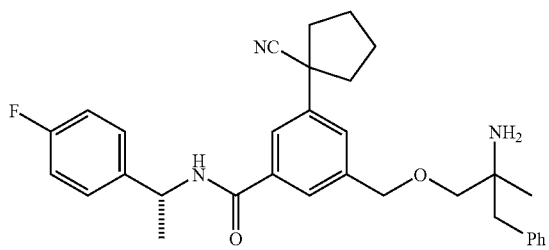

A solution of 3-((2-tert-butoxycarbonylamino-2-methyl-3-phenylpropoxy)methyl)-5-(1-cyanocyclopentyl)benzoic acid (10.25 mg, 0.021 mmol), (R)-1-(4-fluorophenyl)ethanamine (0.0085 mL, 0.063 mmol), benzotriazol-1-yloxy-tris(dimethylamino)-phosphonium hexafluorophosphate (12 mg, 0.025 mmol) and diisopropylethylamine (0.012 mL, 0.07 mmol) in 0.2 mL DMF was stirred at rt overnight. Purification by reverse phase preparative HPLC (5-95% MeCN/H$_2$O containing 0.1% TFA, C18 PRO YMC 20×150 mm) gave 3-((2-tert-butoxycarbonylamino-2-methyl-3-phenylpropoxy)methyl)-5-(1-cyanocyclopentyl)-N-(1-(4-fluorophenyl)ethyl)benzamide which was subsequently dissolved in 0.2 mL CH$_2$Cl$_2$ and 0.5 mL TFA. The reaction mixture was stirred for 1 h and concentrated. Lyophilization gave 3-((2-amino-2-methyl-3-phenylpropoxy)methyl)-5-(1-cyanocyclopentyl)-N-(1-(4-fluorophenyl)ethyl)benzamide as the TFA salt. $^1$H NMR (400 MHz, CD$_3$OD) δ 8.93 (d, J=8.0 Hz, 1H), 7.92 (app d, J=1.6 Hz, 1H), 7.85 (s, 1H), 7.74 (s, 1H), 7.42 (m, 2H), 7.28 (m, 3H), 7.18 (m, 2H), 7.05 (m, 2H), 5.25 (m, 1H), 4.70 (m, 2H), 3.44 (A of AB, d, J=10.1 Hz, 1H), 3.38 (B of AB, d, J=10.1 Hz, 1H), 3.09 (d, J=13.4 Hz, 1H), 2.86 (d, J=13.4 Hz, 1H), 2.50 (m, 2H), 2.18 (m, 2H), 2.03 (m, 4H), 1.58 (d, J=7.0 Hz, 3H), 1.25 (s, 3H).

EXAMPLE 21

3-((2-Amino-2-methyl-3-phenylpropoxy)methyl)-5-(1-cyanocyclopentyl)-N-((R)-1-phenylethyl)benzamide

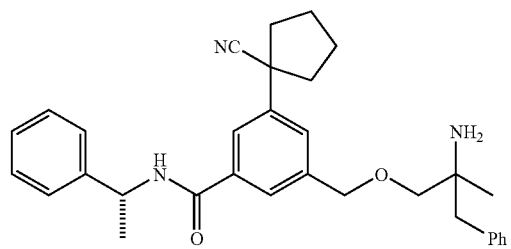

Prepared from 3-((2-tert-butoxycarbonylamino-2-methyl-3-phenylpropoxy)methyl)-5-(1-cyanocyclopentyl)benzoic acid and (R)-1-phenylethanamine using a similar procedure as described for the preparation of Example 20. HRMS ES calculated for $C_{32}H_{37}N_3O_2$: 496.2959, found: 496.2958.

EXAMPLE 22

3-((-2-Amino-2-methyl-3-phenylpropoxy)methyl)-N-benzyl-5-(1-cyanocyclopentyl)benzamide

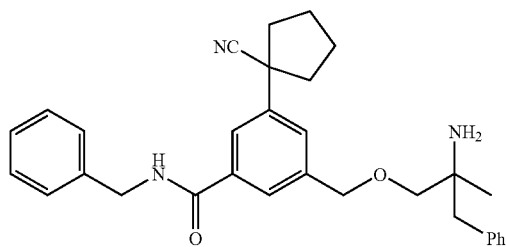

Prepared from 3-((2-tert-butoxycarbonylamino-2-methyl-3-phenylpropoxy)methyl)-5-(1-cyanocyclopentyl)benzoic acid and phenylmethanamine using a similar procedure as described for the preparation of Example 20. HRMS ES calculated for $C_{31}H_{35}N_3O_2$: 482.2802, found: 482.2814.

EXAMPLE 23

3-((2-Amino-2-methyl-3-phenylpropoxy)methyl)-5-(1-cyanocyclopentyl)-N-(2-phenylpyrrolidin-1-yl)benzamide

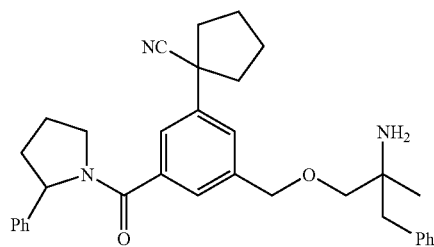

Prepared from 3-((2-tert-butoxycarbonylamino-2-methyl-3-phenylpropoxy)methyl)-5-(1-cyanocyclopentyl)benzoic acid and 2-phenylpyrrolidine using a similar procedure as described for the preparation of Example 20. HRMS ES calculated for $C_{34}H_{39}N_3O_2$: 522.3115, found: 522.3111.

EXAMPLE 24

3-((2-Amino-2-methyl-3-phenylpropoxy)methyl)-N-(1-(3-chlorophenyl)ethyl)-5-(1-cyanocyclopentyl)benzamide

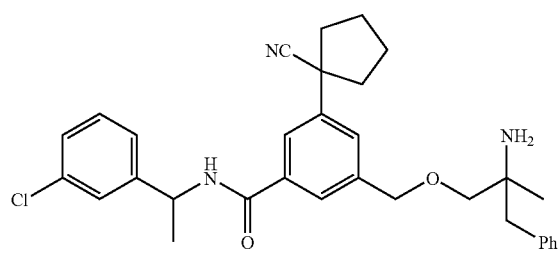

Prepared from 3-((2-tert-butoxycarbonylamino-2-methyl-3-phenylpropoxy)methyl)-5-(1-cyanocyclopentyl)benzoic acid and 1-(3-chlorophenyl)ethanamine using a similar procedure as described for the preparation of Example 20. HRMS ES calculated for $C_{32}H_{36}ClN_3O_2$: 530.2569, found: 530.2565.

EXAMPLE 25

3-((2-Amino-2-methyl-3-phenylpropoxy)methyl)-5-(1-cyanocyclopentyl)-N-(2-propylpyrrolidin-1-yl)benzamide

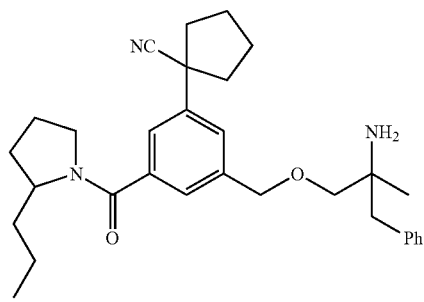

Prepared from 3-((2-tert-butoxycarbonylamino-2-methyl-3-phenylpropoxy)methyl)-5-(1-cyanocyclopentyl)benzoic acid and 2-propylpyrrolidine using a similar procedure as described for the preparation of Example 20. HRMS ES calculated for $C_{31}H_{41}N_3O_2$: 488.3272, found: 488.3284.

EXAMPLE 26

3-((2-Amino-2-methyl-3-phenylpropoxy)methyl)-5-(1-cyanocyclopentyl)-N,N-dipropylbenzamide

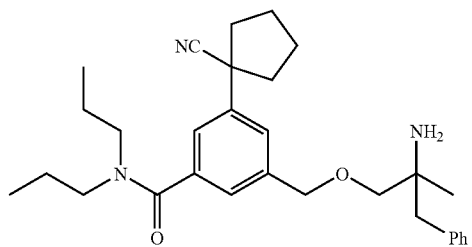

Prepared from 3-((2-tert-butoxycarbonylamino-2-methyl-3-phenylpropoxy)methyl)-5-(1-cyanocyclopentyl)benzoic acid and dipropylamine using a similar procedure as described for the preparation of Example 20. HRMS ES calculated for $C_{30}H_{41}N_3O_2$: 476.3272, found: 476.3272.

EXAMPLE 27

3-((2-Amino-2-methyl-3-phenylpropoxy)methyl)-5-(1-cyanocyclopentyl)-N-(pent-3-yn-2-yl)benzamide

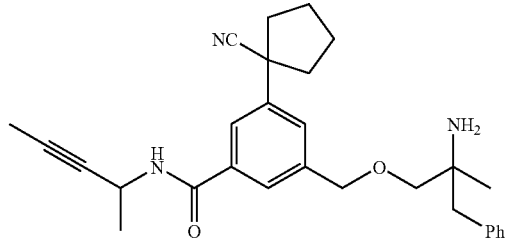

Prepared from 3-((2-tert-butoxycarbonylamino-2-methyl-3-phenylpropoxy)methyl)-5-(1-cyanocyclopentyl)benzoic acid and pent-3-yn-2-amine using a similar procedure as described for the preparation of Example 20. HRMS ES calculated for $C_{29}H_{35}N_3O_2$: 458.2802, found: 458.2813.

EXAMPLE 28

3-((2-Amino-2-methyl-3-phenylpropoxy)methyl)-N-(1-(2-chlorophenyl)ethyl)-5-(1-cyanocyclopentyl)benzamide

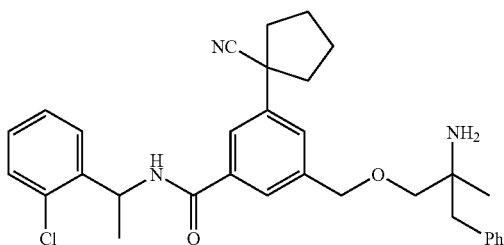

Prepared from 3-((2-tert-butoxycarbonylamino-2-methyl-3-phenylpropoxy)methyl)-5-(1-cyanocyclopentyl)benzoic acid and 1-(2-chlorophenyl)ethanamine using a similar procedure as described for the preparation of Example 20. HRMS ES calculated for $C_{32}H_{36}ClN_3O_2$: 530.2569, found: 530.2561.

EXAMPLE 29

3-((2-Amino-2-methyl-3-phenylpropoxy)methyl)-5-(1-cyanocyclopentyl)-N-2-ethynylpyrrolidin-1-yl)benzamide

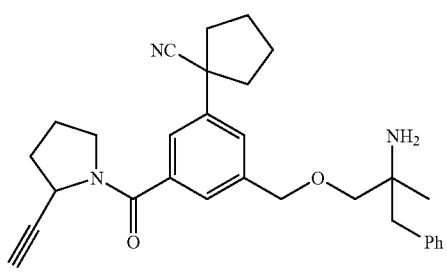

Prepared from 3-((2-tert-butoxycarbonylamino-2-methyl-3-phenylpropoxy)methyl)-5-(1-cyanocyclopentyl)benzoic acid and 2-ethynylpyrrolidine using a similar procedure as described for the preparation of Example 20. HRMS ES calculated for $C_{30}H_{35}N_3O_2$: 470.2802, found: 470.2802.

EXAMPLE 30

3-((2-Amino-2-ethyl-3-phenylpropoxy)methyl)-N-((R)-1-(4-fluorophenyl)ethyl)-5-(N-methyl-N-(methylsulfonyl)amino)benzamide

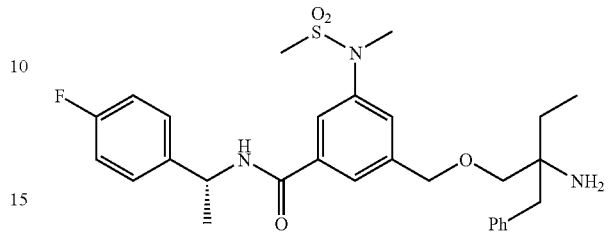

Prepared from 3-(N-methyl-N-(methylsulfonyl)amino)-5-(bromomethyl)-N-((R)-1-(4-fluorophenyl)ethyl)benzamide and 2-amino-2-benzylbutan-1-ol using a similar procedure as described for the preparation of 3-{[(2-amino-2-benzylhexyl)oxy]methyl}-N-[(1R)-1-(4-fluorophenyl)ethyl]-5-[methyl(methyl sulfonyl)amino]benzamide (Example 4). HRMS ES calculated for $C_{29}H_{36}FN_3O_4S$: 542.2484, found: 542.2484.

EXAMPLE 31

3-((2-Amino-2-benzyl-3-phenylpropoxy)methyl)-N-((R)-1-(4-fluorophenyl)ethyl)-5-(N-methyl-N-(methylsulfonyl)amino)benzamide

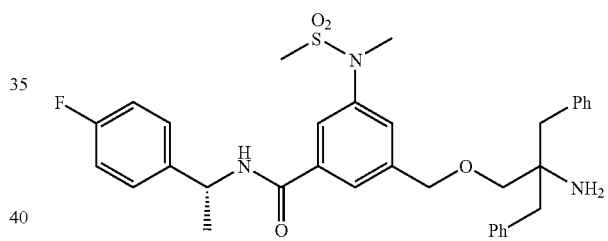

Prepared from 3-(N-methyl-N-(methylsulfonyl)amino)-5-(bromomethyl)-N-((R)-1-(4-fluorophenyl)ethyl)benzamide and 2-amino-2-benzyl-3-phenylpropan-1-ol using a similar procedure as described for the preparation of 3-{[(2-amino-2-benzylhexyl)oxy]methyl}-N-[(1R)-1-(4-fluorophenyl)ethyl]-5-[methyl(methyl sulfonyl)amino]benzamide (Example 4). HRMS ES calculated for $C_{34}H_{38}FN_3O_4S$: 604.2640, found: 604.2641.

EXAMPLE 32

3-((2-Amino-2-difluoromethyl-3-phenylpropoxy)methyl)-N-((R)-1-(4-fluorophenyl)ethyl)-5-(N-methyl-N-(methylsulfonyl)amino)benzamide

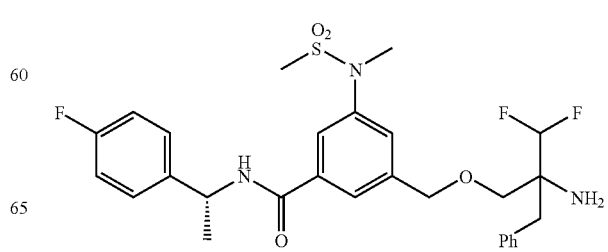

Prepared from 3-N-methyl-N-(methylsulfonyl)amino)-5-bromomethyl)-N-((R)-1-(4-fluorophenyl)ethyl)benzamide and 2-amino-2-(difluoromethyl)-3-phenylpropan-1-ol using a similar procedure as described for the preparation of Example 20. HRMS ES calculated for $C_{28}H_{32}F_3N_3O_4S$: 564.2139, found: 564.2140.

EXAMPLE 33

3-((2-Amino-2-fluoromethyl-3-phenylpropoxy)methyl)-N-((R)-1-(4-fluorophenyl)ethyl)-5-N-methyl-N-(methylsulfonyl)amino)benzamide

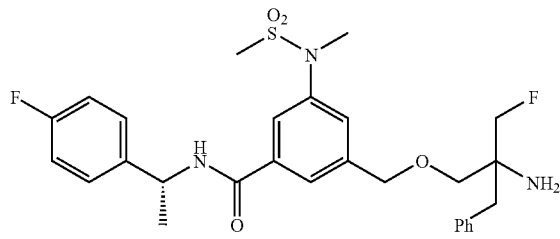

Prepared from 3-(N-methyl-N-(methylsulfonyl)amino)-5-(bromomethyl)-N-((R)-1-(4-fluorophenyl)ethyl)benzamide and 2-amino-2-(fluoromethyl)-3-phenylpropan-1-ol using a similar procedure as described for the preparation of Example 20. $^1$H NMR (400 MHz, CD$_3$OD) δ 8.88 (d, J=7.7 Hz, 1H), 7.84 (s, 1H), 7.80 (s, 1H), 7.63 (s, 1H), 7.42 (m, 2H), 7.32 (m, 3H), 7.19 (d, J=6.2 Hz, 2H), 7.05 (t, J=8.8 Hz, 2H), 5.25 (m, 1H), 4.68 (A of AB, d, J=12.1 Hz, 1H), 4.64 (B of AB, d, J=10.9 Hz, 1H), 4.63-4.44 (two q, ABX system, J=46.6 Hz, J=20.6 Hz, J=10.4 Hz, 2H), 3.54 (m, 2H), 3.35 (s, 3H), 3.08 (s, 2H), 2.93 (s, 3H), 1.58 (d, J=7.0 Hz, 3H).

EXAMPLE 34

3-{[(2-amino-2-methyl-3-phenylpropyl)amino]methyl}-N-[(1R)-1-(4-fluorophenyl)ethyl]-5-[methyl(methylsulfonyl)amino]benzamide

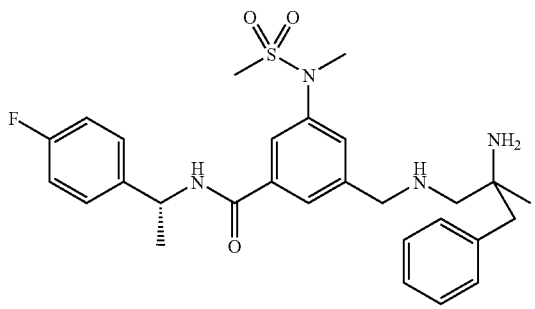

To a flask charged with intermediate III (20 mg, 0.04 mmol) and XXII (24 mg, 0.09 mmol) in iso-propyl alcohol (1 mL) was added K$_2$CO$_3$ (19 mg, 0.14 mmol). After stirring overnight the mixture was filtered, rinsed with EtOAc and the filtrate concentrated to dryness. The crude Boc protected product was subsequently dissolved in 1 mL dichloromethane and treated with trifluoroacetic acid (0.04 mL, 0.50 mmol). After 16 h the reaction was concentrated to dryness under reduced pressure and the crude purified by RP-HPLC to give the title compound, Example 34: $^1$H NMR (400 MHz, CD$_3$OD) δ 8.82 (d, J=8.0 Hz, 1H), 7.82 (m, 2H), 7.66 (s, 1H), 7.41 (m, 2H), 7.30 (m, 3H), 7.18 (m, 2H), 7.03 (td, J=6.8, 2.0 Hz, 2H), 5.23 (q, J=5.2 Hz, 1H), 4.06 (m, 2H), 3.33 (s, 3H), 2.93 (overlapping s, 5H), 2.87 (s, 2H), 1.55 (d, J=7.2 Hz, 3H), 1.29 (s, 3H); HRMS ES calculated for $C_{28}H_{35}FN_4O_3S$: 526.2487, found: 527.2503.

EXAMPLE 35

N-[4-{[(2-amino-2-methyl-3-phenylpropyl)amino]methyl}-6-({[2-methylcyclopropyl]methyl}amino)pyridin-2-yl]-N-methylpropane-2-sulfonamide

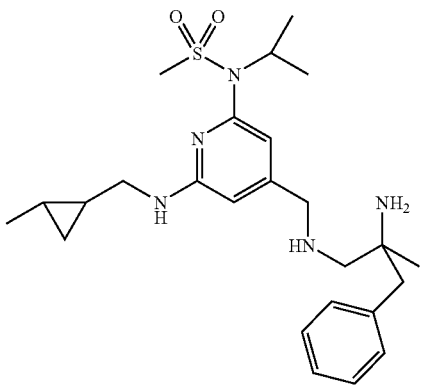

In a vial charged with intermediate amine XXII (37 mg, 0.14 mmol), XXI (32 mg, 0.09 mmol), and HOAt (12 mg, 0.09 mmol) in DCM (1 mL) was added 1-(3-dimethylaminopropyl)-3-ethylcarbodiimide hydrochloride (23 mg, 0.12 mmol). After stirring overnight the reaction was poured onto 10% aq. KHSO$_4$ and extracted with EtOAc (2×10 mL), the organic layers combined and washed with brine. Upon drying over Na$_2$SO$_4$ and solvent removal 50 mg of crude product was obtained: LCMS [M+H]=588.1. Intermediate amide from preceding step was dissolved in THF and treated with BH$_3$-THF (1.8 M, 0.5 mL, 0.9 mmol). The mixture was heated at 60° C. overnight, cooled to rt and quenched with MeOH. The mixture was concentrated to dryness to give crude Boc protected precursor. The crude Boc protected product was subsequently dissolved in 1 mL dichloromethane and treated with trifluoroacetic acid (0.04 mL, 0.50 mmol). After 16 h the reaction was concentrated to dryness under reduced pressure and the crude purified by RP-HPLC to give the title compound, Example 35: $^1$H NMR (400 MHz, CD$_3$OD) δ 7.33 (m, 3H), 7.19 (d, J=6.4 Hz, 2H), 6.51 (s, 1H), 6.35 (s, 1H), 4.05 (m, 3H), 3.33 (s, 3H), 3.14 (sept overlapping m, J=7.2 Hz, 4H), 3.00 (s, 2H), 1.39 (s, 3H), 1.32 (d, J=6.8 Hz, 6H), 1.02 (d, J=6.0 Hz, 3H), 0.81 (m, 1H), 0.63 (m, 1H), 0.37 (m, 1H), 0.20 (m, 1H); HRMS ES calculated for $C_{25}H_{39}N_5O_2S$: 474.2897, found: 474.2925.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:
1. A compound of formula (I):

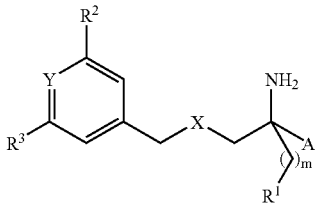

wherein:
X is O or NH;
Y is CH or N;
A is selected from the group consisting of
  (1) hydrogen,
  (2) —$C_{1-10}$ alkyl,
  (3) —$C_{2-10}$ alkenyl, and
  (4) —$C_{2-10}$ alkynyl,
  wherein said alkyl, alkenyl or alkynyl is unsubstituted or substituted with one or more
    (a) halo,
    (b) —$C_{3-8}$ cycloalkyl,
    (c) —OH,
    (d) —CN,
    (e) —O—$C_{1-10}$ alkyl,
    (f) phenyl, or
    (g) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
    and said phenyl and heteroaryl is unsubstituted or substituted with one or more
      (i) halo,
      (ii) —OH,
      (iii) —CN,
      (iv) —O—$C_{1-10}$ alkyl,
      (v) —$C_{1-10}$ alkyl,
      (vi) —$C_{2-10}$ alkenyl,
      (vii) —$C_{2-10}$ alkynyl, or
      (viii) —$C_{3-8}$ cycloalkyl;
$R^1$ is (1) aryl selected from the group consisting of phenyl and napthyl, or
  (2) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
  wherein said aryl or heteroaryl is unsubstituted or substituted with one or more
    (a) halo,
    (b) —$C_{1-10}$ alkyl,
    (c) —$C_{2-10}$ alkenyl,
    (d) —$C_{2-10}$ alkynyl,
    (e) —OH,
    (f) —CN,
    (g) —O—$C_{1-10}$ alkyl, or
    (h) —$C_{3-8}$ cycloalkyl;
$R^2$ is selected from the group consisting of:
  ($R^4$—$SO_2$)N($R^7$)—, wherein $R^4$ is
    (a) —$C_{1-10}$ alkyl,
    (b) —$C_{2-10}$ alkenyl,
    (c) —$C_{2-10}$ alkynyl, or
    (d) —$C_{3-8}$ cycloalkyl,
  wherein said alkyl, alkenyl, alkynyl and cycloalkyl is unsubstituted or substituted with one or more
    (i) halo,
    (ii) —OH,
    (iii) —CN,
    (iv) —O—$C_{1-10}$ alkyl,
    (v) —$C_{1-10}$ alkyl,
    (vi) —$C_{2-10}$ alkenyl,
    (vii) —$C_{2-10}$ alkynyl,
    (viii) —$C_{3-8}$ cycloalkyl,
    (ix) aryl selected from the group consisting of phenyl and napthyl, or
    (x) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
  and said aryl and heteroaryl is unsubstituted or substituted with one or more
    (i) halo,
    (ii) —OH,
    (iii) —CN,
    (iv) —O—$C_{1-10}$ alkyl,
    (v) —$C_{3-8}$ cycloalkyl,
    (vi) —$C_{1-10}$ alkyl,
    (vii) —$C_{2-10}$ alkenyl, or
    (viii) —$C_{2-10}$ alkynyl;
$R^7$ is selected from the group consisting of
  (a) hydrogen,
  (b) —$C_{1-10}$ alkyl,
  (c) —$C_{2-10}$ alkenyl, or
  (d) —$C_{2-10}$ alkynyl;
  wherein said alkyl, alkenyl or alkynyl is unsubstituted or substituted with one or more
    (i) halo,
    (ii) —OH,
    (iii) —CN,
    (iv) —O—$C_{1-10}$ alkyl,
    (v) —$C_{3-8}$ cycloalkyl,
    (vi) aryl selected from the group consisting of phenyl and napthyl, or
    (vii) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
  wherein said cycloalkyl, aryl or heteroaryl is unsubstituted or substituted with one or more
    (i) halo,
    (ii) —OH,
    (iii) —CN,
    (iv) —O—$C_{1-10}$ alkyl,
    (v) —$C_{3-8}$ cycloalkyl, or
    (vi) aryl selected from the group consisting of phenyl and napthyl;

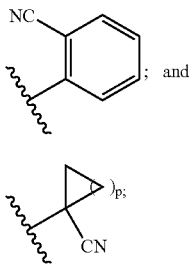
(2)

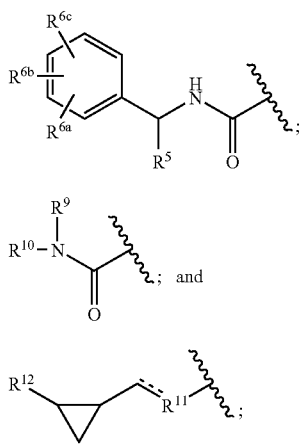
(3)

$R^3$ is selected from the group consisting of (1)

(2)

(3)

wherein $R^5$ is selected from the group consisting of
(1) —$C_{1-10}$ alkyl,
(2) —$C_{2-10}$ alkenyl,
(3) —$C_{2-10}$ alkynyl
wherein said alkyl, alkenyl or alkynyl is unsubstituted or substituted with one or more halo;
$R^{6a}$, $R^{6b}$, and $R^{6c}$ are independently selected from the group consisting of:
(1) hydrogen,
(2) halo,
(3) —$C_{1-10}$ alkyl,
(4) —$C_{2-10}$ alkenyl,
(5) —$C_{2-10}$ alkynyl,
(6) —OH,
(7) —CN,
(8) —$C_{3-8}$ cycloalkyl, and
(9) —O—$C_{1-10}$ alkyl;
$R^9$ and $R^{10}$ are independently selected from the group consisting of
(1) hydrogen,
(2) —$C_{1-10}$ alkyl,
(3) —$C_{2-10}$ alkenyl,
(4) —$C_{2-10}$ alkynyl, or
(5) —$C_{3-8}$ cycloalkyl;
wherein said alkyl, alkenyl, alkynyl or cycloalkyl is unsubstituted or substituted with one or more
(a) halo,
(b) —OH,
(c) —CN,
(d) —$C_{3-8}$ cycloalkyl,
(e) —O—$C_{1-10}$ alkyl or $R^9$ and $R^{10}$ are joined together with the nitrogen atom to which they are attached to form a pyrrolidine ring, which is unsubstituted or substituted with one or more
(a) —$C_{1-10}$ alkyl,
(b) —$C_{2-10}$ alkenyl,
(c) —$C_{2-10}$ alkynyl,
(d) —$C_{3-8}$ cycloalkyl,
(e) —$(CH_2)_n$-phenyl,
(f) —CN,
wherein said alkyl, alkenyl or alkynyl is unsubstituted or substituted with one or more
i) halo,
ii) —OH,
iii) —CN,
iv) —O—$C_{1-10}$ alkyl, or
v) —$C_{3-8}$ cycloalkyl;
and said cycloalkyl and phenyl is unsubstituted or substituted with one or more
i) halo,
ii) —$C_{1-10}$ alkyl,
iii) —$C_{2-10}$ alkenyl,
iv) —$C_{2-10}$ alkynyl,
v) —OH,
vi) —CN,
vii) —$C_{3-8}$ cycloalkyl, or
viii) —O—$C_{1-10}$ alkyl;
$R^{11}$ is selected from the group consisting of
(1) —CH—,
(2) —O—, and
(3) —$NR^8$—,
provided that when $R^{11}$ is —CH— the dotted line forms a bond and when $R^{11}$ is —O— or —$NR^8$— the dotted line is absent;
$R^8$ is selected from the group consisting of
(1) hydrogen,
(2) —$C_{1-10}$ alkyl,
(3) —$C_{2-10}$ alkenyl,
(4) —$C_{2-10}$ alkynyl, or
(5) —$CH_2$— phenyl,
wherein said alkyl, alkenyl, alkynyl or phenyl is unsubstituted or substituted with one or more
(a) halo,
(b) —OH,
(c) —CN,
(d) —$C_{3-8}$ cycloalkyl,
(e) —O—$C_{1-10}$ alkyl;
$R^{12}$ is selected from the group consisting of
(1) hydrogen,
(2) —$C_{1-10}$ alkyl;
(3) —$C_{2-10}$ alkenyl,
(4) —$C_{2-10}$ alkynyl,
(5) halo,
(6) —$C_{3-8}$ cycloalkyl,
(7) aryl selected from the group consisting of phenyl and napthyl, and
(8) heteroaryl selected from the group consisting of pyrazinyl, pyrazolyl, pyridazinyl, pyridyl, pyrimidinyl, pyrrolyl, tetrazolyl, furanyl, imidazolyl, triazinyl, pyranyl, thiazolyl, thienyl, thiophenyl, triazolyl, oxazolyl, isoxazolyl, thiazolyl, oxadiazolyl, indolyl, quinolinyl, isoquinolinyl, benzimidazolyl and benzoxazolyl,
wherein said aryl and heteroaryl is unsubstituted or substituted with one or more
(a) halo,
(b) —OH,
(c) —CN, (d) —O—$C_{1-10}$ alkyl,
(e) —$C_{3-8}$ cycloalkyl,
(f) —$C_{1-10}$ alkyl,
(g) —$C_{2-10}$ alkenyl, or
(h) —$C_{2-10}$ alkynyl;

m is 0, 1, 2 or 3;
n is 0, 1, 2, 3 or 4;
p is 1, 2, 3 or 4;
provided that A is not $CH_2OH$;
or a pharmaceutically acceptable salt thereof.

2. The compound of claim 1 wherein m is 1 and $R^1$ is phenyl.

3. The compound of claim 1 wherein $R^2$ is ($R^4$—$SO_2$)N($R^7$)—.

4. The compound of claim 3 wherein $R^4$ and $R^7$ are methyl.

5. The compound of claim 1 wherein A is unsubstituted $C_{1-6}$ alkyl or unsubstituted $C_{2-6}$ alkenyl.

6. The compound of claim 1 wherein $R^3$ is

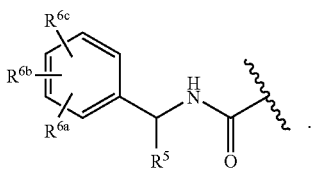

7. The compound of claim 1 wherein Y is CH.
8. The compound of claim 1 wherein Y is N.
9. The compound of claim 1 wherein X is O.
10. A compound selected from the group consisting of
3-[(2-amino-2-methyl-3-phenylpropoxy)methyl]-N-[(1R)-1-(4-fluorophenyl)ethyl]-5-[methyl(methylsulfonyl)amino]benzamide;
3-{[(2-amino-2-benzylpent-4-en-1-yl)oxy]methyl}-N-[(1R)-1-(4-fluorophenyl)ethyl]-5-[methyl(methylsulfonyl)amino]benzamide;
3-{[(2-amino-2-benzylpentyl)oxy]methyl}-N-[(1R)-1-(4-fluorophenyl)ethyl]-5-[methyl(methylsulfonyl)amino]benzamide;
3-{[(2-amino-2-benzylhexyl)oxy]methyl}-N-[(1R)-1-(4-fluorophenyl)ethyl]-5-[methyl(methylsulfonyl)amino]benzamide;
N-(4-[(2-amino-2-methyl-3-phenylpropoxy)methyl]-6-{benzyl[(2-methylcyclopropyl)methyl]amino}pyridin-2-yl)-N-propylmethanesulfonamide;
N-(4-[(2-amino-2-methyl-3-phenylpropoxy)methyl]-6-{[(2-methylcyclopropyl)methyl]amino}pyridin-2-yl)-N-propylmethanesulfonamide;
N-(4-[(2-amino-2-methyl-3-phenylpropoxy)methyl]-6-{methyl[(2-methylcyclopropyl)methyl]amino}pyridin-2-yl)-N-propylmethanesulfonamide;
4-[(2-amino-2-methyl-3-phenylpropoxy)methyl]-N-[1-(4-fluorophenyl)ethyl]-6-[(methylsulfonyl)(propyl)amino]pyridine-2-carboxamide;
N-{4-[(2-amino-2-methyl-3-phenylpropoxy)methyl]-6-[(2-phenylpyrrolidin-1-yl)carbonyl]pyridin-2-yl}-N-propylmethanesulfonamide;
N-{3-({[(2R)-2-amino-2-methyl-3-phenylpropyl]oxy}methyl)-5-[(Z)-2-(2-methylcyclopropyl)vinyl]phenyl}-N-propylmethanesulfonamide;
3-[(2-amino-2-methyl-3-phenylpropoxy)methyl]-N-(1,1-dimethylprop-2-yn-1-yl)-5-[(methylsulfonyl)(propyl)amino]benzamide;
3-[(2-amino-2-methyl-3-phenylpropoxy)methyl]-5-[(methylsulfonyl)(propyl)amino]-N-(2,2,2-trifluoro-1-phenylethyl)benzamide;
N-{3-[(2-amino-2-methyl-3-phenylpropoxy)methyl]-5-[(2-phenylpyrrolidin-1-yl)carbonyl]phenyl}-N-propylmethanesulfonamide;
N-{3-[(2-amino-2-methyl-3-phenylpropoxy)methyl]-5-[(2-propylpyrrolidin-1-yl)carbonyl]phenyl}-N-propylmethanesulfonamide;
3-[(2-amino-2-methyl-3-phenylpropoxy)methyl]-5-[(methylsulfonyl)(propyl)amino]-N,N-dipropylbenzamide;
3-[(2-amino-2-methyl-3-phenylpropoxy)methyl]-N-(1-methylbut-2-yn-1-yl)-5-[(methylsulfonyl)(propyl)amino]benzamide;
N-(3-[(2-amino-2-methyl-3-phenylpropoxy)methyl]-5-{[(2,2,2-trifluoro-1-phenylethyl)amino]methyl}phenyl)-N-propylmethanesulfonamide;
3-[(2-amino-2-methyl-3-phenylpropoxy)methyl]-N-[(1R)-1-(4-fluorophenyl)ethyl]-5-[propyl(methylsulfonyl)amino]benzamide;
3-[(2-amino-3-phenylpropoxy)methyl]-N-[1-(4-fluorophenyl)ethyl]-5-[methyl(methylsulfonyl)amino]benzamide;
3-((2-Amino-2-methyl-3-phenylpropoxy)methyl)-5-(1-cyanocyclopentyl)-N-((R)-1-(4-fluorophenyl)ethyl)benzamide;
3-((2-Amino-2-methyl-3-phenylpropoxy)methyl)-5-(1-cyanocyclopentyl)-N-((R)-1-phenylethyl)benzamide;
3-((-2-Amino-2-methyl-3-phenylpropoxy)methyl)-N-benzyl-5-(1-cyanocyclopentyl)benzamide;
3-((2-Amino-2-methyl-3-phenylpropoxy)methyl)-5-(1-cyanocyclopentyl)-N-(2-phenylpyrrolidin-1-yl)benzamide;
3-((2-Amino-2-methyl-3-phenylpropoxy)methyl)-N-(1-(3-chlorophenyl)ethyl)-5-(1-cyanocyclopentyl)benzamide;
3-((2-Amino-2-methyl-3-phenylpropoxy)methyl)-5-(1-cyanocyclopentyl)-N-(2-propylpyrrolidin-1-yl)benzamide;
3-((2-Amino-2-methyl-3-phenylpropoxy)methyl)-5-(1-cyanocyclopentyl)-N,N-dipropylbenzamide;
3-((2-Amino-2-methyl-3-phenylpropoxy)methyl)-5-(1-cyanocyclopentyl)-N-(pent-3-yn-2-yl)benzamide;
3-((2-Amino-2-methyl-3-phenylpropoxy)methyl)-N-(1-(2-chlorophenyl)ethyl)-5-(1-cyanocyclopentyl)benzamide;
3-((2-Amino-2-methyl-3-phenylpropoxy)methyl)-5-(1-cyanocyclopentyl)-N-(2-ethynylpyrrolidin-1-yl)benzamide;
3-((2-Amino-2-ethyl-3-phenylpropoxy)methyl)-N-((R)-1-(4-fluorophenyl)ethyl)-5-(N-methyl-N-(methylsulfonyl)amino)benzamide;
3-((2-Amino-2-benzyl-3-phenylpropoxy)methyl)-N-((R)-1-(4-fluorophenyl)ethyl)-5-(N-methyl-N-(methylsulfonyl)amino)benzamide;
3-((2-Amino-2-difluoromethyl-3-phenylpropoxy)methyl)-N-((R)-1-(4-fluorophenyl)ethyl)-5-(N-methyl-N-(methylsulfonyl)amino)benzamide;
3-((2-Amino-2-fluoromethyl-3-phenylpropoxy)methyl)-N-((R)-1-(4-fluorophenyl)ethyl)-5-(N-methyl-N-(methylsulfonyl)amino)benzamide;
3-{[(2-amino-2-methyl-3-phenylpropyl)amino]methyl}-N-[(1R)-1-(4-fluorophenyl)ethyl]-5-[methyl(methylsulfonyl)amino]benzamide;
N-[4-{[(2-amino-2-methyl-3-phenylpropyl)amino]methyl}-6-({[2-methylcyclopropyl]methyl}amino)pyridin-2-yl]-N-methylpropane-2-sulfonamide;
or a pharmaceutically acceptable salt thereof.

11. The compound of claim 1 of formula (II)

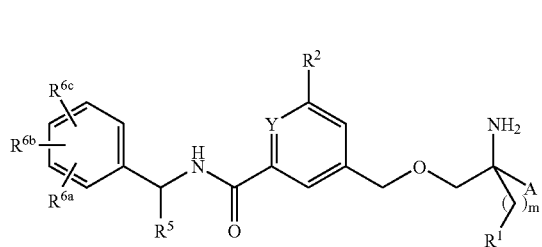

or a pharmaceutically acceptable salt thereof.

12. The compound of claim 1 of formula (III)

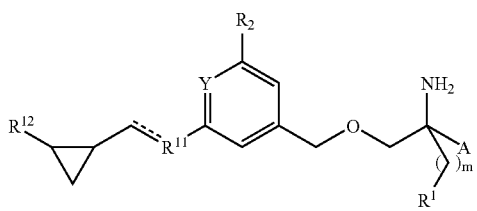

or a pharmaceutically acceptable salt thereof.

13. The compound of claim 12 wherein Y is N and $R^{11}$ is $NR^8$.

14. A compound of claim 1 of formula (IV)

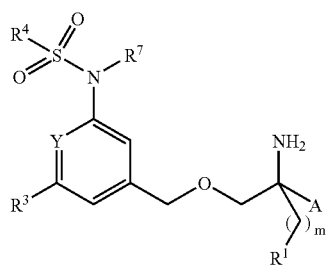

or a pharmaceutically acceptable salt thereof.

15. The compound of claim 1 of formula (V)

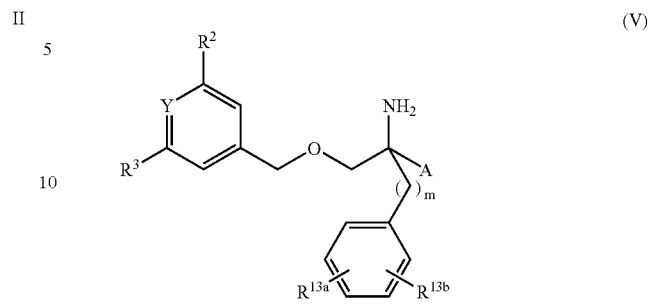

wherein $R^{13a}$ and $R^{13b}$ are independently selected from the group consisting of
(a) halo,
(b) —$C_{1-10}$ alkyl,
(c) —OH,
(d) —CN,
(e) —O—$C_{1-10}$alkyl,
(f) hydrogen, and
(g) —$C_{3-8}$ cycloalkyl;
m is 1; or a pharmaceutically acceptable salt thereof.

16. The compound of claim 1 of formula (VI)

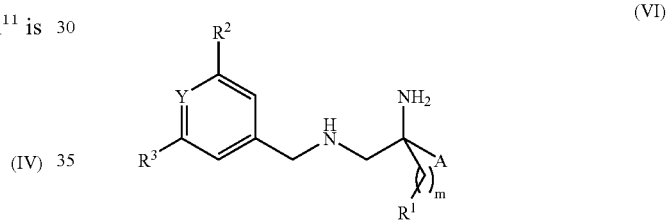

or a pharmaceutically acceptable salt thereof.

17. A pharmaceutical composition comprising a therapeutically effective amount of a compound of claim 1 and a pharmaceutically acceptable carrier.

18. A method for treating Alzheimer's disease in a patient in need thereof comprising administering to the patient a therapeutically effective amount of a compound of claim 1.

* * * * *